US012797489B2

(12) United States Patent
Zhou et al.

(10) Patent No.: US 12,797,489 B2
(45) Date of Patent: Nov. 17, 2026

(54) USE OF TRANSDIFFERENTIATION OF GLIAL CELLS INTO NEURONS IN PREVENTION OR TREATMENT OF DISEASES ASSOCIATED WITH NEURON LOSS-OF-FUNCTION OR DEATH

(71) Applicant: SHANGHAI GENEMAGIC BIOSCIENCES CO., LTD., Shanghai (CN)

(72) Inventors: Haibo Zhou, Shanghai (CN); Xinde Hu, Shanghai (CN); Jinlin Su, Shanghai (CN)

(73) Assignee: SHANGHAI GENEMAGIC BIOSCIENCES CO., LTD., Shanghai (CN)

( * ) Notice: Subject to any disclaimer, the term of this patent is extended or adjusted under 35 U.S.C. 154(b) by 599 days.

(21) Appl. No.: 18/264,923

(22) PCT Filed: Feb. 10, 2022

(86) PCT No.: PCT/CN2022/075823

§ 371 (c)(1),
(2) Date: Aug. 9, 2023

(87) PCT Pub. No.: WO2022/171167

PCT Pub. Date: Aug. 18, 2022

(65) Prior Publication Data

US 2025/0281648 A1 Sep. 11, 2025

(30) Foreign Application Priority Data

Feb. 10, 2021 (CN) ......................... 202110185323.2

(51) Int. Cl.
*A61K 48/00* (2006.01)
*C12N 9/22* (2006.01)
*C12N 15/11* (2006.01)

(52) U.S. Cl.
CPC ........ *A61K 48/0075* (2013.01); *A61K 48/005* (2013.01); *C12N 9/226* (2025.05); *C12N 15/11* (2013.01); *C12N 2310/20* (2017.05)

(58) Field of Classification Search
None
See application file for complete search history.

(56) References Cited

U.S. PATENT DOCUMENTS 5,935,811 A 8/1999 Anderson et al.
2005/0201995 A1 9/2005 Majumder
2015/0190377 A1 7/2015 Chandran et al.
2015/0299698 A1* 10/2015 Fu ........................ A61K 31/713 435/351

FOREIGN PATENT DOCUMENTS

CA 3 096 691 10/2019
CN 105950557 A 9/2016
CN 112312928 A 2/2021
WO WO-2017075406 A1 * 5/2017 ......... C12N 15/1051

OTHER PUBLICATIONS

Zhou, H. et al Glia-to-Neuron Conversion by CRISPR-CasRx Alleviates Symptoms of Neurological Disease in Mice. Cell, 181(3), 590-603.e16. https://doi.org/10.1016/j.cell.2020.03.024 (Year: 2020).*
Yang, Hui, "Glia-to Neuron Conversion Alleviates Symptoms of Neurological Disease in Mice." Bulletin of the Chinese Academy of Sciences, vol. 34, No. 1, 2020, pp. 57-58.
Zhao, Xuewei et al. "mRNA Delivery Using Bioreducible Lipidoid Nanoparticles Facilitates Neural Differentiation of Human Mesenchymal Stem Cells" Advanced Healthcare Materials, vol. 10, Aug. 19, 2020, Article No. 2000938, pp. 1-7.
Pang, Xining. "Cell Reprogramming: Control Key Genes to Obtain Needed Cells" Acta Academiae Medicinae Sinicae, vol. 33, No. 06, Dec. 30, 2011, pp. 689-692 (English Language Abstract).
Zhang, Jing et al. "Regulatory Role of NRSF/REST on Development and Differentiation of Stem Cells" Progress in Biochemistry and Biophysics, vol. 38, No. 09, pp. 791-794, with translation.
Gall, A. D. "The role of the Re-1 silencing transcription factor (Rest) in the injury response of Muller glia in the murine retina" A Thesis of the Department of Biology University of Houston, Aug. 31, 2014, abstract.
Xue, Yuanchao et al., "Direct Conversion of Fibroblasts to Neurons by Reprogramming PTB-Regulated microRNA Circuits" NIH Public Access, Cell. Jan. 17, 2013; 152(102): 82-96. doi:10.1016/j.cell.2012.11.045.
Xue, Yuanchao et al., "Sequential Regulatory Loops as Key Gatekeepers for Neuronal Reprogramming in Human Cells" HHS Public Access, Nat Neurosci. Jun. 2016; 19(6): 807-815. doi:10.1038/nn.4297.

* cited by examiner

*Primary Examiner* — Allison M Fox
*Assistant Examiner* — Caroline M Lara
(74) *Attorney, Agent, or Firm* — Wenderoth, Lind & Ponack, L.L.P.

(57) ABSTRACT

The transdifferentiation of glial cells into neurons is useful for prevention or treatment of a disease associated with loss of function or death. The present disclosure relates to the field of biomedicines. More specifically, the present disclosure relates to use of a REST inhibitor in the treatment of a disease associated with loss of function or death of neurons. The present disclosure can effectively induce transdifferentiation of astrocytes into dopamine neurons by inhibiting the expression, content or activity of a gene of REST or an RNA thereof or an encoding protein thereof in astrocytes in the brain, and can effectively induce transdifferentiation of Müller glia (MG) into retinal ganglion cells (RGCs) or photoreceptor cells by inhibiting the expression, content or activity of the gene of REST or the RNA thereof or the encoding protein thereof in the retina, thereby preventing and/or treating the disease associated with loss of function or death of neurons.

13 Claims, 7 Drawing Sheets

Specification includes a Sequence Listing.

SEQUENCE LISTING

<160> NUMBER OF SEQ ID NOS: 202

<210> SEQ ID NO 1
<211> LENGTH: 1097
<212> TYPE: PRT
<213> ORGANISM: Homo sapiens

<400> SEQUENCE: 1

Met Ala Thr Gln Val Met Gly Gln Ser Ser Gly Gly Gly Gly Leu Phe
1 5 10 15

Thr Ser Ser Gly Asn Ile Gly Met Ala Leu Pro Asn Asp Met Tyr Asp
20 25 30

Leu His Asp Leu Ser Lys Ala Glu Leu Ala Ala Pro Gln Leu Ile Met
35 40 45

Leu Ala Asn Val Ala Leu Thr Gly Glu Val Asn Gly Ser Cys Cys Asp
50 55 60

Tyr Leu Val Gly Glu Glu Arg Gln Met Ala Glu Leu Met Pro Val Gly
65 70 75 80

Asp Asn Asn Phe Ser Asp Ser Glu Glu Gly Glu Gly Leu Glu Glu Ser
85 90 95

Ala Asp Ile Lys Gly Glu Pro His Gly Leu Glu Asn Met Glu Leu Arg
100 105 110

Ser Leu Glu Leu Ser Val Val Glu Pro Gln Pro Val Phe Glu Ala Ser
115 120 125

Gly Ala Pro Asp Ile Tyr Ser Ser Asn Lys Asp Leu Pro Pro Glu Thr
130 135 140

Pro Gly Ala Glu Asp Lys Gly Lys Ser Ser Lys Thr Lys Pro Phe Arg
145 150 155 160

Cys Lys Pro Cys Gln Tyr Glu Ala Glu Ser Glu Glu Gln Phe Val His
165 170 175

His Ile Arg Val His Ser Ala Lys Lys Phe Phe Val Glu Glu Ser Ala
180 185 190

Glu Lys Gln Ala Lys Ala Arg Glu Ser Gly Ser Ser Thr Ala Glu Glu
195 200 205

Gly Asp Phe Ser Lys Gly Pro Ile Arg Cys Asp Arg Cys Gly Tyr Asn
210 215 220

Thr Asn Arg Tyr Asp His Tyr Thr Ala His Leu Lys His His Thr Arg
225 230 235 240

Ala Gly Asp Asn Glu Arg Val Tyr Lys Cys Ile Ile Cys Thr Tyr Thr
245 250 255

Thr Val Ser Glu Tyr His Trp Arg Lys His Leu Arg Asn His Phe Pro
260 265 270

Arg Lys Val Tyr Thr Cys Gly Lys Cys Asn Tyr Phe Ser Asp Arg Lys
275 280 285

Asn Asn Tyr Val Gln His Val Arg Thr His Thr Gly Glu Arg Pro Tyr
290 295 300

Lys Cys Glu Leu Cys Pro Tyr Ser Ser Ser Gln Lys Thr His Leu Thr
305 310 315 320

Arg His Met Arg Thr His Ser Gly Glu Lys Pro Phe Lys Cys Asp Gln
325 330 335

Cys Ser Tyr Val Ala Ser Asn Gln His Glu Val Thr Arg His Ala Arg
340 345 350

Gln Val His Asn Gly Pro Lys Pro Leu Asn Cys Pro His Cys Asp Tyr
355 360 365

-continued

```
Lys Thr Ala Asp Arg Ser Asn Phe Lys Lys His Val Glu Leu His Val
    370                 375                 380

Asn Pro Arg Gln Phe Asn Cys Pro Val Cys Asp Tyr Ala Ala Ser Lys
385                 390                 395                 400

Lys Cys Asn Leu Gln Tyr His Phe Lys Ser Lys His Pro Thr Cys Pro
                405                 410                 415

Asn Lys Thr Met Asp Val Ser Lys Val Lys Leu Lys Lys Thr Lys Lys
            420                 425                 430

Arg Glu Ala Asp Leu Pro Asp Asn Ile Thr Asn Glu Lys Thr Glu Ile
        435                 440                 445

Glu Gln Thr Lys Ile Lys Gly Asp Val Ala Gly Lys Lys Asn Glu Lys
    450                 455                 460

Ser Val Lys Ala Glu Lys Arg Asp Val Ser Lys Glu Lys Lys Pro Ser
465                 470                 475                 480

Asn Asn Val Ser Val Ile Gln Val Thr Thr Arg Thr Arg Lys Ser Val
                485                 490                 495

Thr Glu Val Lys Glu Met Asp Val His Thr Gly Ser Asn Ser Glu Lys
            500                 505                 510

Phe Ser Lys Thr Lys Lys Ser Lys Arg Lys Leu Glu Val Asp Ser His
        515                 520                 525

Ser Leu His Gly Pro Val Asn Asp Glu Glu Ser Ser Thr Lys Lys Lys
    530                 535                 540

Lys Lys Val Glu Ser Lys Ser Lys Asn Asn Ser Gln Glu Val Pro Lys
545                 550                 555                 560

Gly Asp Ser Lys Val Glu Glu Asn Lys Lys Gln Asn Thr Cys Met Lys
                565                 570                 575

Lys Ser Thr Lys Lys Lys Thr Leu Lys Asn Lys Ser Ser Lys Lys Ser
            580                 585                 590

Ser Lys Pro Pro Gln Lys Glu Pro Val Glu Lys Gly Ser Ala Gln Met
        595                 600                 605

Asp Pro Pro Gln Met Gly Pro Ala Pro Thr Glu Ala Val Gln Lys Gly
    610                 615                 620

Pro Val Gln Val Glu Pro Pro Pro Pro Met Glu His Ala Gln Met Glu
625                 630                 635                 640

Gly Ala Gln Ile Arg Pro Ala Pro Asp Glu Pro Val Gln Met Glu Val
                645                 650                 655

Val Gln Glu Gly Pro Ala Gln Lys Glu Leu Leu Pro Pro Val Glu Pro
            660                 665                 670

Ala Gln Met Val Gly Ala Gln Ile Val Leu Ala His Met Glu Leu Pro
        675                 680                 685

Pro Pro Met Glu Thr Ala Gln Thr Glu Val Ala Gln Met Gly Pro Ala
    690                 695                 700

Pro Met Glu Pro Ala Gln Met Glu Val Ala Gln Val Glu Ser Ala Pro
705                 710                 715                 720

Met Gln Val Val Gln Lys Glu Pro Val Gln Met Glu Leu Ser Pro Pro
                725                 730                 735

Met Glu Val Val Gln Lys Glu Pro Val Gln Ile Glu Leu Ser Pro Pro
            740                 745                 750

Met Glu Val Val Gln Lys Glu Pro Val Lys Ile Glu Leu Ser Pro Pro
        755                 760                 765

Ile Glu Val Val Gln Lys Glu Pro Val Gln Met Glu Leu Ser Pro Pro
    770                 775                 780
```

```
Met Gly Val Val Gln Lys Glu Pro Ala Gln Arg Glu Pro Pro Pro Pro
785                 790                 795                 800

Arg Glu Pro Pro Leu His Met Glu Pro Ile Ser Lys Lys Pro Pro Leu
                805                 810                 815

Arg Lys Asp Lys Lys Glu Lys Ser Asn Met Gln Ser Glu Arg Ala Arg
            820                 825                 830

Lys Glu Gln Val Leu Ile Glu Val Gly Leu Val Pro Val Lys Asp Ser
        835                 840                 845

Trp Leu Leu Lys Glu Ser Val Ser Thr Glu Asp Leu Ser Pro Pro Ser
    850                 855                 860

Pro Pro Leu Pro Lys Glu Asn Leu Arg Glu Glu Ala Ser Gly Asp Gln
865                 870                 875                 880

Lys Leu Leu Asn Thr Gly Glu Gly Asn Lys Glu Ala Pro Leu Gln Lys
                885                 890                 895

Val Gly Ala Glu Glu Ala Asp Glu Ser Leu Pro Gly Leu Ala Ala Asn
            900                 905                 910

Ile Asn Glu Ser Thr His Ile Ser Ser Ser Gly Gln Asn Leu Asn Thr
        915                 920                 925

Pro Glu Gly Glu Thr Leu Asn Gly Lys His Gln Thr Asp Ser Ile Val
    930                 935                 940

Cys Glu Met Lys Met Asp Thr Asp Gln Asn Thr Arg Glu Asn Leu Thr
945                 950                 955                 960

Gly Ile Asn Ser Thr Val Glu Glu Pro Val Ser Pro Met Leu Pro Pro
                965                 970                 975

Ser Ala Val Glu Glu Arg Glu Ala Val Ser Lys Thr Ala Leu Ala Ser
            980                 985                 990

Pro Pro Ala Thr Met Ala Ala Asn  Glu Ser Gln Glu Ile  Asp Glu Asp
        995                 1000                1005

Glu Gly  Ile His Ser His Glu  Gly Ser Asp Leu Ser  Asp Asn Met
    1010                 1015                 1020

Ser Glu  Gly Ser Asp Asp Ser  Gly Leu His Gly Ala  Arg Pro Val
    1025                 1030                 1035

Pro Gln  Glu Ser Ser Arg Lys  Asn Ala Lys Glu Ala  Leu Ala Val
    1040                 1045                 1050

Lys Ala  Ala Lys Gly Asp Phe  Val Cys Ile Phe Cys  Asp Arg Ser
    1055                 1060                 1065

Phe Arg  Lys Gly Lys Asp Tyr  Ser Lys His Leu Asn  Arg His Leu
    1070                 1075                 1080

Val Asn  Val Tyr Tyr Leu Glu  Glu Ala Ala Gln Gly  Gln Glu
    1085                 1090                 1095
```

<210> SEQ ID NO 2
<211> LENGTH: 3294
<212> TYPE: DNA
<213> ORGANISM: Homo sapiens

<400> SEQUENCE: 2

```
atggccaccc aggtaatggg gcagtcttct ggaggaggag ggctgtttac cagcagtggc     60

aacattggaa tggccctgcc taacgacatg tatgacttgc atgacctttc caaagctgaa    120

ctggccgcac ctcagcttat tatgctggca aatgtggcct taactgggga agtaaatggc    180

agctgctgtg attacctggt cggtgaagaa agacagatgg cagaactgat gccggttggg    240

gataacaact tttcagatag tgaagaagga gaaggacttg aagagtctgc tgatataaaa    300
```

-continued

```
ggtgaacctc atggactgga aaacatggaa ctgagaagtt tggaactcag cgtcgtagaa    360
cctcagcctg tatttgaggc atcaggtgct ccagatattt acagttcaaa taaagatctt    420
ccccctgaaa cacctggagc ggaggacaaa ggcaagagct cgaagaccaa accctttcgc    480
tgtaagccat gccaatatga agcagaatct gaagaacagt ttgtgcatca catcagagtt    540
cacagtgcta agaaattttt tgtggaagag agtgcagaga agcaggcaaa agccagggaa    600
tctggctctt ccactgcaga agagggagat ttctccaagg gccccattcg ctgtgaccgc    660
tgcggctaca atactaatcg atatgatcac tatacagcac acctgaaaca ccacaccaga    720
gctggggata atgagcgagt ctacaagtgt atcatttgca catacacaac agtgagcgag    780
tatcactgga ggaaacattt aagaaaccat tttccaagga aagtatacac atgtggaaaa    840
tgcaactatt tttcagacag aaaaaacaat tatgttcagc atgttagaac tcatacagga    900
gaacgcccat ataaatgtga actttgtcct tactcaagtt ctcagaagac tcatctaact    960
agacatatgc gtactcattc aggtgagaag ccatttaaat gtgatcagtg cagttatgtg   1020
gcctctaatc aacatgaagt aacccgccat gcaagacagg ttcacaatgg gcctaaacct   1080
cttaattgcc cacactgtga ttacaaaaca gcagatagaa gcaacttcaa aaaacatgta   1140
gagctacatg tgaacccacg gcagttcaat tgccctgtat gtgactatgc agcttccaag   1200
aagtgtaatc tacagtatca cttcaaatct aagcatccta cttgtcctaa taaaacaatg   1260
gatgtctcaa aagtgaaact aaagaaaacc aaaaaacgag aggctgactt gcctgataat   1320
attaccaatg aaaaaacaga aatagaacaa acaaaaataa aaggggatgt ggctggaaag   1380
aaaaatgaaa agtccgtcaa agcagagaaa agagatgtct caaaagagaa aaagccttct   1440
aataatgtgt cagtgatcca ggtgactacc agaactcgaa aatcagtaac agaggtgaaa   1500
gagatggatg tgcatacagg aagcaattca gaaaaattca gtaaaactaa gaaaagcaaa   1560
aggaagctgg aagttgacag ccattcttta catggtcctg tgaatgatga ggaatcttca   1620
acaaaaaaga aaaagaaggt agaaagcaaa tccaaaaata atagtcagga agtgccaaag   1680
ggtgacagca aagtggagga gaataaaaag caaaatactt gcatgaaaaa aagtacaaag   1740
aagaaaactc tgaaaaataa atcaagtaag aaaagcagta agcctcctca gaaggaacct   1800
gttgagaagg gatctgctca gatggaccct cctcagatgg ggcctgctcc cacagaggcg   1860
gttcagaagg ggcccgttca ggtggagccg ccacctccca tggagcatgc tcagatggag   1920
ggtgcccaga tacggcctgc tcctgacgag cctgttcaga tggaggtggt tcaggagggg   1980
cctgctcaga aggagctgct gcctcccgtg gagcctgctc agatggtggg tgcccaaatt   2040
gtacttgctc acatggagct gcctcctccc atggagactg ctcagacgga ggttgcccaa   2100
atggggcctg ctcccatgga acctgctcag atggaggttg cccaggtaga atctgctccc   2160
atgcaggtgg tccagaagga gcctgttcag atggagctgt ctcctcccat ggaggtggtc   2220
cagaaggagc ctgttcagat agagctgtct cctcccatgg aggtggtcca gaaggaacct   2280
gttaagatag agctgtctcc tcccatagag gtggtccaga aggagcctgt tcagatggag   2340
ttgtctcctc ccatgggggt ggttcagaag gagcctgctc agagggagcc acctcctccc   2400
agagagcctc cccttcacat ggagccaatt tccaaaaagc ctcctctccg aaaagataaa   2460
aaggaaaagt ctaacatgca gagtgaaagg gcacggaagg agcaagtcct tattgaagtt   2520
ggcttagtgc ctgttaaaga tagctggctt ctaaaggaaa gtgtaagcac agaggatctc   2580
tcaccaccat caccaccact gccaaaggaa aatttaagag aagaggcatc aggagaccaa   2640
aaattactca acacaggtga aggaaataaa gaagcccctc ttcagaaagt aggagcagaa   2700
```

```
gaggcagatg agagcctacc tggtcttgct gctaatatca acgaatctac ccatatttca   2760

tcctctggac aaaacttgaa tacgccagag ggtgaaactt taaatggtaa acatcagact   2820

gacagtatag tttgtgaaat gaaaatggac actgatcaga acacaagaga gaatctcact   2880

ggtataaatt caacagttga agaaccagtt tcaccaatgc ttcccccttc agcagtagaa   2940

gaacgtgaag cagtgtccaa aactgcactg gcatcacctc ctgctacaat ggcagcaaat   3000

gagtctcagg aaattgatga agatgaaggc atccacagcc atgaaggaag tgacctaagt   3060

gacaacatgt cagagggtag tgatgattct ggattgcatg gggctcggcc agttccacaa   3120

gaatctagca gaaaaaatgc aaaggaagcc ttggcagtca aagcggctaa gggagatttt   3180

gtttgtatct tctgtgatcg ttctttcaga aagggaaaag attacagcaa acacctcaat   3240

cgccatttgg ttaatgtgta ctatcttgaa gaagcagctc aagggcagga gtaa         3294


<210> SEQ ID NO 3
<211> LENGTH: 237
<212> TYPE: DNA
<213> ORGANISM: Homo sapiens

<400> SEQUENCE: 3

caattatgtt cagcatgtta gaactcatac aggagaacgc ccatataaat gtgaactttg     60

tccttactca agttctcaga agactcatct aactagacat atgcgtactc attcaggtga    120

gaagccattt aaatgtgatc agtgcagtta tgtggcctct aatcaacatg aagtaacccg    180

ccatgcaaga caggttcaca atgggcctaa acctcttaat tgcccacact gtgatta       237


<210> SEQ ID NO 4
<211> LENGTH: 30
<212> TYPE: RNA
<213> ORGANISM: Artificial Sequence
<220> FEATURE:
<223> OTHER INFORMATION: gRNA

<400> SEQUENCE: 4

agcucgugca ggucguacau gucguugguu                                      30


<210> SEQ ID NO 5
<211> LENGTH: 31
<212> TYPE: RNA
<213> ORGANISM: Artificial Sequence
<220> FEATURE:
<223> OTHER INFORMATION: gRNA

<400> SEQUENCE: 5

cgcuguauau uucuggggca gcugaggcuu c                                    31


<210> SEQ ID NO 6
<211> LENGTH: 31
<212> TYPE: RNA
<213> ORGANISM: Artificial Sequence
<220> FEATURE:
<223> OTHER INFORMATION: gRNA

<400> SEQUENCE: 6

cuuuggccug uuucucugca cuuuccucca c                                    31


<210> SEQ ID NO 7
<211> LENGTH: 30
<212> TYPE: RNA
<213> ORGANISM: Artificial Sequence
<220> FEATURE:
```

<223> OTHER INFORMATION: gRNA

<400> SEQUENCE: 7
cacuugcugc agguguagac uuuccugggg 30

<210> SEQ ID NO 8
<211> LENGTH: 30
<212> TYPE: RNA
<213> ORGANISM: Artificial Sequence
<220> FEATURE:
<223> OTHER INFORMATION: gRNA

<400> SEQUENCE: 8
gcguucuccu gugugaguuc gcacgugcug 30

<210> SEQ ID NO 9
<211> LENGTH: 30
<212> TYPE: RNA
<213> ORGANISM: Artificial Sequence
<220> FEATURE:
<223> OTHER INFORMATION: gRNA

<400> SEQUENCE: 9
gaugagucuu cugagagcuu gaguaaggac 30

<210> SEQ ID NO 10
<211> LENGTH: 28
<212> TYPE: RNA
<213> ORGANISM: Artificial Sequence
<220> FEATURE:
<223> OTHER INFORMATION: gRNA

<400> SEQUENCE: 10
gucacuucau gcugauuaga ggccacau 28

<210> SEQ ID NO 11
<211> LENGTH: 30
<212> TYPE: RNA
<213> ORGANISM: Artificial Sequence
<220> FEATURE:
<223> OTHER INFORMATION: gRNA

<400> SEQUENCE: 11
cgggcaauua agagguuuag gcccguugug 30

<210> SEQ ID NO 12
<211> LENGTH: 32
<212> TYPE: RNA
<213> ORGANISM: Artificial Sequence
<220> FEATURE:
<223> OTHER INFORMATION: gRNA

<400> SEQUENCE: 12
ucacacacgg ggcaguugaa cugccguggg uu 32

<210> SEQ ID NO 13
<211> LENGTH: 25
<212> TYPE: RNA
<213> ORGANISM: Artificial Sequence
<220> FEATURE:
<223> OTHER INFORMATION: gRNA

<400> SEQUENCE: 13
ugguauugua gauuacacuu cuuag 25

<210> SEQ ID NO 14
<211> LENGTH: 27
<212> TYPE: RNA
<213> ORGANISM: Artificial Sequence
<220> FEATURE:
<223> OTHER INFORMATION: gRNA

<400> SEQUENCE: 14
cugggacagg ugggaugcuu agauuug 27

<210> SEQ ID NO 15
<211> LENGTH: 25
<212> TYPE: RNA
<213> ORGANISM: Artificial Sequence
<220> FEATURE:
<223> OTHER INFORMATION: gRNA

<400> SEQUENCE: 15
ucuucucguu gcugacggcg uuauu 25

<210> SEQ ID NO 16
<211> LENGTH: 30
<212> TYPE: RNA
<213> ORGANISM: Artificial Sequence
<220> FEATURE:
<223> OTHER INFORMATION: gRNA

<400> SEQUENCE: 16
gcggcgucuu cuuugugccu uucuuaaggg 30

<210> SEQ ID NO 17
<211> LENGTH: 30
<212> TYPE: RNA
<213> ORGANISM: Artificial Sequence
<220> FEATURE:
<223> OTHER INFORMATION: gRNA

<400> SEQUENCE: 17
agaagauccu gacccgguga ccucugccug 30

<210> SEQ ID NO 18
<211> LENGTH: 30
<212> TYPE: RNA
<213> ORGANISM: Artificial Sequence
<220> FEATURE:
<223> OTHER INFORMATION: gRNA

<400> SEQUENCE: 18
gcuccauacu gggagguggu uccuucuggg 30

<210> SEQ ID NO 19
<211> LENGTH: 30
<212> TYPE: RNA
<213> ORGANISM: Artificial Sequence
<220> FEATURE:
<223> OTHER INFORMATION: gRNA

<400> SEQUENCE: 19
aagcuugcug ucucuaacag gcaccaagcc 30

<210> SEQ ID NO 20
<211> LENGTH: 29
<212> TYPE: RNA
<213> ORGANISM: Artificial Sequence
<220> FEATURE:
<223> OTHER INFORMATION: gRNA

<400> SEQUENCE: 20
aucugucuuc ugcucagugu ccacgucac 29

<210> SEQ ID NO 21
<211> LENGTH: 30
<212> TYPE: DNA
<213> ORGANISM: Mus musculus

<400> SEQUENCE: 21
aaccaacgac atgtacgacc tgcacgagct 30

<210> SEQ ID NO 22
<211> LENGTH: 31
<212> TYPE: DNA
<213> ORGANISM: Mus musculus

<400> SEQUENCE: 22
gaagcctcag ctgccccaga aatatacagc g 31

<210> SEQ ID NO 23
<211> LENGTH: 31
<212> TYPE: DNA
<213> ORGANISM: Mus musculus

<400> SEQUENCE: 23
gtggaggaaa gtgcagagaa acaggccaaa g 31

<210> SEQ ID NO 24
<211> LENGTH: 30
<212> TYPE: DNA
<213> ORGANISM: Mus musculus

<400> SEQUENCE: 24
ccccaggaaa gtctacacct gcagcaagtg 30

<210> SEQ ID NO 25
<211> LENGTH: 30
<212> TYPE: DNA
<213> ORGANISM: Mus musculus

<400> SEQUENCE: 25
cagcacgtgc gaactcacac aggagaacgc 30

<210> SEQ ID NO 26
<211> LENGTH: 30
<212> TYPE: DNA
<213> ORGANISM: Mus musculus

<400> SEQUENCE: 26
gtccttactc aagctctcag aagactcatc 30

<210> SEQ ID NO 27
<211> LENGTH: 28
<212> TYPE: DNA
<213> ORGANISM: Mus musculus

<400> SEQUENCE: 27
atgtggcctc taatcagcat gaagtgac 28

<210> SEQ ID NO 28
<211> LENGTH: 30
<212> TYPE: DNA
<213> ORGANISM: Mus musculus

<400> SEQUENCE: 28
cacaacgggc ctaaacctct taattgcccg 30

<210> SEQ ID NO 29
<211> LENGTH: 32
<212> TYPE: DNA
<213> ORGANISM: Mus musculus

<400> SEQUENCE: 29
aacccacggc agttcaactg ccccgtgtgt ga 32

<210> SEQ ID NO 30
<211> LENGTH: 25
<212> TYPE: DNA
<213> ORGANISM: Mus musculus

<400> SEQUENCE: 30
ctaagaagtg taatctacaa tacca 25

<210> SEQ ID NO 31
<211> LENGTH: 27
<212> TYPE: DNA
<213> ORGANISM: Mus musculus

<400> SEQUENCE: 31
caaatctaag catcccacct gtcccag 27

<210> SEQ ID NO 32
<211> LENGTH: 25
<212> TYPE: DNA
<213> ORGANISM: Mus musculus

<400> SEQUENCE: 32
aataacgccg tcagcaacga gaaga 25

<210> SEQ ID NO 33
<211> LENGTH: 30
<212> TYPE: DNA
<213> ORGANISM: Mus musculus

<400> SEQUENCE: 33
cccttaagaa aggcacaaag aagacgccgc 30

<210> SEQ ID NO 34
<211> LENGTH: 30
<212> TYPE: DNA
<213> ORGANISM: Mus musculus

<400> SEQUENCE: 34
caggcagagg tcaccgggtc aggatcttct 30

<210> SEQ ID NO 35
<211> LENGTH: 30
<212> TYPE: DNA
<213> ORGANISM: Mus musculus

<400> SEQUENCE: 35
cccagaagga accacctccc agtatggagc 30

<210> SEQ ID NO 36
<211> LENGTH: 30
<212> TYPE: DNA

<213> ORGANISM: Mus musculus

<400> SEQUENCE: 36
ggcttggtgc ctgttagaga cagcaagctt 30

<210> SEQ ID NO 37
<211> LENGTH: 29
<212> TYPE: DNA
<213> ORGANISM: Mus musculus

<400> SEQUENCE: 37
gtgacgtgga cactgagcag aagacagat 29

<210> SEQ ID NO 38
<211> LENGTH: 30
<212> TYPE: RNA
<213> ORGANISM: Mus musculus

<400> SEQUENCE: 38
aaccaacgac auguacgacc ugcacgagcu 30

<210> SEQ ID NO 39
<211> LENGTH: 31
<212> TYPE: RNA
<213> ORGANISM: Mus musculus

<400> SEQUENCE: 39
gaagccucag cugccccaga aauauacagc g 31

<210> SEQ ID NO 40
<211> LENGTH: 31
<212> TYPE: RNA
<213> ORGANISM: Mus musculus

<400> SEQUENCE: 40
guggaggaaa gugcagagaa acaggccaaa g 31

<210> SEQ ID NO 41
<211> LENGTH: 30
<212> TYPE: RNA
<213> ORGANISM: Mus musculus

<400> SEQUENCE: 41
ccccaggaaa gucuacaccu gcagcaagug 30

<210> SEQ ID NO 42
<211> LENGTH: 30
<212> TYPE: RNA
<213> ORGANISM: Mus musculus

<400> SEQUENCE: 42
cagcacgugc gaacucacac aggagaacgc 30

<210> SEQ ID NO 43
<211> LENGTH: 30
<212> TYPE: RNA
<213> ORGANISM: Mus musculus

<400> SEQUENCE: 43
guccuuacuc aagcucucag aagacucauc 30

<210> SEQ ID NO 44
<211> LENGTH: 28

<212> TYPE: RNA
<213> ORGANISM: Mus musculus

<400> SEQUENCE: 44
auguggccuc uaaucagcau gaagugac 28

<210> SEQ ID NO 45
<211> LENGTH: 30
<212> TYPE: RNA
<213> ORGANISM: Mus musculus

<400> SEQUENCE: 45
cacaacgggc cuaaaccucu uaauugcccg 30

<210> SEQ ID NO 46
<211> LENGTH: 32
<212> TYPE: RNA
<213> ORGANISM: Mus musculus

<400> SEQUENCE: 46
aacccacggc aguucaacug ccccgugugu ga 32

<210> SEQ ID NO 47
<211> LENGTH: 25
<212> TYPE: RNA
<213> ORGANISM: Mus musculus

<400> SEQUENCE: 47
cuaagaagug uaaucuacaa uacca 25

<210> SEQ ID NO 48
<211> LENGTH: 27
<212> TYPE: RNA
<213> ORGANISM: Mus musculus

<400> SEQUENCE: 48
caaaucuaag caucccaccu gucccag 27

<210> SEQ ID NO 49
<211> LENGTH: 25
<212> TYPE: RNA
<213> ORGANISM: Mus musculus

<400> SEQUENCE: 49
aauaacgccg ucagcaacga gaaga 25

<210> SEQ ID NO 50
<211> LENGTH: 30
<212> TYPE: RNA
<213> ORGANISM: Mus musculus

<400> SEQUENCE: 50
cccuuaagaa aggcacaaag aagacgccgc 30

<210> SEQ ID NO 51
<211> LENGTH: 30
<212> TYPE: RNA
<213> ORGANISM: Mus musculus

<400> SEQUENCE: 51
caggcagagg ucaccggguc aggaucuucu 30

<210> SEQ ID NO 52

<211> LENGTH: 30
<212> TYPE: RNA
<213> ORGANISM: Mus musculus

<400> SEQUENCE: 52
cccagaagga accaccuccc aguauggagc 30

<210> SEQ ID NO 53
<211> LENGTH: 30
<212> TYPE: RNA
<213> ORGANISM: Mus musculus

<400> SEQUENCE: 53
ggcuuggugc cuguuagaga cagcaagcuu 30

<210> SEQ ID NO 54
<211> LENGTH: 29
<212> TYPE: RNA
<213> ORGANISM: Mus musculus

<400> SEQUENCE: 54
gugacgugga cacugagcag aagacagau 29

<210> SEQ ID NO 55
<211> LENGTH: 20
<212> TYPE: DNA
<213> ORGANISM: Artificial Sequence
<220> FEATURE:
<223> OTHER INFORMATION: gRNA

<400> SEQUENCE: 55
ggcgcagcag cagaagaccg 20

<210> SEQ ID NO 56
<211> LENGTH: 20
<212> TYPE: DNA
<213> ORGANISM: Artificial Sequence
<220> FEATURE:
<223> OTHER INFORMATION: gRNA

<400> SEQUENCE: 56
accgcagcga cggcagaacc 20

<210> SEQ ID NO 57
<211> LENGTH: 20
<212> TYPE: DNA
<213> ORGANISM: Artificial Sequence
<220> FEATURE:
<223> OTHER INFORMATION: gRNA

<400> SEQUENCE: 57
ccctggttct gccgtcgctg 20

<210> SEQ ID NO 58
<211> LENGTH: 20
<212> TYPE: DNA
<213> ORGANISM: Artificial Sequence
<220> FEATURE:
<223> OTHER INFORMATION: gRNA

<400> SEQUENCE: 58
agcgacggca gaaccagggc 20

<210> SEQ ID NO 59
<211> LENGTH: 20

<212> TYPE: DNA
<213> ORGANISM: Artificial Sequence
<220> FEATURE:
<223> OTHER INFORMATION: gRNA

<400> SEQUENCE: 59
cgggatcaga ccgccggccc 20

<210> SEQ ID NO 60
<211> LENGTH: 20
<212> TYPE: DNA
<213> ORGANISM: Artificial Sequence
<220> FEATURE:
<223> OTHER INFORMATION: gRNA

<400> SEQUENCE: 60
gatcgcaccc cgggatctcg 20

<210> SEQ ID NO 61
<211> LENGTH: 20
<212> TYPE: DNA
<213> ORGANISM: Artificial Sequence
<220> FEATURE:
<223> OTHER INFORMATION: gRNA

<400> SEQUENCE: 61
gagttggagc ggcggcgacg 20

<210> SEQ ID NO 62
<211> LENGTH: 20
<212> TYPE: DNA
<213> ORGANISM: Artificial Sequence
<220> FEATURE:
<223> OTHER INFORMATION: gRNA

<400> SEQUENCE: 62
atactgtggc tcgggcggcg 20

<210> SEQ ID NO 63
<211> LENGTH: 20
<212> TYPE: DNA
<213> ORGANISM: Mus musculus

<400> SEQUENCE: 63
ggcgcagcag cagaagaccg 20

<210> SEQ ID NO 64
<211> LENGTH: 20
<212> TYPE: DNA
<213> ORGANISM: Mus musculus

<400> SEQUENCE: 64
accgcagcga cggcagaacc 20

<210> SEQ ID NO 65
<211> LENGTH: 20
<212> TYPE: DNA
<213> ORGANISM: Mus musculus

<400> SEQUENCE: 65
ccctggttct gccgtcgctg 20

<210> SEQ ID NO 66
<211> LENGTH: 20
<212> TYPE: DNA

<213> ORGANISM: Mus musculus

<400> SEQUENCE: 66
agcgacggca gaaccagggc 20

<210> SEQ ID NO 67
<211> LENGTH: 20
<212> TYPE: DNA
<213> ORGANISM: Mus musculus

<400> SEQUENCE: 67
cgggatcaga ccgccggccc 20

<210> SEQ ID NO 68
<211> LENGTH: 20
<212> TYPE: DNA
<213> ORGANISM: Mus musculus

<400> SEQUENCE: 68
gatcgcaccc cgggatctcg 20

<210> SEQ ID NO 69
<211> LENGTH: 20
<212> TYPE: DNA
<213> ORGANISM: Mus musculus

<400> SEQUENCE: 69
gagttggagc ggcggcgacg 20

<210> SEQ ID NO 70
<211> LENGTH: 20
<212> TYPE: DNA
<213> ORGANISM: Mus musculus

<400> SEQUENCE: 70
atactgtggc tcgggcggcg 20

<210> SEQ ID NO 71
<211> LENGTH: 21
<212> TYPE: DNA
<213> ORGANISM: Artificial Sequence
<220> FEATURE:
<223> OTHER INFORMATION: gRNA

<400> SEQUENCE: 71
ggcgggcggc gacggcgcgg g 21

<210> SEQ ID NO 72
<211> LENGTH: 21
<212> TYPE: DNA
<213> ORGANISM: Artificial Sequence
<220> FEATURE:
<223> OTHER INFORMATION: gRNA

<400> SEQUENCE: 72
gcgcggcgca gcgtcctgtg c 21

<210> SEQ ID NO 73
<211> LENGTH: 21
<212> TYPE: DNA
<213> ORGANISM: Artificial Sequence
<220> FEATURE:
<223> OTHER INFORMATION: gRNA

<400> SEQUENCE: 73
agcgacggca gaaccagggc c 21

<210> SEQ ID NO 74
<211> LENGTH: 21
<212> TYPE: DNA
<213> ORGANISM: Artificial Sequence
<220> FEATURE:
<223> OTHER INFORMATION: gRNA

<400> SEQUENCE: 74
cggccctggt tctgccgtcg c 21

<210> SEQ ID NO 75
<211> LENGTH: 21
<212> TYPE: DNA
<213> ORGANISM: Artificial Sequence
<220> FEATURE:
<223> OTHER INFORMATION: gRNA

<400> SEQUENCE: 75
ggaccgtggg cgcacagttc a 21

<210> SEQ ID NO 76
<211> LENGTH: 21
<212> TYPE: DNA
<213> ORGANISM: Artificial Sequence
<220> FEATURE:
<223> OTHER INFORMATION: gRNA

<400> SEQUENCE: 76
cggccgccgc gccgcccgag c 21

<210> SEQ ID NO 77
<211> LENGTH: 21
<212> TYPE: DNA
<213> ORGANISM: Mus musculus

<400> SEQUENCE: 77
ggcgggcggc gacggcgcgg g 21

<210> SEQ ID NO 78
<211> LENGTH: 21
<212> TYPE: DNA
<213> ORGANISM: Mus musculus

<400> SEQUENCE: 78
gcgcggcgca gcgtcctgtg c 21

<210> SEQ ID NO 79
<211> LENGTH: 21
<212> TYPE: DNA
<213> ORGANISM: Mus musculus

<400> SEQUENCE: 79
agcgacggca gaaccagggc c 21

<210> SEQ ID NO 80
<211> LENGTH: 21
<212> TYPE: DNA
<213> ORGANISM: Mus musculus

<400> SEQUENCE: 80
cggccctggt tctgccgtcg c 21

<210> SEQ ID NO 81
<211> LENGTH: 21
<212> TYPE: DNA
<213> ORGANISM: Mus musculus

<400> SEQUENCE: 81
ggaccgtggg cgcacagttc a 21

<210> SEQ ID NO 82
<211> LENGTH: 21
<212> TYPE: DNA
<213> ORGANISM: Mus musculus

<400> SEQUENCE: 82
cggccgccgc gccgcccgag c 21

<210> SEQ ID NO 83
<211> LENGTH: 30
<212> TYPE: RNA
<213> ORGANISM: Artificial Sequence
<220> FEATURE:
<223> OTHER INFORMATION: gRNA

<400> SEQUENCE: 83
uaagcugagg ugcggccagu ucagcuuugg 30

<210> SEQ ID NO 84
<211> LENGTH: 30
<212> TYPE: RNA
<213> ORGANISM: Artificial Sequence
<220> FEATURE:
<223> OTHER INFORMATION: gRNA

<400> SEQUENCE: 84
ucacagcagc ugccauuuac uuccccaguu 30

<210> SEQ ID NO 85
<211> LENGTH: 27
<212> TYPE: RNA
<213> ORGANISM: Artificial Sequence
<220> FEATURE:
<223> OTHER INFORMATION: gRNA

<400> SEQUENCE: 85
ccaucugucu uucuucaccg accaggu 27

<210> SEQ ID NO 86
<211> LENGTH: 29
<212> TYPE: RNA
<213> ORGANISM: Artificial Sequence
<220> FEATURE:
<223> OTHER INFORMATION: gRNA

<400> SEQUENCE: 86
cuguaaauau cuggagcacc ugaugccuc 29

<210> SEQ ID NO 87
<211> LENGTH: 30
<212> TYPE: RNA
<213> ORGANISM: Artificial Sequence
<220> FEATURE:

<223> OTHER INFORMATION: gRNA

<400> SEQUENCE: 87
uucugcuuca uauuggcaug gcuuacagcg 30

<210> SEQ ID NO 88
<211> LENGTH: 30
<212> TYPE: RNA
<213> ORGANISM: Artificial Sequence
<220> FEATURE:
<223> OTHER INFORMATION: gRNA

<400> SEQUENCE: 88
cuuagcacug ugaacucuga ugugaugcac 30

<210> SEQ ID NO 89
<211> LENGTH: 28
<212> TYPE: RNA
<213> ORGANISM: Artificial Sequence
<220> FEATURE:
<223> OTHER INFORMATION: gRNA

<400> SEQUENCE: 89
uugccugcuu cucugcacuc ucuuccac 28

<210> SEQ ID NO 90
<211> LENGTH: 30
<212> TYPE: RNA
<213> ORGANISM: Artificial Sequence
<220> FEATURE:
<223> OTHER INFORMATION: gRNA

<400> SEQUENCE: 90
cagcggucac agcgaauggg gcccuuggag 30

<210> SEQ ID NO 91
<211> LENGTH: 31
<212> TYPE: RNA
<213> ORGANISM: Artificial Sequence
<220> FEATURE:
<223> OTHER INFORMATION: gRNA

<400> SEQUENCE: 91
cucauuaucc ccagcucugg ugugguguuu c 31

<210> SEQ ID NO 92
<211> LENGTH: 28
<212> TYPE: RNA
<213> ORGANISM: Artificial Sequence
<220> FEATURE:
<223> OTHER INFORMATION: gRNA

<400> SEQUENCE: 92
ugauacucgc ucacuguugu guaugugc 28

<210> SEQ ID NO 93
<211> LENGTH: 29
<212> TYPE: RNA
<213> ORGANISM: Artificial Sequence
<220> FEATURE:
<223> OTHER INFORMATION: gRNA

<400> SEQUENCE: 93
cguucuccug uaugaguucu aacaugcug 29

<210> SEQ ID NO 94
<211> LENGTH: 29
<212> TYPE: RNA
<213> ORGANISM: Artificial Sequence
<220> FEATURE:
<223> OTHER INFORMATION: gRNA

<400> SEQUENCE: 94
augagucuuc ugagaacuug aguaaggac 29

<210> SEQ ID NO 95
<211> LENGTH: 32
<212> TYPE: RNA
<213> ORGANISM: Artificial Sequence
<220> FEATURE:
<223> OTHER INFORMATION: gRNA

<400> SEQUENCE: 95
ucuaguuaga ugagucuucu gagaacuuga gu 32

<210> SEQ ID NO 96
<211> LENGTH: 29
<212> TYPE: RNA
<213> ORGANISM: Artificial Sequence
<220> FEATURE:
<223> OTHER INFORMATION: gRNA

<400> SEQUENCE: 96
cauaugucua guuagaugag ucuucugag 29

<210> SEQ ID NO 97
<211> LENGTH: 28
<212> TYPE: RNA
<213> ORGANISM: Artificial Sequence
<220> FEATURE:
<223> OTHER INFORMATION: gRNA

<400> SEQUENCE: 97
aaugaguacg cauaugucua guuagaug 28

<210> SEQ ID NO 98
<211> LENGTH: 30
<212> TYPE: RNA
<213> ORGANISM: Artificial Sequence
<220> FEATURE:
<223> OTHER INFORMATION: gRNA

<400> SEQUENCE: 98
cuucucaccu gaaugaguac gcauaugucu 30

<210> SEQ ID NO 99
<211> LENGTH: 31
<212> TYPE: RNA
<213> ORGANISM: Artificial Sequence
<220> FEATURE:
<223> OTHER INFORMATION: gRNA

<400> SEQUENCE: 99
cacugaucac auuuaaaugg cuucucaccu g 31

<210> SEQ ID NO 100
<211> LENGTH: 28
<212> TYPE: RNA
<213> ORGANISM: Artificial Sequence
<220> FEATURE:
<223> OTHER INFORMATION: gRNA

<400> SEQUENCE: 100
aggccacaua acugcacuga ucacauuu 28

<210> SEQ ID NO 101
<211> LENGTH: 28
<212> TYPE: RNA
<213> ORGANISM: Artificial Sequence
<220> FEATURE:
<223> OTHER INFORMATION: gRNA

<400> SEQUENCE: 101
guuacuucau guugauuaga ggccacau 28

<210> SEQ ID NO 102
<211> LENGTH: 31
<212> TYPE: RNA
<213> ORGANISM: Artificial Sequence
<220> FEATURE:
<223> OTHER INFORMATION: gRNA

<400> SEQUENCE: 102
cccauuguga accugucuug cauggcgggu u 31

<210> SEQ ID NO 103
<211> LENGTH: 30
<212> TYPE: RNA
<213> ORGANISM: Artificial Sequence
<220> FEATURE:
<223> OTHER INFORMATION: gRNA

<400> SEQUENCE: 103
ugggcaauua agagguuuag gcccauugug 30

<210> SEQ ID NO 104
<211> LENGTH: 29
<212> TYPE: RNA
<213> ORGANISM: Artificial Sequence
<220> FEATURE:
<223> OTHER INFORMATION: gRNA

<400> SEQUENCE: 104
uaaucacagu gugggcaauu aagagguuu 29

<210> SEQ ID NO 105
<211> LENGTH: 28
<212> TYPE: RNA
<213> ORGANISM: Artificial Sequence
<220> FEATURE:
<223> OTHER INFORMATION: gRNA

<400> SEQUENCE: 105
auuaggacaa guaggaugcu uagauuug 28

<210> SEQ ID NO 106
<211> LENGTH: 29
<212> TYPE: RNA
<213> ORGANISM: Artificial Sequence
<220> FEATURE:
<223> OTHER INFORMATION: gRNA

<400> SEQUENCE: 106
aagauuccuc aucauucaca ggaccaugu 29

<210> SEQ ID NO 107
<211> LENGTH: 30

<212> TYPE: RNA
<213> ORGANISM: Artificial Sequence
<220> FEATURE:
<223> OTHER INFORMATION: gRNA

<400> SEQUENCE: 107
agcaggcccc uccugaacca ccuccaucug 30

<210> SEQ ID NO 108
<211> LENGTH: 30
<212> TYPE: RNA
<213> ORGANISM: Artificial Sequence
<220> FEATURE:
<223> OTHER INFORMATION: gRNA

<400> SEQUENCE: 108
cagcagcucc uucugagcag gccccuccug 30

<210> SEQ ID NO 109
<211> LENGTH: 30
<212> TYPE: RNA
<213> ORGANISM: Artificial Sequence
<220> FEATURE:
<223> OTHER INFORMATION: gRNA

<400> SEQUENCE: 109
auuugggcaa ccuccgucug agcagucucc 30

<210> SEQ ID NO 110
<211> LENGTH: 28
<212> TYPE: RNA
<213> ORGANISM: Artificial Sequence
<220> FEATURE:
<223> OTHER INFORMATION: gRNA

<400> SEQUENCE: 110
ccucuauggg aggagacagc ucuaucuu 28

<210> SEQ ID NO 111
<211> LENGTH: 29
<212> TYPE: RNA
<213> ORGANISM: Artificial Sequence
<220> FEATURE:
<223> OTHER INFORMATION: gRNA

<400> SEQUENCE: 111
cuaucuuuaa caggcacuaa gccaacuuc 29

<210> SEQ ID NO 112
<211> LENGTH: 32
<212> TYPE: RNA
<213> ORGANISM: Artificial Sequence
<220> FEATURE:
<223> OTHER INFORMATION: gRNA

<400> SEQUENCE: 112
cucucaucug ccucuucugc uccuacuuuc ug 32

<210> SEQ ID NO 113
<211> LENGTH: 30
<212> TYPE: RNA
<213> ORGANISM: Artificial Sequence
<220> FEATURE:
<223> OTHER INFORMATION: gRNA

<400> SEQUENCE: 113
ccauuuaaag uuucacccuc uggcguauuc 30

<210> SEQ ID NO 114
<211> LENGTH: 29
<212> TYPE: RNA
<213> ORGANISM: Artificial Sequence
<220> FEATURE:
<223> OTHER INFORMATION: gRNA

<400> SEQUENCE: 114
cuauacuguc agucugaugu uuaccauuu 29

<210> SEQ ID NO 115
<211> LENGTH: 32
<212> TYPE: RNA
<213> ORGANISM: Artificial Sequence
<220> FEATURE:
<223> OTHER INFORMATION: gRNA

<400> SEQUENCE: 115
uucuucuacu gcugaagggg gaagcauugg ug 32

<210> SEQ ID NO 116
<211> LENGTH: 29
<212> TYPE: RNA
<213> ORGANISM: Artificial Sequence
<220> FEATURE:
<223> OTHER INFORMATION: gRNA

<400> SEQUENCE: 116
caggagguga ugccagugca guuuuggac 29

<210> SEQ ID NO 117
<211> LENGTH: 29
<212> TYPE: RNA
<213> ORGANISM: Artificial Sequence
<220> FEATURE:
<223> OTHER INFORMATION: gRNA

<400> SEQUENCE: 117
uggaacuggc cgagccccau gcaauccag 29

<210> SEQ ID NO 118
<211> LENGTH: 29
<212> TYPE: RNA
<213> ORGANISM: Artificial Sequence
<220> FEATURE:
<223> OTHER INFORMATION: gRNA

<400> SEQUENCE: 118
cugaaagaac gaucacagaa gauacaaac 29

<210> SEQ ID NO 119
<211> LENGTH: 25
<212> TYPE: DNA
<213> ORGANISM: Homo sapiens

<400> SEQUENCE: 119
ccaaagcgaa cggccgcacc cagca 25

<210> SEQ ID NO 120
<211> LENGTH: 30
<212> TYPE: DNA

<213> ORGANISM: Homo sapiens

<400> SEQUENCE: 120
aactggggaa gtaaatggca gctgctgtga 30

<210> SEQ ID NO 121
<211> LENGTH: 27
<212> TYPE: DNA
<213> ORGANISM: Homo sapiens

<400> SEQUENCE: 121
acctggtcgg tgaagaaaga cagatgg 27

<210> SEQ ID NO 122
<211> LENGTH: 29
<212> TYPE: DNA
<213> ORGANISM: Homo sapiens

<400> SEQUENCE: 122
gaggcatcag gtgctccaga tatttacag 29

<210> SEQ ID NO 123
<211> LENGTH: 30
<212> TYPE: DNA
<213> ORGANISM: Homo sapiens

<400> SEQUENCE: 123
cgctgtaagc catgccaata tgaagcagaa 30

<210> SEQ ID NO 124
<211> LENGTH: 30
<212> TYPE: DNA
<213> ORGANISM: Homo sapiens

<400> SEQUENCE: 124
gtgcatcaca tcagagttca cagtgctaag 30

<210> SEQ ID NO 125
<211> LENGTH: 28
<212> TYPE: DNA
<213> ORGANISM: Homo sapiens

<400> SEQUENCE: 125
gtggaagaga gtgcagagaa gcaggcaa 28

<210> SEQ ID NO 126
<211> LENGTH: 30
<212> TYPE: DNA
<213> ORGANISM: Homo sapiens

<400> SEQUENCE: 126
ctccaagggc cccattcgct gtgaccgctg 30

<210> SEQ ID NO 127
<211> LENGTH: 31
<212> TYPE: DNA
<213> ORGANISM: Homo sapiens

<400> SEQUENCE: 127
gaaacaccac accagagctg gggataatga g 31

<210> SEQ ID NO 128
<211> LENGTH: 28

<212> TYPE: DNA
<213> ORGANISM: Homo sapiens

<400> SEQUENCE: 128
gcacatacac aacagtgagc gagtatca 28

<210> SEQ ID NO 129
<211> LENGTH: 29
<212> TYPE: DNA
<213> ORGANISM: Homo sapiens

<400> SEQUENCE: 129
cagcatgtta gaactcatac aggagaacg 29

<210> SEQ ID NO 130
<211> LENGTH: 29
<212> TYPE: DNA
<213> ORGANISM: Homo sapiens

<400> SEQUENCE: 130
gtccttactc aagttctcag aagactcat 29

<210> SEQ ID NO 131
<211> LENGTH: 32
<212> TYPE: DNA
<213> ORGANISM: Homo sapiens

<400> SEQUENCE: 131
actcaagttc tcagaagact catctaacta ga 32

<210> SEQ ID NO 132
<211> LENGTH: 29
<212> TYPE: DNA
<213> ORGANISM: Homo sapiens

<400> SEQUENCE: 132
ctcagaagac tcatctaact agacatatg 29

<210> SEQ ID NO 133
<211> LENGTH: 28
<212> TYPE: DNA
<213> ORGANISM: Homo sapiens

<400> SEQUENCE: 133
catctaacta gacatatgcg tactcatt 28

<210> SEQ ID NO 134
<211> LENGTH: 30
<212> TYPE: DNA
<213> ORGANISM: Homo sapiens

<400> SEQUENCE: 134
agacatatgc gtactcattc aggtgagaag 30

<210> SEQ ID NO 135
<211> LENGTH: 31
<212> TYPE: DNA
<213> ORGANISM: Homo sapiens

<400> SEQUENCE: 135
caggtgagaa gccatttaaa tgtgatcagt g 31

<210> SEQ ID NO 136

<211> LENGTH: 28
<212> TYPE: DNA
<213> ORGANISM: Homo sapiens

<400> SEQUENCE: 136
aaatgtgatc agtgcagtta tgtggcct 28

<210> SEQ ID NO 137
<211> LENGTH: 28
<212> TYPE: DNA
<213> ORGANISM: Homo sapiens

<400> SEQUENCE: 137
atgtggcctc taatcaacat gaagtaac 28

<210> SEQ ID NO 138
<211> LENGTH: 31
<212> TYPE: DNA
<213> ORGANISM: Homo sapiens

<400> SEQUENCE: 138
aacccgccat gcaagacagg ttcacaatgg g 31

<210> SEQ ID NO 139
<211> LENGTH: 30
<212> TYPE: DNA
<213> ORGANISM: Homo sapiens

<400> SEQUENCE: 139
cacaatgggc ctaaacctct taattgccca 30

<210> SEQ ID NO 140
<211> LENGTH: 29
<212> TYPE: DNA
<213> ORGANISM: Homo sapiens

<400> SEQUENCE: 140
aaacctctta attgcccaca ctgtgatta 29

<210> SEQ ID NO 141
<211> LENGTH: 28
<212> TYPE: DNA
<213> ORGANISM: Homo sapiens

<400> SEQUENCE: 141
caaatctaag catcctactt gtcctaat 28

<210> SEQ ID NO 142
<211> LENGTH: 29
<212> TYPE: DNA
<213> ORGANISM: Homo sapiens

<400> SEQUENCE: 142
acatggtcct gtgaatgatg aggaatctt 29

<210> SEQ ID NO 143
<211> LENGTH: 30
<212> TYPE: DNA
<213> ORGANISM: Homo sapiens

<400> SEQUENCE: 143
cagatggagg tggttcagga ggggcctgct 30

<210> SEQ ID NO 144
<211> LENGTH: 30
<212> TYPE: DNA
<213> ORGANISM: Homo sapiens

<400> SEQUENCE: 144
caggaggggc ctgctcagaa ggagctgctg 30

<210> SEQ ID NO 145
<211> LENGTH: 30
<212> TYPE: DNA
<213> ORGANISM: Homo sapiens

<400> SEQUENCE: 145
ggagactgct cagacggagg ttgcccaaat 30

<210> SEQ ID NO 146
<211> LENGTH: 28
<212> TYPE: DNA
<213> ORGANISM: Homo sapiens

<400> SEQUENCE: 146
aagatagagc tgtctcctcc catagagg 28

<210> SEQ ID NO 147
<211> LENGTH: 29
<212> TYPE: DNA
<213> ORGANISM: Homo sapiens

<400> SEQUENCE: 147
gaagttggct tagtgcctgt taaagatag 29

<210> SEQ ID NO 148
<211> LENGTH: 32
<212> TYPE: DNA
<213> ORGANISM: Homo sapiens

<400> SEQUENCE: 148
cagaaagtag gagcagaaga ggcagatgag ag 32

<210> SEQ ID NO 149
<211> LENGTH: 30
<212> TYPE: DNA
<213> ORGANISM: Homo sapiens

<400> SEQUENCE: 149
gaatacgcca gagggtgaaa ctttaaatgg 30

<210> SEQ ID NO 150
<211> LENGTH: 29
<212> TYPE: DNA
<213> ORGANISM: Homo sapiens

<400> SEQUENCE: 150
aaatggtaaa catcagactg acagtatag 29

<210> SEQ ID NO 151
<211> LENGTH: 32
<212> TYPE: DNA
<213> ORGANISM: Homo sapiens

<400> SEQUENCE: 151
caccaatgct tccccttca gcagtagaag aa 32

<210> SEQ ID NO 152
<211> LENGTH: 29
<212> TYPE: DNA
<213> ORGANISM: Homo sapiens

<400> SEQUENCE: 152
gtccaaaact gcactggcat cacctcctg 29

<210> SEQ ID NO 153
<211> LENGTH: 29
<212> TYPE: DNA
<213> ORGANISM: Homo sapiens

<400> SEQUENCE: 153
ctggattgca tggggctcgg ccagttcca 29

<210> SEQ ID NO 154
<211> LENGTH: 29
<212> TYPE: DNA
<213> ORGANISM: Homo sapiens

<400> SEQUENCE: 154
gtttgtatct tctgtgatcg ttctttcag 29

<210> SEQ ID NO 155
<211> LENGTH: 30
<212> TYPE: RNA
<213> ORGANISM: Homo sapiens

<400> SEQUENCE: 155
ccaaagcuga acuggccgca ccucagcuua 30

<210> SEQ ID NO 156
<211> LENGTH: 30
<212> TYPE: RNA
<213> ORGANISM: Homo sapiens

<400> SEQUENCE: 156
aacuggggaa guaaauggca gcugcuguga 30

<210> SEQ ID NO 157
<211> LENGTH: 27
<212> TYPE: RNA
<213> ORGANISM: Homo sapiens

<400> SEQUENCE: 157
accuggucgg ugaagaaaga cagaugg 27

<210> SEQ ID NO 158
<211> LENGTH: 29
<212> TYPE: RNA
<213> ORGANISM: Homo sapiens

<400> SEQUENCE: 158
gaggcaucag gugcuccaga uauuuacag 29

<210> SEQ ID NO 159
<211> LENGTH: 30
<212> TYPE: RNA
<213> ORGANISM: Homo sapiens

<400> SEQUENCE: 159
cgcuguaagc caugccaaua ugaagcagaa 30

<210> SEQ ID NO 160
<211> LENGTH: 30
<212> TYPE: RNA
<213> ORGANISM: Homo sapiens

<400> SEQUENCE: 160
gugcaucaca ucagaguuca cagugcuaag 30

<210> SEQ ID NO 161
<211> LENGTH: 28
<212> TYPE: RNA
<213> ORGANISM: Homo sapiens

<400> SEQUENCE: 161
guggaagaga gugcagagaa gcaggcaa 28

<210> SEQ ID NO 162
<211> LENGTH: 30
<212> TYPE: RNA
<213> ORGANISM: Homo sapiens

<400> SEQUENCE: 162
cuccaagggc cccauucgcu gugaccgcug 30

<210> SEQ ID NO 163
<211> LENGTH: 31
<212> TYPE: RNA
<213> ORGANISM: Homo sapiens

<400> SEQUENCE: 163
gaaacaccac accagagcug gggauaauga g 31

<210> SEQ ID NO 164
<211> LENGTH: 28
<212> TYPE: RNA
<213> ORGANISM: Homo sapiens

<400> SEQUENCE: 164
gcacauacac aacagugagc gaguauca 28

<210> SEQ ID NO 165
<211> LENGTH: 29
<212> TYPE: RNA
<213> ORGANISM: Homo sapiens

<400> SEQUENCE: 165
cagcauguua gaacucauac aggagaacg 29

<210> SEQ ID NO 166
<211> LENGTH: 29
<212> TYPE: RNA
<213> ORGANISM: Homo sapiens

<400> SEQUENCE: 166
guccuuacuc aaguucucag aagacucau 29

<210> SEQ ID NO 167
<211> LENGTH: 32
<212> TYPE: RNA
<213> ORGANISM: Homo sapiens

<400> SEQUENCE: 167
acucaaguuc ucagaagacu caucuaacua ga 32

<210> SEQ ID NO 168
<211> LENGTH: 29
<212> TYPE: RNA
<213> ORGANISM: Homo sapiens

<400> SEQUENCE: 168
cucagaagac ucaucuaacu agacauaug 29

<210> SEQ ID NO 169
<211> LENGTH: 28
<212> TYPE: RNA
<213> ORGANISM: Homo sapiens

<400> SEQUENCE: 169
caucuaacua gacauaugcg uacucauu 28

<210> SEQ ID NO 170
<211> LENGTH: 30
<212> TYPE: RNA
<213> ORGANISM: Homo sapiens

<400> SEQUENCE: 170
agacauaugc guacucauuc aggugagaag 30

<210> SEQ ID NO 171
<211> LENGTH: 31
<212> TYPE: RNA
<213> ORGANISM: Homo sapiens

<400> SEQUENCE: 171
caggugagaa gccauuuaaa ugugaucagu g 31

<210> SEQ ID NO 172
<211> LENGTH: 28
<212> TYPE: RNA
<213> ORGANISM: Homo sapiens

<400> SEQUENCE: 172
aaaugugauc agugcaguua uguggccu 28

<210> SEQ ID NO 173
<211> LENGTH: 28
<212> TYPE: RNA
<213> ORGANISM: Homo sapiens

<400> SEQUENCE: 173
auguggccuc uaaucaacau gaaguaac 28

<210> SEQ ID NO 174
<211> LENGTH: 31
<212> TYPE: RNA
<213> ORGANISM: Homo sapiens

<400> SEQUENCE: 174
aacccgccau gcaagacagg uucacaaugg g 31

<210> SEQ ID NO 175
<211> LENGTH: 30
<212> TYPE: RNA

<213> ORGANISM: Homo sapiens

<400> SEQUENCE: 175
cacaaugggc cuaaaccucu uaauugccca 30

<210> SEQ ID NO 176
<211> LENGTH: 29
<212> TYPE: RNA
<213> ORGANISM: Homo sapiens

<400> SEQUENCE: 176
aaaccucuua auugcccaca cugugauua 29

<210> SEQ ID NO 177
<211> LENGTH: 28
<212> TYPE: RNA
<213> ORGANISM: Homo sapiens

<400> SEQUENCE: 177
caaaucuaag cauccuacuu guccuaau 28

<210> SEQ ID NO 178
<211> LENGTH: 29
<212> TYPE: RNA
<213> ORGANISM: Homo sapiens

<400> SEQUENCE: 178 acauggucu gugaaugaug aggaaucuu 29

<210> SEQ ID NO 179
<211> LENGTH: 30
<212> TYPE: RNA
<213> ORGANISM: Homo sapiens

<400> SEQUENCE: 179
cagauggagg ugguucagga ggggccugcu 30

<210> SEQ ID NO 180
<211> LENGTH: 30
<212> TYPE: RNA
<213> ORGANISM: Homo sapiens

<400> SEQUENCE: 180
caggaggggc cugcucagaa ggagcugcug 30

<210> SEQ ID NO 181
<211> LENGTH: 30
<212> TYPE: RNA
<213> ORGANISM: Homo sapiens

<400> SEQUENCE: 181
ggagacugcu cagacggagg uugcccaaau 30

<210> SEQ ID NO 182
<211> LENGTH: 28
<212> TYPE: RNA
<213> ORGANISM: Homo sapiens

<400> SEQUENCE: 182
aagauagagc ugucuccucc cauagagg 28

<210> SEQ ID NO 183
<211> LENGTH: 29

<212> TYPE: RNA
<213> ORGANISM: Homo sapiens

<400> SEQUENCE: 183
gaaguuggcu uagugccugu uaaagauag 29

<210> SEQ ID NO 184
<211> LENGTH: 32
<212> TYPE: RNA
<213> ORGANISM: Homo sapiens

<400> SEQUENCE: 184
cagaaaguag gagcagaaga ggcagaugag ag 32

<210> SEQ ID NO 185
<211> LENGTH: 30
<212> TYPE: RNA
<213> ORGANISM: Homo sapiens

<400> SEQUENCE: 185
gaauacgcca gagggugaaa cuuuaaaugg 30

<210> SEQ ID NO 186
<211> LENGTH: 29
<212> TYPE: RNA
<213> ORGANISM: Homo sapiens

<400> SEQUENCE: 186
aaaugguaaa caucagacug acaguauag 29

<210> SEQ ID NO 187
<211> LENGTH: 32
<212> TYPE: RNA
<213> ORGANISM: Homo sapiens

<400> SEQUENCE: 187
caccaaugcu ucccccuuca gcaguagaag aa 32

<210> SEQ ID NO 188
<211> LENGTH: 29
<212> TYPE: RNA
<213> ORGANISM: Homo sapiens

<400> SEQUENCE: 188
guccaaaacu gcacuggcau caccuccug 29

<210> SEQ ID NO 189
<211> LENGTH: 29
<212> TYPE: RNA
<213> ORGANISM: Homo sapiens

<400> SEQUENCE: 189
cuggauugca uggggcucgg ccaguucca 29

<210> SEQ ID NO 190
<211> LENGTH: 29
<212> TYPE: RNA
<213> ORGANISM: Homo sapiens

<400> SEQUENCE: 190
guuuguaucu ucugugaucg uucuuucag 29

<210> SEQ ID NO 191

<211> LENGTH: 1082
<212> TYPE: PRT
<213> ORGANISM: Mus musculus

<400> SEQUENCE: 191

```
Met Ala Thr Gln Val Met Gly Gln Ser Ser Gly Gly Gly Ser Leu Phe
1               5                   10                  15

Asn Asn Ser Ala Asn Met Gly Met Ala Leu Thr Asn Asp Met Tyr Asp
            20                  25                  30

Leu His Glu Leu Ser Lys Ala Glu Leu Ala Ala Pro Gln Leu Ile Met
        35                  40                  45

Leu Ala Asn Val Ala Leu Thr Gly Glu Ala Ser Gly Ser Cys Cys Asp
    50                  55                  60

Tyr Leu Val Gly Glu Glu Arg Gln Met Ala Glu Leu Met Pro Val Gly
65                  70                  75                  80

Asp Asn His Phe Ser Glu Ser Glu Gly Glu Gly Leu Glu Glu Ser Ala
                85                  90                  95

Asp Leu Lys Gly Leu Glu Asn Met Glu Leu Gly Ser Leu Glu Leu Ser
            100                 105                 110

Ala Val Glu Pro Gln Pro Val Phe Glu Ala Ser Ala Ala Pro Glu Ile
        115                 120                 125

Tyr Ser Ala Asn Lys Asp Pro Ala Pro Glu Thr Pro Val Ala Glu Asp
    130                 135                 140

Lys Cys Arg Ser Ser Lys Ala Lys Pro Phe Arg Cys Lys Pro Cys Gln
145                 150                 155                 160

Tyr Glu Ala Glu Ser Glu Glu Gln Phe Val His His Ile Arg Ile His
                165                 170                 175

Ser Ala Lys Lys Phe Phe Val Glu Glu Ser Ala Glu Lys Gln Ala Lys
            180                 185                 190

Ala Trp Glu Ser Gly Ser Ser Pro Ala Glu Glu Gly Glu Phe Ser Lys
        195                 200                 205

Gly Pro Ile Arg Cys Asp Arg Cys Gly Tyr Asn Thr Asn Arg Tyr Asp
    210                 215                 220

His Tyr Met Ala His Leu Lys His His Leu Arg Ala Gly Glu Asn Glu
225                 230                 235                 240

Arg Ile Tyr Lys Cys Ile Ile Cys Thr Tyr Thr Thr Val Ser Glu Tyr
                245                 250                 255

His Trp Arg Lys His Leu Arg Asn His Phe Pro Arg Lys Val Tyr Thr
            260                 265                 270

Cys Ser Lys Cys Asn Tyr Phe Ser Asp Arg Lys Asn Asn Tyr Val Gln
        275                 280                 285

His Val Arg Thr His Thr Gly Glu Arg Pro Tyr Lys Cys Glu Leu Cys
    290                 295                 300

Pro Tyr Ser Ser Ser Gln Lys Thr His Leu Thr Arg His Met Arg Thr
305                 310                 315                 320

His Ser Gly Glu Lys Pro Phe Lys Cys Asp Gln Cys Asn Tyr Val Ala
                325                 330                 335

Ser Asn Gln His Glu Val Thr Arg His Ala Arg Gln Val His Asn Gly
            340                 345                 350

Pro Lys Pro Leu Asn Cys Pro His Cys Asp Tyr Lys Thr Ala Asp Arg
        355                 360                 365

Ser Asn Phe Lys Lys His Val Glu Leu His Val Asn Pro Arg Gln Phe
    370                 375                 380
```

Asn Cys Pro Val Cys Asp Tyr Ala Ala Ser Lys Lys Cys Asn Leu Gln
385 390 395 400

Tyr His Phe Lys Ser Lys His Pro Thr Cys Pro Ser Lys Thr Met Asp
405 410 415

Val Ser Lys Val Lys Leu Lys Lys Thr Lys Lys Arg Glu Ala Asp Leu
420 425 430

Leu Asn Asn Ala Val Ser Asn Glu Lys Met Glu Asn Glu Gln Thr Lys
435 440 445

Thr Lys Gly Asp Val Ser Gly Lys Lys Asn Glu Lys Pro Val Lys Ala
450 455 460

Val Gly Lys Asp Ala Ser Lys Glu Lys Lys Pro Gly Ser Ser Val Ser
465 470 475 480

Val Val Gln Val Thr Thr Arg Thr Arg Lys Ser Ala Val Ala Ala Glu
485 490 495

Thr Lys Ala Ala Glu Val Lys His Thr Asp Gly Gln Thr Gly Asn Asn
500 505 510

Pro Glu Lys Pro Cys Lys Ala Lys Lys Asn Lys Arg Lys Lys Asp Ala
515 520 525

Glu Ala His Pro Ser Glu Glu Pro Val Asn Glu Gly Pro Val Thr Lys
530 535 540

Lys Lys Lys Lys Ser Glu Cys Lys Ser Lys Ile Gly Thr Asn Val Pro
545 550 555 560

Lys Gly Gly Gly Arg Ala Glu Glu Arg Pro Gly Val Lys Lys Gln Ser
565 570 575

Ala Ser Leu Lys Lys Gly Thr Lys Lys Thr Pro Pro Lys Thr Lys Thr
580 585 590

Ser Lys Lys Gly Gly Lys Leu Ala Pro Lys Gly Met Gly Gln Thr Glu
595 600 605

Pro Ser Ser Gly Ala Leu Ala Gln Val Gly Val Ser Pro Asp Pro Ala
610 615 620

Leu Ile Gln Ala Glu Val Thr Gly Ser Gly Ser Ser Gln Thr Glu Leu
625 630 635 640

Pro Ser Pro Met Asp Ile Ala Lys Ser Glu Pro Ala Gln Met Glu Val
645 650 655

Ser Leu Thr Gly Pro Pro Pro Val Glu Pro Ala Gln Met Glu Pro Ser
660 665 670

Pro Ala Lys Pro Pro Gln Val Glu Ala Pro Thr Tyr Pro Gln Pro Pro
675 680 685

Gln Arg Gly Pro Ala Pro Pro Thr Gly Pro Ala Pro Pro Thr Gly Pro
690 695 700

Ala Pro Pro Thr Glu Pro Ala Pro Pro Thr Gly Leu Ala Glu Met Glu
705 710 715 720

Pro Ser Pro Thr Glu Pro Ser Gln Lys Glu Pro Pro Pro Ser Met Glu
725 730 735

Pro Pro Cys Pro Glu Glu Leu Pro Gln Ala Glu Pro Pro Pro Met Glu
740 745 750

Asp Cys Gln Lys Glu Leu Pro Ser Pro Val Glu Pro Ala Gln Ile Glu
755 760 765

Val Ala Gln Thr Ala Pro Thr Gln Val Gln Glu Glu Pro Pro Pro Val
770 775 780

Ser Glu Pro Pro Arg Val Lys Pro Thr Lys Arg Ser Ser Leu Arg Lys
785 790 795 800

-continued

```
Asp Arg Ala Glu Lys Glu Leu Ser Leu Leu Ser Glu Met Ala Arg Gln
                805                 810                 815

Glu Gln Val Leu Met Gly Val Gly Leu Val Pro Val Arg Asp Ser Lys
            820                 825                 830

Leu Leu Lys Gly Asn Lys Ser Ala Gln Asp Pro Pro Ala Pro Pro Ser
        835                 840                 845

Pro Ser Pro Lys Gly Asn Ser Arg Glu Glu Thr Pro Lys Asp Gln Glu
    850                 855                 860

Met Val Ser Asp Gly Glu Gly Thr Ile Val Phe Pro Leu Lys Lys Gly
865                 870                 875                 880

Gly Pro Glu Glu Ala Gly Glu Ser Pro Ala Glu Leu Ala Ala Leu Lys
                885                 890                 895

Glu Ser Ala Arg Val Ser Ser Ser Glu Gln Asn Ser Ala Met Pro Glu
            900                 905                 910

Gly Gly Ala Ser His Ser Lys Cys Gln Thr Gly Ser Ser Gly Leu Cys
        915                 920                 925

Asp Val Asp Thr Glu Gln Lys Thr Asp Thr Val Pro Met Lys Asp Ser
    930                 935                 940

Ala Ala Glu Pro Val Ser Pro Pro Thr Pro Thr Val Asp Arg Asp Ala
945                 950                 955                 960

Gly Ser Pro Ala Val Val Ala Ser Pro Pro Ile Thr Leu Ala Glu Asn
                965                 970                 975

Glu Ser Gln Glu Ile Asp Glu Asp Glu Gly Ile His Ser His Asp Gly
            980                 985                 990

Ser Asp Leu Ser Asp Asn Met Ser  Glu Gly Ser Asp Asp  Ser Gly Leu
        995                 1000                1005

His Gly  Ala Arg Pro Thr Pro  Pro Glu Ala Thr Ser  Lys Asn Gly
    1010                1015                1020

Lys Ala  Gly Leu Ala Gly Lys  Val Thr Glu Gly Glu  Phe Val Cys
    1025                1030                1035

Ile Phe  Cys Asp Arg Ser Phe  Arg Lys Glu Lys Asp  Tyr Ser Lys
    1040                1045                1050

His Leu  Asn Arg His Leu Val  Asn Val Tyr Phe Leu  Glu Glu Ala
    1055                1060                1065

Ala Glu  Glu Gln Glu Glu Gln  Glu Glu Arg Glu Glu  Gln Glu
    1070                1075                1080
```

<210> SEQ ID NO 192
<211> LENGTH: 3249
<212> TYPE: DNA
<213> ORGANISM: Mus musculus

<400> SEQUENCE: 192

```
atggccaccc aggtgatggg gcagtcttct ggaggaggca gtctcttcaa caacagtgcc      60

aacatgggca tggccttaac caacgacatg tacgacctgc acgagctctc gaaagctgaa     120

ctggcagccc ctcagctcat catgttagcc aacgtggccc tgacggggga ggcaagcggc     180

agctgctgcg attacctggt cggtgaagag aggcagatgg ccgaattgat gcccgtggga     240

gacaaccact tctcagaaag tgaaggagaa ggcctggaag agtcggctga cctcaaaggg     300

ctggaaaaca tggaactggg aagtttggag ctaagtgctg tagaacccca gcccgtattt     360

gaagcctcag ctgccccaga aatatacagc gccaataaag atcccgctcc agaaacaccc     420

gtggcggaag acaaatgcag gagttctaag gccaagccct tccggtgtaa gccttgccag     480

tacgaagccg aatctgaaga gcagtttgtg catcacatcc ggattcacag cgctaagaag     540
```

```
ttctttgtgg aggaaagtgc agagaaacag gccaaagcct gggagtcggg gtcgtctccg    600
gccgaagagg gcgagttctc caaaggcccc atccgctgtg accgctgtgg ctacaatacc    660
aaccggtatg accactacat ggcacacctg aagcaccacc tgcgagctgg cgagaacgag    720
cgcatctaca agtgcatcat ctgcacgtac acgacggtca gcgagtacca ctggaggaaa    780
cacctgagaa accatttccc caggaaagtc tacacctgca gcaagtgcaa ctacttctca    840
gacagaaaaa ataactacgt tcagcacgtg cgaactcaca caggagaacg cccgtataaa    900
tgtgaacttt gtccttactc aagctctcag aagactcatc taacgcgaca catgcggact    960
cattcaggtg agaagccatt taaatgtgat cagtgcaatt atgtggcctc taatcagcat   1020
gaagtgaccc gacatgcaag acaggttcac aacgggccta aacctcttaa ttgcccgcac   1080
tgtgactaca aaacagcaga tagaagcaac ttcaaaaagc acgtggagct gcatgttaac   1140
ccacggcagt tcaactgccc cgtgtgtgac tacgcggctt ctaagaagtg taatctacaa   1200
taccatttca aatctaagca tcccacctgt cccagcaaaa caatggatgt ctccaaagtg   1260
aagctaaaga aaaccaaaaa gagagaggct gacctgctta ataacgccgt cagcaacgag   1320
aagatggaga atgagcaaac aaaaacaaag gggatgtgt ctgggaagaa gaacgagaaa   1380
cctgtaaaag ctgtgggaaa agatgcttca aaagagaaga agcctggtag cagtgtctca   1440
gtggtccagg taactaccag gactcggaag tcagcggtgg cggcggagac taaagcagca   1500
gaggtgaaac acacagacgg acaaacagga aacaatccag aaaagccctg taaagccaag   1560
aaaaacaaaa gaaagaagga tgctgaggcc catccctccg aagagcctgt gaacgaggga   1620
ccagtgacaa aaaagaaaaa gaagtctgag tgcaaatcaa aaatcggtac caacgtgcca   1680
aagggcggcg gccgagcgga ggagaggccg ggggtcaaga agcaaagcgc ttcccttaag   1740
aaaggcacaa agaagacgcc gcccaagaca aagacaagta aaaaaggtgg caaacttgct   1800
ccaaagggga tggggcagac agaaccttct tctggggcat tggctcaagt gggggtgtct   1860
ccagaccctg ccctcattca ggcagaggtc accgggtcag gatcttctca gacagagctt   1920
ccttcaccca tggatattgc taagtcagag cccgcccaga tggaggtttc cctaacaggg   1980
ccacctccgg tggagcctgc tcaaatggag ccatcgcctg cgaaacctcc ccaggtagaa   2040
gcacccactt acccccagcc tccccaaagg gggcctgccc ctcccacggg gcctgcccct   2100
cccacggggc ctgcccctcc cacggagcct gcccctccca cggggcttgc cgagatggaa   2160
ccttctccca cggagccttc ccagaaggaa ccacctccca gtatggagcc tccctgcccc   2220
gaggagctgc ctcaggccga gccacctcct atggaggatt gtcagaagga gctgccttct   2280
cccgtggagc ccgctcagat tgaggttgct cagacggccc ctacgcaggt tcaggaggag   2340
ccccctcctg tctcggagcc acctcgggtg aagccaacca aaagatcatc tctccggaaa   2400
gacagagcag agaaggagct gagcctgctg agtgagatgg cgcggcagga gcaggtcctc   2460
atgggggttg gcttggtgcc tgttagagac agcaagcttc tgaagggaaa caagagcgcc   2520
caggaccccc cagccccacc gtcaccatcg ccaaagggaa actcgaggga agagacaccc   2580
aaggaccaag aaatggtctc tgatggggaa ggaactatag tattccctct caagaaagga   2640
ggaccagagg aagctggaga gagtccagct gagttggctg ctctcaagga gtctgcccgt   2700
gtttcatcct ctgaacaaaa ctcagccatg ccagagggtg gagcatcaca cagcaagtgt   2760
cagactggct cctctgggct ttgtgacgtg gacactgagc agaagacaga tactgtcccc   2820
atgaaagact ccgcagcaga gccagtgtcc cctcctaccc caacagtgga ccgtgacgca   2880
```

```
gggtcaccag ctgtagtggc ctcccctcct atcacgttgg ctgaaaacga gtctcaggaa   2940

attgatgaag atgaaggcat ccatagccat gatggaagtg acctgagtga caacatgtct   3000

gaggggagtg acgactcagg actgcacggg gctcggccga caccaccaga agctacgtca   3060

aaaaatggga aggcagggtt ggctggtaaa gtgactgagg gagagtttgt gtgtattttc   3120

tgtgatcgtt cttttagaaa ggaaaaagat tatagcaaac acctcaatcg ccacttggtg   3180

aatgtgtact tcctagaaga agcagctgag gagcaggagg agcaggagga gcgggaggag   3240

caggagtag                                                           3249


<210> SEQ ID NO 193
<211> LENGTH: 20
<212> TYPE: DNA
<213> ORGANISM: Artificial Sequence
<220> FEATURE:
<223> OTHER INFORMATION: Primer

<400> SEQUENCE: 193

ctggctcttc cactgcagaa                                                 20


<210> SEQ ID NO 194
<211> LENGTH: 20
<212> TYPE: DNA
<213> ORGANISM: Artificial Sequence
<220> FEATURE:
<223> OTHER INFORMATION: Primer

<400> SEQUENCE: 194

tggtgtttca ggtgtgctgt                                                 20


<210> SEQ ID NO 195
<211> LENGTH: 20
<212> TYPE: DNA
<213> ORGANISM: Artificial Sequence
<220> FEATURE:
<223> OTHER INFORMATION: Primer

<400> SEQUENCE: 195

ctacccccaa tgtgtccgtc                                                 20


<210> SEQ ID NO 196
<211> LENGTH: 20
<212> TYPE: DNA
<213> ORGANISM: Artificial Sequence
<220> FEATURE:
<223> OTHER INFORMATION: Primer

<400> SEQUENCE: 196

aagtcgcagg agacaacctg                                                 20


<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197

gttagaactc atacaggaga                                                 20


<210> SEQ ID NO 198
<211> LENGTH: 20
<212> TYPE: DNA
<213> ORGANISM: Artificial Sequence
```

-continued

```
<220> FEATURE:
<223> OTHER INFORMATION: Primer

<400> SEQUENCE: 198

gaggtttagg cccattgtga                                            20


<210> SEQ ID NO 199
<211> LENGTH: 22
<212> TYPE: DNA
<213> ORGANISM: Artificial Sequence
<220> FEATURE:
<223> OTHER INFORMATION: Primer

<400> SEQUENCE: 199

gtctcctctg acttcaacag cg                                         22


<210> SEQ ID NO 200
<211> LENGTH: 22
<212> TYPE: DNA
<213> ORGANISM: Artificial Sequence
<220> FEATURE:
<223> OTHER INFORMATION: Primer

<400> SEQUENCE: 200

accaccctgt tgctgtagcc aa                                         22


<210> SEQ ID NO 201
<211> LENGTH: 20
<212> TYPE: DNA
<213> ORGANISM: Artificial Sequence
<220> FEATURE:
<223> OTHER INFORMATION: Primer

<400> SEQUENCE: 201

ggtcaccagg gctgctttta                                            20


<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202

ttcccgttct cagccttcac                                            20
```

USE OF TRANSDIFFERENTIATION OF GLIAL CELLS INTO NEURONS IN PREVENTION OR TREATMENT OF DISEASES ASSOCIATED WITH NEURON LOSS-OF-FUNCTION OR DEATH

RELATED APPLICATIONS

The present application claims the benefit of the application No. 202110185323.2 entitled "USE OF TRANSDIFFERENTIATION OF GLIAL CELLS INTO NEURONS FOR PREVENTION OR TREATMENT OF DISEASE ASSOCIATED WITH LOSS OF FUNCTION OR DEATH OF NEURONS" filed on Feb. 10, 2021, which is incorporated herein by reference in its entirety.

TECHNICAL FIELD

The present disclosure relates to the field of biomedicines. More specifically, the present disclosure relates to use of an REST (REI-silencing transcription factor) inhibitor in the prevention and/or treatment of a disease associated with loss of function or death of neurons.

BACKGROUND

Parkinson's disease (PD) is a disease associated with loss of function or death of neurons, characterized by loss of dopamine neurons in the substantia nigra of the midbrain. Currently, the main treatment for Parkinson's disease is a drug represented by levodopa. Meanwhile, the symptoms can be improved to a certain extent by surgical treatment. It should be noted that all these approaches can only partially alleviate the disease conditions, but they cannot prevent the progression of the disease.

Müller glia (MG) are the major neuroglial cells in retinal tissue. In zebrafish, when the retina is damaged, Müller glia can proliferate and differentiate into photoreceptor cells, retinal ganglion cells (RGCs), bipolar cells and other retinal cells, which help to repair the damage. However, in higher mammals, MG loses its ability to differentiate into various functional cells of the retina after retinal maturation. Photoreceptor cells are a special type of nerve cells in the retina and are the only cells in the visual system that capture light signals. Retinitis pigmentosa, congenital amaurosis (LCA), age-related macular degeneration, diabetic retinopathy and other ophthalmic diseases can cause the death of photoreceptor cells, thereby causing blindness. The retinal ganglion cells are nerve cells located in the innermost layer of the retina, and their dendrites are mainly connected with bipolar cells, and their axons extend to the optic papilla to form optic nerve. Degeneration of retinal ganglion cells (RGCs) is the major cause of permanent blindness. RGCs are the only efferent neurons of the retina, and thus degeneration of RGCs may lead to retinal diseases leading to permanent blindness. Therefore, reconstituting functional photoreceptor cells or RGCs helps to restore vision and is a potential therapeutic approach to restoring visual function.

There remains an urgent need in the art to develop new targets and new therapies that can effectively treat a disease associated with loss of function or death of neurons.

SUMMARY

One objective of the present disclosure is to provide a method for producing functional dopamine neurons from glial cells.

Another objective of the present disclosure is to provide use of a REST inhibitor in the prevention and/or treatment of a disease associated with loss of function or death of functional dopamine neurons.

Yet another objective of the present disclosure is to provide a method for producing functional retinal ganglion cells (RGCs) or photoreceptor cells from Müller glia (MG).

Still another objective of the present disclosure is to provide use of a REST inhibitor in the prevention and/or treatment of a visual system disease associated with loss of function or death of RGCs or photoreceptor cells.

In one embodiment, the present disclosure provides a method for producing functional dopamine neurons from glial cells, which comprises transdifferentiating or reprogramming the glial cells into functional dopamine neurons by using a REST inhibitor, wherein the REST inhibitor reduces the expression, content, or activity of a gene of REST, an RNA thereof, or an encoding protein thereof.

In a preferred embodiment, the glial cells are selected from astrocytes, oligodendrocytes, ependymocytes, Schwann cells, NG2 cells, satellite cells, or a combination thereof.

In a more preferred embodiment, the glial cells are astrocytes.

In a preferred embodiment, the astrocytes are from central nervous system, comprising striatum, substantia nigra, ventral tegmental area of a midbrain, spinal cord, hypothalamus, dorsal midbrain, or cerebral cortex.

In a more preferred embodiment, the astrocytes are from the striatum and the substantia nigra.

In another embodiment, the present disclosure provides the use of a REST inhibitor in the preparation of a medicament for preventing and/or treating a disease associated with loss of function or death of functional dopamine neurons, wherein the REST inhibitor reduces the expression, content or activity of a gene of REST, an RNA thereof, or an encoding protein thereof.

In a preferred embodiment, the medicament is formulated for administration to a central nervous system, comprising striatum, substantia nigra, ventral tegmental area of midbrain, spinal cord, hypothalamus, dorsal midbrain or cerebral cortex, etc.

In a more preferred embodiment, the medicament is formulated for administration to the striatum and the substantia nigra.

In a preferred embodiment, the disease associated with loss of function or death of the functional dopamine neurons is a nervous system disease, which comprise stroke, Parkinson's disease, schizophrenia, and depression.

In a more preferred embodiment, the disease associated with loss of function or death of functional dopamine neurons is Parkinson's disease.

In another embodiment, the present disclosure provides a method for producing functional retinal ganglion cells (RGCs) or photoreceptor cells from Müller glia, which comprises transdifferentiating or reprogramming Müller glia into functional RGCs or photoreceptor cells by using a REST inhibitor, wherein the REST inhibitor reduces the expression, content, or activity of a gene of REST, an RNA thereof, or an encoding protein thereof.

In a preferred embodiment, the Müller glia are from retina.

In a preferred embodiment, the photoreceptor cells comprise rod cells and cone cells.

In another embodiment, the present disclosure provides use of a REST inhibitor in the preparation of a medicament for preventing and/or treating a visual system disease associated with loss of function or death of RGCs or photoreceptor cells, wherein the REST inhibitor reduces the expression, content, or activity of a gene of REST, an RNA thereof, or an encoding protein thereof.

In a preferred embodiment, the medicament is formulated for administration to visual system.

In a more preferred embodiment, the medicament is formulated for administrating to subretinal space or vitreous cavity, wherein the medicament plays its role by acting on Müller glia.

In a preferred embodiment, the nervous system disease associated with loss of function or death of RGCs is selected from: visual impairment due to death of RGCs, glaucoma, age-related RGC pathology, optic nerve damage, retinal ischemia or hemorrhage, Leber hereditary optic neuropathy, or a combination thereof.

In a preferred embodiment, the visual system disease associated with loss of function or death of photoreceptor cells is selected from: photoreceptor degeneration or death due to damage or degenerative diseases, macular degeneration, retinitis pigmentosa, diabetes-related blindness, night blindness, color blindness, inherited blindness, congenital amaurosis, or the combination thereof.

In a preferred embodiment, the REST inhibitor is selected from: antibodies, small molecule compounds, microRNA, siRNA, shRNA, antisense oligonucleotides, REST binding proteins and protein domains, polypeptides, aptamers, gene editors, PROTACs, epigenetic regulators, or a combination thereof.

In a preferred embodiment, the REST inhibitor comprises:

(a) a gene-editing protein or an expression vector thereof, an editing system comprising: a CRISPR system (including a CRISPR/dCas system), a ZFN system, a TALEN system, an RNA-editing system, or a combination thereof, and (b) one or more gRNAs or an expression vector thereof, wherein the gRNA is a DNA or an RNA guiding the gene-editing protein to specifically bind to a REST gene, wherein, an RNA-targeting gene-editing protein and an RNA-targeting gRNA are preferable.

In a preferred embodiment, the gRNA comprises a sequence complementary to a target sequence.

In a preferred embodiment, the gRNA guides the gene-editing protein to specifically bind to nucleotides at positions 867-1103 (SEQ ID NO: 3) of REST coding sequence.

In a preferred embodiment, the gRNA comprises a sequence complementary to SEQ ID NO: 3.

In a preferred embodiment, the gRNA comprises a sequence selected from SEQ ID NOs: 4-20 and 83-118 or comprises a sequence encoded by sequences set forth in SEQ ID NOs: 55-62 and 71-76, and preferably, the gRNA comprises a sequence selected from SEQ ID NOs: 10 and 93-103.

In a preferred embodiment, the gRNA comprises a sequence fully complementary to a target sequence, or comprises a complementary sequence having no more than 3 base mismatches to the target sequence.

In a preferred embodiment, the gRNA and target sequence belong to a same species or different species.

In a preferred embodiment, the gRNA and target sequence are from human, cynomolgus monkey, or mouse.

In another embodiment, the present disclosure provides a pharmaceutical composition or a package of drug or a kit comprising a REST inhibitor.

In a preferred embodiment, the REST inhibitor is selected from: antibodies, small molecule compounds, microRNA, siRNA, shRNA, antisense oligonucleotides, REST binding proteins or protein domains, polypeptides, aptamers, gene editors, PROTACs, epigenetic regulators, or a combination thereof.

In a preferred embodiment, the REST inhibitor comprises:

a gene-editing protein or an expression vector thereof, and one or more gRNAs or an expression vector thereof, wherein the gRNA is a DNA or an RNA guiding the gene-editing protein to specifically bind to a REST gene.

In a preferred embodiment, an editing system comprises: a CRISPR system (including a CRISPR/dCas system), a ZFN system, a TALEN system, an RNA-editing system, or a combination thereof.

In a preferred embodiment, the gene-editing protein is an RNA-targeting gene-editing protein.

In a preferred embodiment, the gRNA is an RNA-targeting gRNA.

In a preferred embodiment, the gRNA comprises a sequence complementary to a target sequence.

In a preferred embodiment, the gRNA guides the gene-editing protein to specifically bind to nucleotides at positions 867-1103 (SEQ ID NO: 3) corresponding to a REST coding sequence.

In a preferred embodiment, the gRNA comprises a sequence complementary to SEQ ID NO: 3.

In a preferred embodiment, the gRNA comprises a sequence selected from SEQ ID NOs: 4-20 and 83-118 or comprises a sequence encoded by sequences set forth in SEQ ID NOs: 55-62 and 71-76, and preferably, the gRNA comprises a sequence selected from SEQ ID NOs: 10 and 93-103.

In a preferred embodiment, the gRNA comprises a sequence fully complementary to a target sequence, or comprises a complementary sequence having no more than 3 base mismatches to the target sequence.

In a preferred embodiment, the gRNA and target sequence belong to a same species or different species.

In a preferred embodiment, the gRNA and target sequence are from human, cynomolgus monkey, or mouse.

In a preferred embodiment, the pharmaceutical composition or the package of drug or the kit further comprises a vector or carrier for delivery of the REST inhibitor.

In a preferred embodiment, the vector or carrier is a viral vector, a liposome, a nanoparticle, an exosome, or a virus-like particle, preferably AAV.

In a preferred embodiment, the RNA-targeting gene-editing protein is selected from: Cas13d, CasRx, Cas13X, Cas13a, Cas13b, Cas13c, Cas13Y, and functional domains thereof.

In a more preferred embodiment, the RNA-targeting gene-editing protein is selected from: CasRx, Cas13X, and Cas13Y.

In a more preferred embodiment, the RNA-targeting gene-editing protein is CasRx.

In a preferred embodiment, the pharmaceutical composition or the package of drug or the kit comprises only a single type of gRNA or 2, 3, 4, 5, 6 different gRNAs targeting a REST mRNA sequence.

In another preferred embodiment, the gRNA expression vector encodes only a single type of gRNA or 2, 3, 4, 5, 6 different gRNAs targeting a REST mRNA sequence.

In a preferred embodiment, the expression vector comprises:

a nucleotide sequence encoding the gene-editing protein, the nucleotide sequence being operably linked to a promoter leading to expression of the gene-editing protein, and at least one nucleotide sequence encoding a gRNA targeting a REST mRNA sequence, the nucleotide sequence being operably linked to a promoter leading to expression of the gRNA in mammalian cells, e.g., a U6 promoter.

In a more preferred embodiment, the promoter is a glial cell-specific promoter or a MG-specific promoter.

In a more preferred embodiment, the glial cell-specific promoter is selected from a GFAP promoter, an ALDH1L1 promoter, an EAAT1/GLAST promoter, a glutamine synthetase promoter, an S100β promoter, and an EAAT2/GLT-1 promoter, or the MG cell-specific promoter is selected from a GFAP promoter, an ALDH1L1 promoter, a Glast (also known as Slcla3) promoter, and an Rlbp1 promoter.

In a preferred embodiment, the expression vector is comprised in a nanoparticle.

In a preferred embodiment, the expression vector is a gene therapy vector.

In a more preferred embodiment, the gene therapy vector is a viral gene therapy vector.

In a more preferred embodiment, the expression vector is a viral vector selected from: an adeno-associated viral (AAV) vector, a recombinant adeno-associated viral (rAAV) vector, an adenoviral vector, a lentiviral vector, a retroviral vector, herpesvirus, an SV40 vector, a poxvirus vector, and a combination thereof.

In a more preferred embodiment, the expression vector is an AAV vector or an rAAV vector.

In a preferred embodiment, the composition is locally administered to at least one of the followings: 1) glial cells in retina: ii) glial cells in striatum, preferably glial cells in putamen: iii) glial cells in substantia nigra; iv) glial cells in inner ear: v) glial cells in spinal cord: vi) glial cells in prefrontal cortex: vii) glial cells in motor cortex: viii) glial cells in ventral tegmental area (VTA); and ix) glial cells in hypothalamus.

In a preferred embodiment, the pharmaceutical composition or the package of drug or the kit further comprises i) one or more dopamine neuron-associated factors, or ii) at least one expression vector for expressing the one or more dopamine neuron-associated factors in the glial cells.

In a preferred embodiment, the one or more dopamine neuron-associated factors are selected from: Lmx1a, Lmx1b, FoxA2, Nurr1, Pitx3, Gata2, Gata3, FGF8, BMP, En1, En2, PET1, Pax family proteins, SHH, Wnt family proteins, and TGF-β family proteins.

In a preferred embodiment, the pharmaceutical composition or the package of drug or the kit further comprises: i) one or more factors selected from β-catenin, Oct4, Sox2, Klf4, Crx, Brn3a, Brn3b, Math5, Nr2e3, and Nr1, and/or ii) at least one expression vector for expressing one or more factors selected from β-catenin, Oct4, Sox2, Klf4, Crx, Brn3a, Brn3b, Math5, Nr2e3, and Nr1 in glial cells.

In a preferred embodiment, the composition is further formulated for injection, intracranial administration, intraocular administration, inhalation, parenteral administration, intravenous administration, intramuscular administration, intradermal administration, epidermal administration, or oral administration.

In a preferred embodiment, the AAV vector comprises:

a nucleotide sequence encoding the gene-editing protein, the nucleotide sequence being operably linked to a promoter leading to expression of the gene-editing protein in glial cells; and at least one nucleotide sequence encoding a gRNA targeting a REST mRNA sequence, the nucleotide sequence being operably linked to a promoter leading to expression of the gRNA in mammalian cells, e.g., a U6 promoter.

In a more preferred embodiment, the promoter is a glial cell-specific promoter or a MG-specific promoter.

In a more preferred embodiment, the glial cell-specific promoter is selected from a GFAP promoter, an ALDH1L1 promoter, an EAAT1/GLAST promoter, a glutamine synthetase promoter, an S100β promoter, and an EAAT2/GLT-1 promoter.

In a more preferred embodiment, the MG cell-specific promoter is selected from a GFAP promoter, an ALDH1L1 promoter, a Glast (also known as Slcla3) promoter, and an Rlbp1 promoter.

In a preferred embodiment, the efficiency of transdifferentiation of the glial cells is at least 1%, or at least 10%, 20%, 30%, 40%, or 50%.

In another preferred embodiment, the disease associated with loss of function or death of neurons is selected from: Parkinson's disease, schizophrenia, depression, vision impairment due to death of RGCs, glaucoma, age-related RGC pathology, optic nerve damage, retinal ischemia or hemorrhage, Leber hereditary optic neuropathy, photoreceptor cell degeneration or death due to damage or degenerative diseases, macular degeneration, retinitis pigmentosa, diabetes-related blindness, night blindness, color blindness, inherited blindness, congenital amaurosis, or a combination thereof.

In another preferred embodiment, the RGCs can be integrated into the visual pathway and improve visual function.

In another preferred embodiment, the RGCs can achieve functional projection to the central visual region and improve visual function.

In another preferred embodiment, improving visual function is to improve visual function in a mammal suffering from a retinal disease caused by neurodegeneration.

In another preferred embodiment, the MG cells are transdifferentiated into RGC cells and also into axon-free cells.

In another preferred embodiment, an RGC (1) expresses Brn3a, Rbpms, Foxp2, Brn3c, and/or parvalbumin: (2) is F-RGC, RGC type 3, or PV-RGC: (3) is integrated into an existing retinal pathway in the subject (e.g., central information can be projected to dLGN, and vision can be partially restored by relaying visual information to V1); and/or (4) can receive visual information characterized in that during light stimulation or synaptic connections (for example, with existing functional dLGN neurons in the brain), presynaptic neurotransmitters can produce a biological reaction or generate action potentials.

In another preferred embodiment, dopamine neurons (1) express tyrosine hydroxylase (TH), dopamine transporter (DAT), vesicular monoamine transporter 2 (VMAT2), engrailed homeobox 1 (En1), FoxA2, and/or LIM homeobox transcription factor 1 alpha (Lmx1a): (2) perform the synthesis and release of presynaptic neurotransmitters: (3) are integrated into an existing neuronal circuit in the brain of the subject; and/or (4) are characterized by its ability to establish action potentials, synaptic connections, biogenesis of presynaptic neurotransmitters and/or postsynaptic responses.

In another preferred embodiment, the plurality of neuroglial cells in the striatum are reprogrammed or transdifferentiated, and at least 1% of the glial cells are converted into dopamine neurons.

In another preferred embodiment, the mammal comprises a mammal suffering from a disease associated with loss of function or death of neurons.

In another preferred embodiment, the mammal comprises human or non-human mammal.

In another preferred embodiment, the non-human mammal comprises rodent (e.g., mouse, rat, or rabbit), and primate (e.g., monkey).

In another preferred embodiment, the gene editors are driven by a neuroglial cell-specific promoter (e.g., a GFAP promoter) for expression.

In another preferred embodiment, the gene editor comprises 1 or more gRNAs and gene-editing proteins.

In another preferred embodiment, the gRNA guides the gene-editing protein to specifically bind to the RNA of the REST gene.

In another preferred embodiment, the gRNA guides the gene-editing protein to specifically bind to the mRNA of the REST gene.

In another preferred embodiment, the nucleotide sequence of the gRNA is, for example, set forth in SEQ ID NOs: 4-20, preferably SEQ ID NO: 10.

In another preferred embodiment, the source of the gene-editing protein is selected from: *Streptococcus pyogenes, Staphylococcus aureus, acidaminococcus* sp, *Lachnospiraceae bacterium, Ruminococcus flavefaciens*, or a combination thereof.

In another preferred embodiment, the REST is from a mammal; preferably, it is from human, monkey, mouse, rat, or rabbit: more preferably, it is from human.

In another preferred embodiment, the REST gene comprises a wild-type REST gene and a mutant-type REST gene.

In another preferred embodiment, the mutant type comprises a mutant form in which the function of the encoding protein is not altered after mutation (i.e., the function is the same or substantially the same as the wild-type encoding protein).

In another preferred embodiment, the mutant-type REST gene encodes a polypeptide that is the same or substantially the same as the polypeptide encoded by the wild-type REST gene.

In another preferred embodiment, the mutant-type REST gene comprises a sequence which is 80% or more (preferably 90% or more, more preferably 95% or more, much more preferably 98% or 99% or more) homology to the wild-type REST gene.

In another preferred embodiment, the mutant-type REST gene comprises a polynucleotide truncated or added with 1-60 (preferably 1-30, more preferably 1-10) nucleotides at the 5'- and/or 3'-end of the wild-type REST gene.

In another preferred embodiment, the REST gene comprises a cDNA sequence, a genomic sequence, or a combination thereof.

In another preferred embodiment, the REST protein comprises an active fragment of REST or a derivative thereof.

In another preferred embodiment, the active fragment or the derivative thereof has at least 90%, preferably 95%, more preferably 98% or 99% homology to the REST.

In another preferred embodiment, the active fragment or the derivative thereof has at least 80%, 85%, 90%, 95%, or 100% REST activity.

In another preferred embodiment, the amino acid sequence of the REST protein is selected from:

(i) a polypeptide having an amino acid sequence set forth in SEQ ID NO: 1;

(ii) a polypeptide formed by substituting, deleting or adding one or more (such as 1-10) amino acid residues in the amino acid sequence set forth above, having the protein function, and being derived from (i); or (iii) a polypeptide having an amino acid sequence having 90% or more (preferably 95% or more, more preferably 98% or 99% or more) homology to the amino acid sequence set forth above and having the protein function.

In another preferred embodiment, the nucleotide sequence of the REST gene is selected from:

(a) a polynucleotide encoding a polypeptide having the amino acid sequence set forth above;

(b) a polynucleotide having a sequence set forth in SEQ ID NO: 2;

(c) a polynucleotide having a nucleotide sequence having 95% or more (preferably 98% or more, more preferably 99% or more) homology to the nucleotide sequence set forth above;

(d) a polynucleotide truncated or added with 1-60 (preferably 1-30, more preferably 1-10) nucleotides at the 5'- and/or 3'-end of a polynucleotide having the nucleotide sequence set forth above; and a polynucleotide complementary to any one of the polynucleotides (a)-(d).

In another preferred embodiment, the REST protein is shown in the amino acid sequence described above.

In another preferred embodiment, the nucleic acid encoding the REST protein is shown in the nucleotide sequence described above.

In another preferred embodiment, the region targeted by the REST inhibitor (e.g., gene-editing protein) is positions 15311-15338 of the sequence of the REST gene.

In another preferred embodiment, the REST inhibitor inhibits the activity and/or the expression level of the REST.

In another preferred embodiment, the concentration of the REST inhibitor (titer of virus) is more than $1\times10^{12}$.

In another preferred embodiment, the inhibitory rate of the REST inhibitor against the activity and/or the expression level of the REST is more than 90%, preferably 90%-95%.

In another preferred embodiment, the inhibitor targets astrocytes of the brain tissue.

In another preferred embodiment, the inhibitor targets MG cells of the retina.

In another preferred embodiment, the gRNA guides the gene-editing protein to specifically bind to the mRNA of the REST gene.

In another preferred embodiment, the composition comprises a pharmaceutical composition.

In another preferred embodiment, the composition further comprises other drugs for preventing and/or treating a disease associated with loss of function or death of neurons.

In another preferred embodiment, the composition further comprises other drugs for treating a nervous system disease associated with death of functional neurons.

In another preferred embodiment, the composition further comprises other drugs for preventing and/or treating a retinal disease.

In another preferred embodiment, the expression vector of the gene-editing protein comprises a vector targeting glial cells.

In another preferred embodiment, the expression vector of the gene-editing protein comprises a vector targeting astrocytes of the brain tissue.

In another preferred embodiment, the expression vector of the gene-editing protein comprises a vector targeting MG cells of the retina.

In another preferred embodiment, the vector comprises AAV2, AAV8, or AAV9.

In another preferred embodiment, the gene encoding the gene-editing protein is located in the same expression vector (e.g., an AAV vector) as the gRNA.

In another preferred embodiment, the expression vector of the gene-editing protein and the expression vector of gRNA are the same expression vector (e.g., an AAV vector).

In another preferred embodiment, the expression vector further comprises a neuroglial cell-specific promoter (e.g., a GFAP promoter) for driving expression of the gene-editing protein.

In another preferred embodiment, the formulation of the composition is selected from: a lyophilized formulation, a liquid formulation, or a combination thereof.

In another preferred embodiment, the formulation of the composition is a liquid formulation.

In another preferred embodiment, the formulation of the composition is an injectable formulation.

In another preferred embodiment, the other drugs for preventing and/or treating a disease associated with loss of function or death of neurons are selected from: a dopamine prodrug, a non-ergot dopamine receptor agonist, a monoamine oxidase B inhibitor, or a combination thereof.

In another preferred embodiment, the composition is a cell formulation.

In another preferred embodiment, the expression vector of the gene-editing protein and the expression vector of the gRNA are the same vector or different vectors.

In another preferred embodiment, the weight ratio of the component (a) to the component (b) is 100:1-0.01:1, preferably 10:1-0.1:1, more preferably 2:1-0.5:1.

In another preferred embodiment, in the composition, the content of the component (a) is 0.001%-99%, preferably 0.1%-90%, more preferably 1%-70%.

In another preferred embodiment, in the composition, the content of the component (b) is 0.001%-99%, preferably 0.1%-90%, more preferably 1%-70%.

In another preferred embodiment, in the composition, the content of the component (c) is 1%-99%, preferably 10%-90%, more preferably 30%-70%.

In another preferred embodiment, in the composition, the component (a) and the component (b) and optionally the component (c) account for 0.01 wt %-99.99 wt %, preferably 0.1 wt %-90 wt %, more preferably 1 wt %-80 wt % of the total weight of the composition.

A third aspect of the present disclosure provides a package of drug, which comprises:

(a1) a first container, and a gene-editing protein or an expression vector thereof, or a drug comprising the gene-editing protein or the expression vector thereof, located in the first container, the gene-editing protein being selected from: Cas13d, CasRx, Cas13X, Cas13a, Cas13b, Cas13c, Cas13Y, an RNA-targeting gene-editing protein, or a combination thereof; and (b1) a second container, and a gRNA or an expression vector thereof, or a drug comprising the gRNA or the expression vector thereof, located in the second container, the gRNA being a DNA or an RNA guiding the gene-editing protein to specifically bind to a REST gene.

In another preferred embodiment, the package of drug further comprises:

(c1) a third container, and other drugs for preventing and/or treating a disease associated with loss of function or death of neurons, located in the third container, and/or comprising other drugs for preventing and/or treating a retinal disease, and/or comprising other drugs for treating a nervous system disease associated with death of functional neurons.

In another preferred embodiment, the first container, the second container, and the third container are the same or different containers.

In another preferred embodiment, the drug in the first container is a single formulation comprising the gene-editing protein or the expression vector thereof.

In another preferred embodiment, the drug in the second container is a single formulation comprising the gRNA or the expression vector thereof.

In another preferred embodiment, the drug in the third container is a single formulation comprising other drugs for treating a nervous system disease associated with death of functional neurons.

In another preferred embodiment, the formulation of the drug is selected from: a lyophilized formulation, a liquid formulation, or a combination thereof.

In another preferred embodiment, the formulation of the drug is an oral formulation or an injectable formulation. In another preferred embodiment, the package further comprises an instruction.

It should be understood that within the scope of the present disclosure, the above various technical features of the present disclosure and those specifically described below (e.g., in the examples) may be combined with each other to form new or preferred technical solutions. Due to limited space, such schemes are not described herein.

DETAILED DESCRIPTION

Figure 1:
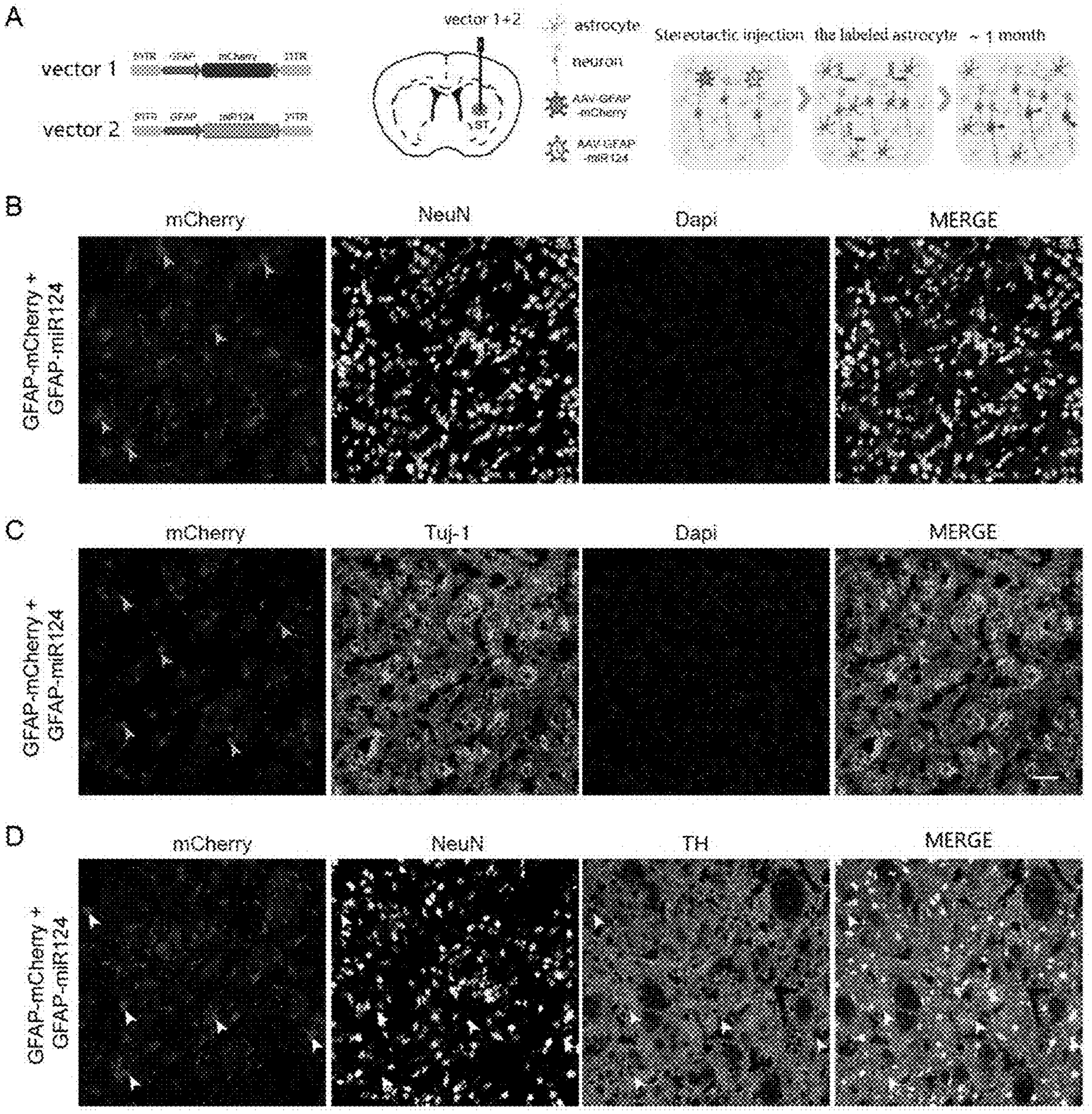
FIG. 1. Analysis whether the glial cells can transdifferentiate into neurons in mice if miR124 is overexpressed. (A) is a schematic diagram of overexpression of miR124 in the brain of a mouse. Vector-1 is used for labeling glial cells by using a glial cell-specific promoter GFAP to promote the expression of mCherry red fluorescent protein. Vector-2 is used for achieving specific expression of miR124 in the glial cells by using the GFAP to promote the expression of miR124. (B) After injection of GFAP-mCherry+GFAP-miR124 into the striatum of a mouse, the orange arrows (indicated by the grey arrows in the black and white drawings) pointed to the labeled glial cells having morphological alterations, but not co-labeled with NeuN. (C) After injection of GFAP-mCherry+GFAP-miR124 into the striatum of a mouse, Tuj-1 being an early marker for neurons, the orange arrows (indicated by the grey arrows in the black and white drawings) pointed to the labeled glial cells which were not co-labeled with Tuj-1, with a scale of 40 microns. (D) After injection of GFAP-mCherry+GFAP-miR124 into the striatum of a mouse, staining was performed by using the neuron-specific marker NeuN and the dopamine neuron-specific marker TH, and the white arrows pointed to the labeled glial cells that were neither co-labeled with NeuN nor with the dopamine-specific marker TH, with a scale of 40 microns.

The present inventor has made extensive and intensive studies and has found, for the first time, that inhibition of expression, content or activity of the gene of REST, an RNA thereof, or an encoding protein thereof in glial cells can effectively induce differentiation of glial cells into functional neurons, thereby treating nervous system diseases associated with loss of function or death of functional neurons. On the basis of this, the present inventor has completed the present invention.

In the present disclosure, degeneration of photoreceptor cells or retinal ganglion cells (RGCs) is the primary cause of permanent blindness. Transdifferentiation of Müller glia (MG) into functional photoreceptor cells or RGCs may help restore vision. The inventors found that by knocking down REST using the RNA-targeting CRISPR system CasRx in a mature mouse retina, MG cells can be directly transformed into functional photoreceptor cells or RGCs. Therefore, REST knockdown mediated by CasRx will be a promising therapy for the treatment of retinal diseases caused by neurodegeneration.

The present application uses the recently characterized RNA-targeting CRISPR system CasRx to inhibit REST. An excellent tool for treating various diseases is provided.

As used herein, Müller glia (MG) are the predominant neuroglial cells in retinal tissue. The retinal ganglion cells (RGCs) are nerve cells located in the innermost layers of the retina, their dendrites are mainly connected with bipolar cells, and their axons extend to the optic papilla to form optic nerve.

In the present disclosure, the gene editors comprise a DNA gene editor, an epigenetic regulatory editor, and an RNA gene editor. In a preferred embodiment, the gene editors of the present disclosure comprise gene-editing proteins and optionally gRNAs.

The term "reprogramming" or "transdifferentiation" may refer to the process of generating cells of a particular lineage (e.g., neurons) from different types of cells (e.g., astrocytes).

Diseases Associated with Loss of Function or Death of Neurons

In the present disclosure, diseases associated with loss of function or death of neurons mainly comprise diseases associated with loss of function or death of dopamine neurons, and visual impairment associated with loss of function or death of retinal ganglion cells or photoreceptor cells.

In a preferred embodiment, diseases associated with loss of function or death of neurons include, but are not limited to: Parkinson's disease, schizophrenia, depression, vision impairment due to death of RGCs, glaucoma, age-related RGC pathology, optic nerve damage, retinal ischemia or hemorrhage, Leber hereditary optic neuropathy, photoreceptor cell degeneration or death due to damage or degenerative diseases, macular degeneration, retinitis pigmentosa, diabetes-related blindness, night blindness, color blindness, inherited blindness, congenital amaurosis, etc.

Astrocyte

Astrocytes are the most numerous cell type in the brain of mammals. They perform a number of functions, comprising biochemical support (e.g., forming a blood-brain barrier), providing nutrients for neurons, maintaining extracellular ionic balance, and participating in repair and scarring after brain and spinal cord injury. Astrocytes can be classified into two types according to the content of glial filaments and the shape of cytoplasmic processes: fibrous astrocytes mostly distributed in the white matter of the brain and spinal cord, having slender processes and fewer branches, and containing a large number of glial filaments in cytoplasm; and protoplasmic astrocytes mostly distributed in the gray matter, and having coarse and short cytoplasmic processes and many branches.

Astrocytes useful in the present disclosure are not particularly limited, and comprise various astrocytes derived from the mammalian central nervous system, for example, from the striatum, ventral tegmental area of the midbrain, hypothalamus, spinal cord, dorsal midbrain or cerebral cortex, preferably, from the striatum.

Functional Neuron

In the present disclosure, functional neurons may refer to neurons capable of sending or receiving information by chemical or electrical signals. In some embodiments, functional neurons exhibit one or more functional properties of mature neurons present in the normal nervous system, including, but not limited to: excitability (e.g., the ability to exhibit an action potential, such as a rapid rise and subsequent fall) (voltage across cell membranes or membrane potential), formation of synaptic connections with other neurons, presynaptic neurotransmitter release, and postsynaptic responses (e.g., excitatory postsynaptic current or inhibitory postsynaptic current).

In some embodiments, the functional neurons are characterized by expressing one or more labels thereof, including, but not limited to, synaptoprotein, synapsin, glutamate decarboxylase 67 (GAD67), glutamate decarboxylase 65 (GAD65), parvalbumin, dopamine- and cAMP-regulated neuronal phosphoprotein 32 (DARPP32), vesicular glutamate transporter 1 (vGLUT1), vesicular glutamate transporter 2 (vGLUT2), acetylcholine, tyrosine hydroxylase (TH), dopamine, vesicular GABA transporter (VGAT), and γ-aminobutyric acid (GABA).

Dopamine Neuron

Dopaminergic neurons contain and release dopamine (DA) as a neurotransmitter. Dopamine belongs to catecholamine neurotransmitters and plays an important biological role in the central nervous system. Dopaminergic neurons in the brain are mainly concentrated in the substantia nigra pars compacta (SNc) region of the midbrain, the ventral tegmental area (VTA), the hypothalamus, and around the brain ventricles. Many experiments have demonstrated that dopaminergic neurons are closely associated with a variety of diseases in the human body, most typically Parkinson's disease.

Gene Editor

In the present disclosure, the gene editors comprise a DNA gene editor and an RNA gene editor. In a preferred embodiment, the gene editors of the present disclosure comprise gene-editing proteins and optionally gRNAs.

Gene-Editing Protein

In the present disclosure, the nucleotide of the gene-editing protein can be obtained by genetic engineering techniques, such as genome sequencing, polymerase chain reaction (PCR), etc., and the amino acid sequence thereof can be deduced from the nucleotide sequence. Sources of the wild-type gene-editing proteins include (but are not limited to): *Ruminococcus lavefaciens, Streptococcus pyogenes, Staphylococcus aureus, Acidaminococcus* sp, *Lachnospiraceae acterium.*

In a preferred embodiment of the present disclosure, the gene-editing proteins include, but are not limited to, Cas13d, CasRx, Cas13X, Cas13a, Cas13b, Cas13c, Cas13Y, and RNA-targeting gene-editing proteins.

REST Protein and Polynucleotide

In the present disclosure, the terms "proteins of the present disclosure", "REST protein", "REST polypeptide", and "REST" are used interchangeably and all refer to a protein or polypeptide having a REST amino acid sequence. They comprise REST proteins with or without the initial methionine. In addition, the term also comprises full-length REST and fragments thereof. The REST proteins referred in the present disclosure comprise complete amino acid sequences thereof, secreted proteins thereof, mutants thereof, and functionally active fragments thereof.

REST proteins are repressor element 1-silencing transcription factors, also known as neuron-restrictive silencer factors (NRSFs).

In the present disclosure, the terms "REST gene", "REST polynucleotide", and "REST gene" are used interchangeably and all refer to a nucleic acid sequence having a REST nucleotide sequence.

The full length of the genome of the human REST gene is 27948 bp (NCBI GenBank accession number is 5978). The full length of the genome of the murine REST gene is 21007 bp (NCBI GenBank accession number is 19712).

Human and murine REST have 72% similarity at the DNA level and 62% protein sequence similarity. It should be understood that nucleotide substitutions in codons are acceptable when the same amino acids are encoded. It should be also understood that nucleotide changes may also be acceptable when conservative amino acid substitutions are made by nucleotide substitutions.

When an amino acid fragment of REST is obtained, a nucleic acid sequence encoding REST can be constructed therefrom, and a specific probe can be designed according to the nucleotide sequence. The full-length nucleotide sequence or a fragment thereof can be obtained by PCR amplification, recombination, or artificial synthesis. For PCR amplification, the primers can be designed according to the REST nucleotide sequences particularly the open reading frame sequences disclosed in the present disclosure, and the relevant sequences can be obtained by amplification using a commercially available cDNA library or a cDNA library prepared by a conventional method known to those skilled in the art as a template. When the sequence is long, it is often necessary to perform two or more PCR amplifications, and then the amplified fragments are spliced together in the correct order.

The relevant sequence, once obtained, can be replicated in large amount by recombination. This is implemented by cloning the sequence into a vector, transferring into a cell, and then isolating from proliferated host cells based on conventional methods.

In addition, the relevant sequence may be synthesized by artificial synthesis, especially when the fragment is short. Generally, a fragment with a long sequence can be obtained by first synthesizing multiple small fragments and then ligating them together.

A DNA sequence encoding the protein (or a fragment thereof, or a derivative thereof) of the present disclosure has already been obtained completely through chemical synthesis. The DNA sequence can then be introduced into various existing DNA molecules (such as vectors) and cells known in the art.

The polynucleotide sequences of the present disclosure can be used to express or produce recombinant REST polypeptides based on conventional recombinant DNA techniques. Generally, the following steps are provided:

(1). transforming or transducing a suitable host cell with a polynucleotide (or a variant) encoding a human REST polypeptide of the present disclosure, or with a recombinant expression vector comprising the polynucleotide;

(2). culturing the host cell in a suitable culture medium; and (3). separating and purifying a protein from the culture medium or cells.

In the present disclosure, the REST polynucleotide sequence may be inserted into the recombinant expression vector. In general, any plasmid or vector can be used as long as it can replicate and is stable in the host. An important feature of expression vectors is that they typically comprise an origin of replication, a promoter, a marker gene, and translation control elements.

Methods well known to those skilled in the art can be used to construct expression vectors comprising the REST-encoding DNA sequence and appropriate transcriptional/translational control signals. These methods comprise in-vitro recombinant DNA techniques, DNA synthesis techniques, in-vivo recombinant techniques, etc. The DNA sequence may be operably linked to a suitable promoter in an expression vector to direct mRNA synthesis. The expression vector further comprises a ribosome binding site for translation initiation and a transcription terminator.

In addition, the expression vector preferably comprises one or more selectable marker genes to provide phenotypic traits for selection of transformed host cells, such as dihydrofolate reductase, neomycin resistance, and green fluorescent protein (GFP) for eukaryotic cell culture, or tetracycline or ampicillin resistance for *Escherichia coli.*

Vectors comprising the appropriate DNA sequences described above, and an appropriate promoter or a control sequence may be used to transform appropriate host cells to express protein.

The host cells may be prokaryotic cells, such as bacterial cells: or lower eukaryotic cells, such as yeast cells: or higher eukaryotic cells, such as mammalian cells. Representative examples comprise: *Escherichia coli, Streptomyces* bacterial cells: fungal cells such as yeast: plant cells: insect cells: animal cells, etc.

Transformation of host cells with recombinant DNA may be performed by conventional techniques well known to those skilled in the art. When the host is a prokaryote, such as *Escherichia coli*, competent cells capable of absorbing DNA can be harvested after exponential phase and processed by $CaCl_2$) transformation method according to steps that are well known in the art. Another method is to use $MgCl_2$. If necessary, the transformation can also be performed by electroporation. When the host is a eukaryote, the following DNA transfection methods can be used: calcium phosphate coprecipitation, conventional mechanical methods such as microinjection, electroporation, liposome packaging, and the like.

The obtained transformants can be cultivated by conventional methods to express the polypeptide encoded by the genes of the present disclosure. The medium is selected from various conventional media depending on the host cells used, and the host cells are incubated under conditions appropriate for their growth. After the host cells have been grown to an appropriate cell density, the selected promoter is induced by suitable methods (e.g., temperature conversion or chemical induction) and the cells are cultured for an additional period of time.

The recombinant polypeptide in the above method may be expressed intracellularly, or on the cell membrane, or secreted extracellularly. If necessary, the recombinant protein can be separated and purified by various isolation methods according to physical, chemical, and other properties. These methods are well known to those skilled in the art. Examples of these methods include, but are not limited to: conventional renaturation treatment, treatment with a protein precipitant (such as salt precipitation), centrifugation, osmotic lysis, sonication treatment, ultracentrifugation, molecular sieve chromatography (gel filtration), adsorption chromatography, ion exchange chromatography, high performance liquid chromatography (HPLC), and other various liquid chromatography techniques, and combinations thereof.

Adeno-Associated Virus

Since adeno-associated viruses (AAVs) are smaller than other viral vectors, are not pathogenic, and can transfect dividing and non-dividing cells, gene therapy methods based on AAV vectors for genetic diseases have received much attention.

Adeno-associated viruses, also known as AAVs, belong to the genus Dependoparvovirus of the family Parvoviridae, and are the simplest single-stranded DNA-defective virus of the group of viruses currently discovered, requiring a helper virus (usually adenovirus) to participate in replication. It encodes the cap and rep genes in two inverted terminal repeats (ITRs). ITRs are crucial for replication and packaging of viruses. The cap gene encodes the capsid protein of the virus, and the rep gene is involved in the replication and integration of the virus. AAVs can infect a variety of cells.

The recombinant adeno-associated viral (rAAV) vector is derived from non-pathogenic wild-type adeno-associated virus, is considered to be one of the most promising gene transfer vectors due to the characteristics of good safety, wide host cell range (dividing and non-dividing cells), low immunogenicity, long duration for expressing exogenous genes in vivo and the like, and is widely applied to gene therapy and vaccine research in the world. Over 10 years of research, the biological properties of recombinant adeno-associated viruses have been well understood, with a lot of data having been accumulated especially in the aspect of their application effect in various cells, tissues and in-vivo experiments. In medical research, rAAVs are used in the study of gene therapy for a variety of diseases (comprising in-vivo experiments, and in-vitro experiments); meanwhile, rAAVs, as characteristic gene transfer vectors, are widely applied to the aspects of gene function research, disease model construction, gene knock-out mouse preparation, and the like.

In a preferred embodiment of the present disclosure, the vector is a recombinant AAV vector. AAVs are relatively small DNA viruses that can be integrated into the genome of cells that they infect in a stable and site-specific manner. They can infect a large series of cells without any effect on cell growth, morphology or differentiation, and they do not appear to be involved in human pathology. AAV genomes have been cloned, sequenced, and characterized. An AAV comprises an inverted terminal repeat (ITR) region of about 145 bases at each terminus, which serves as the viral origin of replication. The remainder of the genome is divided into two important regions with encapsidation functions: the left part of the genome comprising the rep gene involved in viral replication and viral gene expression; and the right part of the genome comprising the cap gene encoding the viral capsid protein.

AAV vectors can be prepared using standard methods in the art. Any serotype of adeno-associated virus is suitable. Methods for purifying vectors can be found, for example, in U.S. Pat. Nos. 6,566,118, 6,989,264, and 6,995,006, the disclosures of which are incorporated herein by reference in their entireties. Preparation of hybrid vectors is described, for example, in PCT application No. PCT/US2005/027091, the disclosure of which is incorporated herein by reference in its entirety. The use of vectors derived from AAVs for in-vitro and in-vivo transfer genes has been described (see, e.g., International Patent Application Publication Nos. WO91/18088 and WO 93/09239; U.S. Pat. Nos. 4,797,368, 6,596,535, and 5,139,941, and European Pat. No. 0488528, all of which are incorporated herein by reference in their entireties). These patent publications describe various AAV-derived constructs in which the rep and/or cap genes are deleted and replaced by a gene of interest, and the use of these constructs to transport the gene of interest in vitro (into cultured cells) or in vivo (directly into an organism). Recombinant replication-deficient AAVs can be prepared by co-transfecting the following plasmids into cell lines infected with a human helper virus (e.g., adenovirus): plasmids containing the nucleic acid sequence of interest flanked by two regions of AAV inverted terminal repeats (ITRs), and plasmids carrying AAV encapsidation genes (rep and cap genes). The AAV recombinants produced are then purified by standard techniques.

In some embodiments, the recombinant vectors are encapsidated into virions (e.g., AAV virions including, but not limited to, AAV1, AAV2, AAV3, AAV4, AAV5, AAV6, AAV7, AAV8, AAV9, AAV-DJ, AAV-rh10, PHP.S, PHP.B, PHP.eB, and AAV2-7m8). Accordingly, the present disclosure comprises recombinant virions (recombinant in that they comprise a recombinant polynucleotide) comprising any of the vectors described herein. Methods for producing such particles are known in the art and are described in U.S. Pat. No. 6,596,535.

Rest Inhibitor and Pharmaceutical Composition

Substances, particularly inhibitors and the like, which interact with the REST gene or protein, can be picked out by various conventional screening methods using the proteins of the present disclosure.

REST inhibitors (or antagonists) useful in the present disclosure may be substances that reduce and eliminate the expression, content and/or activity of the gene of REST, an RNA (e.g., mRNA) thereof, or an encoding protein thereof at the DNA, RNA, protein level.

For example, the REST inhibitors comprise an antibody against REST, an antisense RNA against REST nucleic acid, siRNA, shRNA, miRNA, a gene editor, or a REST activity inhibitor. A preferred REST inhibitor refers to a gene editor capable of inhibiting REST expression.

Preferably, the REST inhibitors of the present disclosure comprise inhibitors targeting positions 15311-15338 of the REST gene sequence. The subjects on which the REST inhibitors of the present disclosure act comprise astrocytes or MG cells.

In a preferred embodiment, the method and steps for inhibiting REST comprise using an antibody against REST to neutralize REST proteins, using shRNA or siRNA or a gene editor carried by a virus (e.g., adeno-associated virus) to silence the REST gene.

The inhibition rate of the REST is generally at least 50% or more, preferably at least 60%, 70%, 80%, 90%, 95% or more, and can be controlled and detected based on conventional techniques, such as flow cytometry, fluorescence quantitative PCR or Western blot, etc.

The REST inhibitors (comprising antibodies, antisense nucleic acids, gene editors, and other inhibitors) of the present disclosure, when administered (dosed) therapeutically, can inhibit the expression and/or activity of REST proteins, thereby inducing differentiation of glial cells into functional neurons, thus treating diseases associated with loss of function or death of neurons. Generally, these materials can be formulated in a non-toxic, inert and pharmaceutically acceptable aqueous carrier medium, wherein the pH is typically about 5-8, preferably about 6-8, although the pH may vary depending on the properties of the material being formulated and the condition being treated. The formulated pharmaceutical composition may be administered by conventional routes including, but not limited to: locally, intramuscular, intracranial, intraocular, intraperitoneal, intravenous, subcutaneous, intradermal administration, autologous cell extraction culture followed by reinfusion, etc.

The present disclosure further provides a pharmaceutical composition, which comprises a safe and effective amount of the inhibitor of the present disclosure (e.g., an antibody, a gene editor, an antisense sequence (e.g., siRNA), or an inhibitor), and a pharmaceutically acceptable carrier or excipient. Such vectors include (but are not limited to): saline, buffer, glucose, water, glycerol, ethanol, and combinations thereof. The pharmaceutical formulation shall match the route of administration. The pharmaceutical composition of the present disclosure may be prepared in the form of injections, for example, using normal saline or an aqueous solution containing glucose and other adjuvants, by a conventional method. The pharmaceutical compositions in the form of a tablet and a capsule may be prepared by a conventional method. The pharmaceutical compositions in the form of an injection, a solution, a tablet and a capsule are preferably manufactured under sterile conditions. The amount of the active ingredient administered is a therapeutically effective amount, for example, from about 1 μg/kg body weight to about 10 mg/kg body weight per day.

The main advantages of the present disclosure comprise that:

(1) The present disclosure has found for the first time that reduction of the expression, content or activity of a gene of REST or an encoding protein thereof in astrocytes can induce differentiation of astrocytes into dopamine neurons, thereby preventing and/or treating Parkinson's disease.

(2) The present disclosure has found for the first time that the inhibition against expression of REST in astrocytes by using gene editors (comprising gene-editing proteins and gRNAs) can transdifferentiate the astrocytes into dopamine neurons, thereby providing a potential approach to the treatment of Parkinson's disease.

(3) The present disclosure has found for the first time that an RNA-targeting CRISPR system CasRx can avoid the risk of permanent DNA changes caused by traditional CRISPR-Cas9 editing. Therefore, CasRx-mediated RNA editing provides an effective means for treating various diseases.

(4) The present disclosure converts MG cells directly into functional photoreceptor cells and RGCs by inhibiting the expression of REST in the retina.

(5) The present disclosure uses the RNA-targeting CRISPR system CasRx to knock down REST, providing an excellent tool capable of treating a variety of diseases.

The present disclosure is further illustrated with reference to the following specific examples. It should be understood that these examples are for illustrative purposes only and are not intended to limit the scope of the present disclosure. Experimental procedures without specific conditions indicated in the following examples are generally performed based on conventional conditions, such as conditions described in Sambrook et al., Molecular Cloning: Laboratory Manual (New York: Cold Spring Harbor Laboratory Press, 1989), or conditions recommended by the manufacturers. Unless otherwise stated, percentages and parts are by weight.

Unless otherwise indicated, all materials and reagents used in the examples of the present disclosure are commercially available products.

General Method

Ethics of animals: the use and the feeding of the animals accord with the guiding principle of the Ethical Committee of the Biomedical Research of the Center for Excellence in Brain Science and Intelligence Technology.

Guide RNA Sequence

The guide RNA targeting mouse REST is, for example, set forth in SEQ ID NOs: 4-20, preferably SEQ ID NO: 10.

Transient Transfection and qPCR Analysis of Cos 7 Cells, 293T or N2a Cells

Cell lines were transiently transfected with 4 μg of CAG-CasRx-P2A-GFP plasmid and 2 μg of U6-gRNA-CMV-mCherry plasmid to determine the inhibitory effect on REST in cell lines in vitro. Meanwhile, the CAG-CasRx-P2A-GFP plasmid was used as a control group for single transfection. Lipofectamine 3000 (Thermo Fisher Scientific) was used according to standard procedures. Two days after transfection, 30000 GFP and mCherry double positive cells were harvested for each sample by fluorescence-activated cell sorting (FACS) (EGFP positive cells were harvested for the control group). The harvested cells were RNA-extracted with Trizol (Ambion) and reversely transcribed into cDNA using a reverse transcription kit (HiScript Q RT SuperMix for qPCR, Vazyme, Biotech), and QPCR analysis was performed using AceQ qPCR SYBR Green Master Mix (Vazyme, Biotech).

The mouse REST-targeting qPCR primers were as follows: an upstream primer, 5'-ctggctcttccactgcagaa-3' (SEQ ID NO: 193); a downstream primer, 5'-tggtgtttcaggtgtgctgt-3' (SEQ ID NO: 194);

The mouse GAPDH-targeting qPCR primers were as follows: an upstream primer, 5'-ctacccccaatgtgtccgtc-3' (SEQ ID NO: 195); a downstream primer, 5'-aagtcgcaggagacaacctg-3' (SEQ ID NO: 196);

The human and cynomolgus monkey REST-targeting qPCR primers were as follows: an upstream primer, 5'-gttagaactcatacaggaga-3' (SEQ ID NO: 197): a downstream primer, 5'-gaggtttaggcccattgtga-3' (SEQ ID NO: 198);

The human GAPDH-targeting qPCR primers were as follows: an upstream primer, 5'-gtctcctctgacttcaacagcg-3' (SEQ ID NO: 199); a downstream primer, 5'-accaccctgttgctgtagccaa-3' (SEQ ID NO: 200);

The cynomolgus monkey GAPDH-targeting qPCR primers were as follows: an upstream primer, 5'-ggtcaccagggctgctttta-3' (SEQ ID NO: 201); a downstream primer, 5'-ttcccgttctcagccttcac-3' (SEQ ID NO: 202).

Stereotactic Injection

The AAV serotype used in this study was AAV8, and the method for stereotactic injection (C57BL/6, approximately two months old) was as described above 2. An AAV mixed solution with the titer of greater than $5\times10^{12}$ vg/mL was injected into the striatum (AP+0.8 mm, ML+1.6 mm, and DV-2.8 mm) using a stereotactic injector at an amount of 1 μL. In miR124 overexpression experiment, the AAV injected was AAV-GFAP-miR124 (approximately $1.7\times10^{13}$ vg/mL). In the REST knockdown experiment, viruses in the control group were GFAP-mCherry (approximately $5\times10^{11}$ vg/mL)+AAV-GFAP-CasRx (titer was approximately $1.2\times10^{13}$ vg/mL, with no gRNAs targeting REST), and AAV viruses in the experimental group were GFAP-mCherry+AAV-GFAP-CasRx-REST (titer was approximately $1.2\times10^{13}$ vg/mL, comprising gRNAs targeting REST), and 1-3 mice were injected per group.

Subretinal Injection

AAV8 was injected subretinally as described above. For subretinal injection, an AAV was injected subretinally using an Olympus microscope (Olympus, Japan) using a Hamilton syringe (32G needle). To determine reprogramming in the intact retinas, a total of 1 μL of GFAP-tdTomato (0.1 μL, approximately $1\times10^{12}$ vg/mL) and GFAP-CasRx-REST (0.9 μL, approximately $1.2\times10^{13}$ vg/mL), or GFAP-tdTomato (0.1 μL, approximately $1\times10^{12}$ vg/mL) and GFAP-CasRx (0.9 μL, approximately $1.2\times10^{13}$ vg/mL) was injected subretinally (C57BL/6 mice, approximately 5 weeks old).

Immunofluorescence Staining

Immunofluorescence staining for brain: approximately 1 month after injection, the mice were perfused to remove the brains, and the brains were fixed with 4% paraformaldehyde (PFA) overnight and dehydrated in 30% sucrose for at least 12 hours. The brains were embedded and made into frozen sections with a thickness of 30 μm. Brain sections were thoroughly rinsed with 0.1 M phosphate buffer (PB) prior to immunofluorescence staining. Primary antibodies for immunofluorescence staining were as follows: rabbit polyclonal NeuN antibody (1:500, #ABN78, Millipore), mouse TH antibody (1:300, MAB318, Millipore), and rat DAT antibody (1:100, MAB369, Millipore). The secondary antibodies were as follows: Alexa Fluor® 488 AffiniPure Donkey Anti-Mouse IgG (H+L) (1:500, 715-545-150, Jackson ImmunoResearch), Alexa Fluor® 488 AffiniPure Donkey Anti-Rabbit IgG (H+L) (1:500, 711-545-152, Jackson ImmunoResearch); Alexa Fluor® 488 AffiniPure Donkey Anti-Rat IgG (H+L) (1:500, 712-545-153, Jackson ImmunoResearch); Cy™5 AffiniPure Donkey Anti-Rabbit IgG (H+L) (1:500, 711-175-152, Jackson ImmunoResearch). After antibody incubation, sections were washed and mounted with a mounting medium (Life Technology). For retinal sections, approximately 1 month after AAV injection, eyes were taken, fixed with 4% paraformaldehyde (PFA) for 2 hours (eyes), and dehydrated in 30% sucrose solution, and then the tissue was sectioned in an embedding cassette with a thickness of 30 μm. Primary antibodies for immunofluorescence staining were as follows: rabbit anti-RBPMS (1:500, 15187-1-AP, Proteintech), mouse-anti-rhodopsin (1:2000, MAB5356, EMD Millipore) and secondary antibodies were as follows: Alexa Fluor® 488 AffiniPure Donkey Anti-Rabbit IgG (H+L) (1:500, 715-545-150, Jackson ImmunoResearch), Alexa Fluor® 488 AffiniPure Donkey Anti-Mouse IgG (H+L) (1:500, 711-545-152, Jackson ImmunoResearch). After antibody incubation, the sections were washed and mounted. Imaging was performed using an Olympus FV3000 microscope.

Sequence Information

Amino Acid Sequence of Human REST Protein (SEQ ID NO: 1):

```
MATQVMGQSSGGGGLFTSSGNIGMALPNDMYDLHDLSKAELAAPQL
IMLANVALTGEVNGSCCDYLVGEERQMAELMPVGDNNFSDSEEGE
GLEESADIKGEPHGLENMELRSLELSVVEPQPVFEASGAPDIYSS
NKDLPPETPGAEDKGKSSKTKPFRCKPCQYEAESEEQFVHHIRVH
SAKKFFVEESAEKQAKARESGSSTAEEGDFSKGPIRCDRCGYNTN
RYDHYTAHLKHHTRAGDNERVYKCIICTYTTVSEYHWRKHLRNHF
PRKVYTCGKCNYFSDRKNNYVQHVRTHTGERPYKCELCPYSSSQK
THLTRHMRTHSGEKPFKCDQCSYVASNQHEVTRHARQVHNGPKPL
NCPHCDYKTADRSNFKKHVELHVNPRQFNCPVCDYAASKKCNLQY
HFKSKHPTCPNKTMDVSKVKLKKTKKREADLPDNITNEKTEIEQT
KIKGDVAGKKNEKSVKAEKRDVSKEKKPSNNVSVIQVTTRTRKSV
TEVKEMDVHTGSNSEKFSKTKKSKRKLEVDSHSLHGPVNDEESST
KKKKKVESKSKNNSQEVPKGDSKVEENKKQNTCMKKSTKKKTLKN
KSSKKSSKPPQKEPVEKGSAQMDPPQMGPAPTEAVQKGPVQVEPP
PPMEHAQMEGAQIRPAPDEPVQMEVVQEGPAQKELLPPVEPAQMV
GAQIVLAHMELPPPMETAQTEVAQMGPAPMEPAQMEVAQVESAPM
QVVQKEPVQMELSPPMEVVQKEPVQIELSPPMEVVQKEPVKIELS
PPIEVVQKEPVQMELSPPMGVVQKEPAQREPPPPREPPLHMEPIS
KKPPLRKDKKEKSNMQSERARKEQVLIEVGLVPVKDSWLLKESVS
TEDLSPPSPPLPKENLREEASGDQKLLNTGEGNKEAPLQKVGAEE
ADESLPGLAANINESTHISSSGQNLNTPEGETLNGKHQTDSIVCE
MKMDTDQNTRENLTGINSTVEEPVSPMLPPSAVEEREAVSKTALA
SPPATMAANESQEIDEDEGIHSHEGSDLSDNMSEGSDDSGLHGAR
PVPQESSRKNAKEALAVKAAKGDFVCIFCDRSFRKGKDYSKHLNR
HLVNVYYLEEAAQGQE
```

Human REST Coding Sequence (SEQ ID NO: 2):

```
atggccacccaggtaatggggcagtcttctggaggaggagggctg
tttaccagcagtggcaacattggaatggccctgcctaacgacatg
tatgacttgcatgacctttccaaagctgaactggccgcacctcag
cttattatgctggcaaatgtggccttaactggggaagtaaatggc
agctgctgtgattacctggtcggtgaagaaagacagatggcagaa
ctgatgccggttggggataacaacttttcagatagtgaagaagga
```

-continued gaaggacttgaagagtctgctgatataaaaggtgaacctcatgga ctggaaaacatggaactgagaagtttggaactcagcgtcgtagaa cctcagcctgtatttgaggcatcaggtgctccagatatttacagt tcaaataaagatcttcccccctgaaacacctggagcggaggacaaa ggcaagagctcgaagaccaaaccctttcgctgtaagccatgccaa tatgaagcagaatctgaagaacagtttgtgcatcacatcagagtt cacagtgctaagaaatttttttgtggaagagagtgcagagaagcag gcaaaagccagggaatctggctcttccactgcagaagagggagat ttctccaagggccccattcgctgtgaccgctgcggctacaatact aatcgatatgatcactatacagcacacctgaaacaccacaccaga gctggggataatgagcgagtctacaagtgtatcatttgcacatac acaacagtgagcgagtatcactggaggaaacatttaagaaaccat tttccaaggaaagtatacacatgtggaaaatgcaactatttttca gacagaaaaaacaattatgttcagcatgttagaactcatacagga gaacgcccatataaatgtgaactttgtccttactcaagttctcag aagactcatctaactagacatatgcgtactcattcaggtgagaag ccatttaaatgtgatcagtgcagttatgtggcctctaatcaacat gaagtaacccgccatgcaagacaggttcacaatgggcctaaacct cttaattgcccacactgtgattacaaaacagcagatagaagcaac ttcaaaaaacatgtagagctacatgtgaacccacggcagttcaat tgccctgtatgtgactatgcagcttccaagaagtgtaatctacag tatcacttcaaatctaagcatcctacttgtcctaataaaacaatg gatgtctcaaaagtgaaactaaagaaaaccaaaaaacgagaggct gacttgcctgataatattaccaatgaaaaaacagaaatagaacaa acaaaaataaaaggggatgtggctggaaagaaaaatgaaaagtcc gtcaaagcagagaaaagagatgtctcaaaagagaaaaagccttct aataatgtgtcagtgatccaggtgactaccagaactcgaaaatca gtaacagaggtgaaagagatggatgtgcatacaggaagcaattca gaaaaattcagtaaaactaagaaaagcaaaaggaagctggaagtt gacagccattctttacatggtcctgtgaatgatgaggaatcttca acaaaaaagaaaaagaaggtagaaagcaaatccaaaaataatagt caggaagtgccaaagggtgacagcaaagtggaggagaataaaaag caaaatacttgcatgaaaaaaagtacaaagaagaaaactctgaaa aataaatcaagtaagaaaagcagtaagcctcctcagaaggaacct gttgagaagggatctgctcagatggaccctcctcagatggggcct gctcccacagaggcggttcagaaggggcccgttcaggtggagccg ccacctcccatggagcatgctcagatggagggtgcccagatacgg cctgctcctgacgagcctgttcagatggaggtggttcaggagggg cctgctcagaaggagctgctgcctcccgtggagcctgctcagatg gtgggtgcccaaattgtacttgctcacatggagctgcctcctccc -continued atggagactgctcagacggaggttgcccaaatggggcctgctccc atggaacctgctcagatggaggttgcccaggtagaatctgctccc atgcaggtggtccagaaggagcctgttcagatggagctgtctcct cccatggaggtggtccagaaggagcctgttcagatagagctgtct cctcccatggaggtggtccagaaggaacctgttaagatagagctg tctcctcccatagaggtggtccagaaggagcctgttcagatggag ttgtctcctcccatgggggtggttcagaaggagcctgctcagagg gagccacctcctcccagagagcctccccttcacatggagccaatt tccaaaaagcctcctctccgaaaagataaaaaggaaaagtctaac atgcagagtgaaagggcacggaaggagcaagtccttattgaagtt ggcttagtgcctgttaaagatagctggcttctaaaggaaagtgta agcacagaggatctctcaccaccatcaccaccactgccaaaggaa aatttaagagaagaggcatcaggagaccaaaaattactcaacaca ggtgaaggaaataaagaagcccctcttcagaaagtaggagcagaa gaggcagatgagagcctacctggtcttgctgctaatatcaacgaa tctacccatatttcatcctctggacaaaacttgaatacgccagag ggtgaaactttaaatggtaaacatcagactgacagtatagtttgt gaaatgaaaatggacactgatcagaacacaagagagaatctcact ggtataaattcaacagttgaagaaccagtttcaccaatgcttccc ccttcagcagtagaagaacgtgaagcagtgtccaaaactgcactg gcatcacctcctgctacaatggcagcaaatgagtctcaggaaatt gatgaagatgaaggcatccacagccatgaaggaagtgacctaagt gacaacatgtcagagggtagtgatgattctggattgcatggggct cggccagttccacaagaatctagcagaaaaaatgcaaaggaagcc ttggcagtcaaagcggctaagggagattttgtttgtatcttctgt gatcgttctttcagaaagggaaaagattacagcaaacacctcaat cgccatttggttaatgtgtactatcttgaagaagcagctcaaggg caggagtaa Nucleotide Sequence at Positions 867-1103 of Human REST Coding Sequence (SEQ ID NO: 3):

caattatgttcagcatgttagaactcatacaggagaacgcccata taaatgtgaactttgtccttactcaagttctcagaagactcatct aactagacatatgcgtactcattcaggtgagaagccatttaaatg tgatcagtgcagttatgtggcctctaatcaacatgaagtaacccg ccatgcaagacaggttcacaatgggcctaaacctcttaattgccc acactgtgatta gRNAs Efficiently Targeting REST Nicked Out in Mouse NA2 Cells (SEO ID NOs: 4-54)

| gRNA | SEQ ID NO. | gRNA sequence | SEQ ID NO. | Target coding sequence | SEQ ID NO. | Target mRNA sequence |
|---|---|---|---|---|---|---|
| mouse-REST-gRNA1 | 4 | agcucgugcaggucguacaugucguugguu | 21 | aaccaacgacatgtacgacctgcacgagct | 38 | aaccaacgacauguacgaccugcacgagcu |
| mouse-REST-gRNA2 | 5 | cgcuguauauuucugggcagcugaggcuuc | 22 | gaagcctcagctgcccagaaatatacagcg | 39 | gaagccucagcugcccagaaauauacagcg |
| mouse-REST-gRNA3 | 6 | cuuuggccuguuucucugcacuuuccuccac | 23 | gtggaggaaagtgcagagaaacaggccaaag | 40 | guggaggaaagugcagagaaacaggccaaag |
| mouse-REST-gRNA4 | 7 | cacuugcugcagguguagacuuuccugggg | 24 | ccccaggaaagtctacacctgcagcaagtg | 41 | ccccaggaaagucuacaccugcagcaagug |
| mouse-REST-gRNA5 | 8 | gcguucuccugugugaguucgcacgugcug | 25 | cagcacgtgcgaactcacacaggagaacgc | 42 | cagcacgugcgaacucacacaggagaacgc |
| mouse-REST-gRNA6 | 9 | gaugagucuucugagagcuugaguaaggac | 26 | gtccttactcaagctctcagaagactcatc | 43 | guccuuacucaagcucucagaagacucauc |
| mouse-REST-gRNA7 | 10 | gucacuucaugcugauuagaggccacau | 27 | atgtggcctctaatcagcatgaagtgac | 44 | auguggccucuaaucagcaugaagugac |
| mouse-REST-gRNA8 | 11 | cgggcaauuaagagguuuaggcccguugug | 28 | cacaacgggcctaaacctcttaattgcccg | 45 | cacaacgggccuaaaccucuuaauugcccg |
| mouse-REST-gRNA9 | 12 | ucacacacggggcaguugaacugccgugggguu | 29 | aacccacggcagttcaactgccccgtgtgtga | 46 | aacccacggcaguucaacugccccgugugu ga |
| mouse-REST-gRNA10 | 13 | ugguauuguagauuacacuucuuag | 30 | ctaagaagtgtaatctacaatacca | 47 | cuaagaaguguaaucuacaauacca |
| mouse-REST-gRNA11 | 14 | cugggacaggugggaugcuuagauuug | 31 | caaatctaagcatcccacctgtcccag | 48 | caaaucuaagcaucccaccugucccag |
| mouse-REST-gRNA12 | 15 | ucuucucguugcugacggcguuauu | 32 | aataacgccgtcagcaacgagaaga | 49 | aauaacgccgucagcaacgagaaga |
| mouse-REST-gRNA13 | 16 | gcggcgucguucuuugugccuuucuuaaggg | 33 | cccttaagaaaggcacaaagaagacgccgc | 50 | cccuuaagaaaggcacaaagaagacgccgc |
| mouse-REST-gRNA14 | 17 | agaagauccugacccggugaccucugccug | 34 | caggcagaggtcaccgggtcaggatcttct | 51 | caggcagaggucaccgggucaggaucuucu |
| mouse-REST-gRNA15 | 18 | gcuccauacugggaggugguuccuucuggg | 35 | cccagaaggaaccacctcccagtatggagc | 52 | cccagaaggaaccaccucccaguauggagc |
| mouse-REST-gRNA16 | 19 | aagcuugcugucucuaacaggcaccaagcc | 36 | ggcttggtgcctgttagagacagcaagctt | 53 | ggcuuggugccuguuagagacagcaagcuu |
| mouse-REST-gRNA17 | 20 | aucugucuucugcucaguguccacgucac | 37 | gtgacgtggacactgagcagaagacagat | 54 | gugacguggacacugagcagaagacagau |

sgRNA Guide Sequences for Epigenetic Methods (SEQ ID NOs: 55-82)
sgRNA1-8 of dSpCas9-KRAB

| gRNA | SEQ ID NO. | Guide sequence | SEQ ID NO. | DNA target |
|---|---|---|---|---|
| sgRNA1 | 55 | ggcgcagcag cagaagaccg | 63 | ggcgcagcag cagaagaccg |
| sgRNA2 | 56 | accgcagcga cggcagaacc | 64 | accgcagcga cggcagaacc |
| sgRNA3 | 57 | ccctggttct gccgtcgctg | 65 | ccctggttct gccgtcgctg |
| sgRNA4 | 58 | agcgacggca gaaccagggc | 66 | agcgacggca gaaccagggc |
| sgRNA5 | 59 | cgggatcaga ccgccggccc | 67 | cgggatcaga ccgccggccc |
| sgRNA6 | 60 | gatcgcaccc cgggatctcg | 68 | gatcgcaccc cgggatctcg |
| sgRNA7 | 61 | gagttggagc ggcggcgacg | 69 | gagttggagc ggcggcgacg |
| sgRNA8 | 62 | atactgtggc tcgggcggcg | 70 | atactgtggc tcgggcggcg |

Sgrna1-6 of dSaCas9-KKH-Krab

| gRNA | SEQ ID NO. | Guide sequence | SEQ ID NO. | DNA target |
|---|---|---|---|---|
| sgRNA 1 | 71 | ggcgggcggcg acggcgcggg | 77 | ggcgggcggcg acggcgcggg |
| sgRNA 2 | 72 | gcgcggcgcag cgtcctgtgc | 78 | gcgcggcgcag cgtcctgtgc |
| sgRNA 3 | 73 | agcgacggcag aaccagggcc | 79 | agcgacggcag aaccagggcc |
| sgRNA 4 | 74 | cggccctggtt ctgccgtcgc | 80 | cggccctggtt ctgccgtcgc |
| sgRNA 5 | 75 | ggaccgtgggc gcacagttca | 81 | ggaccgtgggc gcacagttca |
| sgRNA 6 | 76 | cggccgccgcg ccgcccgagc | 82 | cggccgccgcg ccgcccgagc |

A Series of gRNA Targeting Human REST mRNA Constructed (SEQ ID NOs: 83-190)

| gRNA | SEQ ID NO. | gRNA sequence | SEQ ID NO. | Target coding sequence | SEQ ID NO. | Target mRNA sequence |
|---|---|---|---|---|---|---|
| human REST-gRN A1 | 83 | uaagcugaggugcgg ccaguucagcuuugg | 119 | ccaaagctgaactgg ccgcacctcagctta | 155 | ccaaagcugaacugg ccgcaccucagcuua |
| human REST-gRN A2 | 84 | ucacagcagcugcca uuuacuuccccaguu | 120 | aactggggaagtaaa tggcagctgctgtga | 156 | aacuggggaaguaaa uggcagcugcuguga |
| human REST-gRN A3 | 85 | ccaucugucuuucuu caccgaccaggu | 121 | acctggtcggtgaag aaagacagatgg | 157 | accuggucggugaag aaagacagaugg |
| human REST-gRN A4 | 86 | cuguaaaauaucugga gcaccugaugccuc | 122 | gaggcatcaggtgct ccagatatttacag | 158 | gaggcaucaggugcu ccagauauuuacag |
| human REST-gRN A5 | 87 | uucugcuucauaccg gcauggcuuacagcg | 123 | cgctgtaagccatgc caatatgaagcagaa | 159 | cgcuguaagccaugc caauaugaagcagaa |
| human REST-gRN A6 | 88 | cuuagcacugugaac ucugaugugaugcac | 124 | gtgcatcacatcaga gttcacagtgctaag | 160 | gugcaucacaucaga guucacagugcuaag |
| human REST-gRN A7 | 89 | uugccugcuucucug cacucucuuccac | 125 | gtggaagagagtgca gagaagcaggcaa | 161 | guggaagagagugca gagaagcaggcaa |
| human REST-gRN A8 | 90 | cagcggucacagcga auggggcccuuggag | 126 | ctccaagggccccat tcgctgtgaccgctg | 162 | cuccaagggccccau ucgcugugaccgcug |

-continued

| gRNA | SEQ ID NO. | gRNA sequence | SEQ ID NO. | Target coding sequence | SEQ ID NO. | Target mRNA sequence |
|---|---|---|---|---|---|---|
| human REST-gRNA A9 | 91 | cucauuaucccccagcucucauuauccccagcu | 127 | gaaacaccacaccagagctggggataatgag | 163 | gaaacaccacaccagagcuggggauaaugag |
| human REST-gRNA A10 | 92 | ugauacucgcucacuguuguguaugugc | 128 | gcacatacacaacagtgagcgagtatca | 164 | gcacauacacaacagugagcgaguauca |
| human REST-gRNA A11 | 93 | cguucuccuguaugaguucuaacaugcug | 129 | cagcatgttagaactcatacaggagaacg | 165 | cagcauguuagaacucauacaggagaacg |
| human REST-gRNA A12 | 94 | augagucuucugagaacuugaguaaggac | 130 | gtccttactcaagttctcagaagactcat | 166 | guccuuacucaaguucucagaagacucau |
| human REST-gRNA A13 | 95 | ucuaguuagaugagucuucugagaacuugagu | 131 | actcaagttctcagaagactcatctaactaga | 167 | acucaaguucucagaagacucaucuaacuaga |
| human REST-gRNA A14 | 96 | cauaugucuaguuagaugagucuucugag | 132 | ctcagaagactcatctaactagacatatg | 168 | cucagaagacucaucuaacuagacauaug |
| human REST-gRNA A15 | 97 | aaugaguacgcauaugucuaguuagaug | 133 | catctaactagacatatgcgtactcatt | 169 | caucuaacuagacauaugcguacucauu |
| human REST-gRNA A16 | 98 | cuucucaccugaaugacuucucaccugaauga | 134 | agacatatgcgtactcattcaggtgagaag | 170 | agacauaugcguacucauucaggugagaag |
| human REST-gRNA A17 | 99 | cacugaucacauuuaaauggcuucucaccug | 135 | caggtgagaagccatttaaatgtgatcagtg | 171 | caggugagaagccauuuaaaugugaucagug |
| human REST-gRNA A18 | 100 | aggccacauaacugcacugaucacauuu | 136 | aaatgtgatcagtgcagttatgtggcct | 172 | aaaugugaucagugcaguuauguggccu |
| human REST-gRNA A19 | 101 | guuacuucauguugauuagaggccacau | 137 | atgtggcctctaatcaacatgaagtaac | 173 | auguggccucuaaucaacaugaaguaaC |
| human REST-gRNA A20 | 102 | cccauugugaaccugucuugcaugggggguu | 138 | aacccgccatgcaagacaggttcacaatggg | 174 | aacccgccaugcaagacagguucacaauggg |
| human REST-gRNA A21 | 103 | ugggcaauuaagagguuuaggcccauugug | 139 | cacaatgggcctaaacctcttaattgccca | 175 | cacaaugggccuaaaccucuuaauugccca |
| human REST-gRNA A22 | 104 | uaaucacagugugggcaauuaagagguuu | 140 | aaacctcttaattgcccacactgtgatta | 176 | aaaccucuuaauugcccacacugugauua |
| human REST-gRNA A23 | 105 | auuaggacaaguaggaugcuuagauuug | 141 | caaatctaagcatcctacttgtcctaat | 177 | caaaucuaagcauccuacuuguccuaau |

-continued

| gRNA | SEQ ID NO. | gRNA sequence | SEQ ID NO. | Target coding sequence | SEQ ID NO. | Target mRNA sequence |
|---|---|---|---|---|---|---|
| human REST-gRNA24 | 106 | aagauuccucaucauucacaggaccaugu | 142 | acatggtcctgtgaatgatgaggaatctt | 178 | acaugguccugugaaugaugaggaaucuu |
| human REST-gRNA25 | 107 | agcaggccccuccugaaccaccuccaucug | 143 | cagatggaggtggttcaggaggggcctgct | 179 | cagauggaggugguucaggaggggccugcu |
| human REST-gRNA26 | 108 | cagcagcuccuucugagcaggccccuccug | 144 | caggaggggcctgctcagaaggagctgctg | 180 | caggaggggccugcucagaaggagcugcug |
| human REST-gRNA27 | 109 | auuugggcaaccuccgucugagcagucucc | 145 | ggagactgctcagacggaggttgcccaaat | 181 | ggagacugcucagacggagguugcccaaau |
| human REST-gRNA28 | 110 | ccucuaugggaggagacagcucuaucuu | 146 | aagatagagctgtctcctcccatagagg | 182 | aagauagagcugucuccucccauagagg |
| human REST-gRNA29 | 111 | cuaucuuuaacaggcacuaagccaacuuc | 147 | gaagttggcttagtgcctgttaaagatag | 183 | gaaguuggcuuagugccuguuaaagauag |
| human REST-gRNA30 | 112 | cucucaucugccucuucugcuccuacuuucug | 148 | cagaaagtaggagcagaagaggcagatgagag | 184 | cagaaaguaggagcagaagaggcagaugagag |
| human REST-gRNA31 | 113 | ccauuuaaaguuucaccccucuggcguauuc | 149 | gaatacgccagagggtgaaactttaaatgg | 185 | gaauacgccagagggugaaacuuuaaaugg |
| human REST-gRNA32 | 114 | cuauacugucagucugauguuuaccauuu | 150 | aaatggtaaacatcagactgacagtatag | 186 | aaaugguaaacaucagacugacaguauag |
| human REST-gRNA33 | 115 | uucuucuacugcugaagggggaagcauuggug | 151 | caccaatgcttcccccttcagcagtagaagaa | 187 | caccaaugcuuccccCuucagcaguagaagaa |
| human REST-gRNA34 | 116 | caggaggugaugccagugcaguuuuggac | 152 | gtccaaaactgcactggcatcacctcctg | 188 | guccaaaacugcacuggcaucaccuccug |
| human REST-gRNA35 | 117 | uggaacuggccgagccccaugcaauccag | 153 | ctggattgcatggggctcggccagttcca | 189 | cuggauugcauggggcucggccaguucca |
| human REST-gRNA36 | 118 | cugaaagaacgaucacagaagauacaaac | 154 | gtttgtatcttctgtgatcgttctttcag | 190 | guuuguaucuucugugaucguucuuucag |

Mouse REST Amino Acid Sequence (SEQ ID NO: 191):

MATQVMGQSSGGGSLFNNSANMGMALTNDMYDLHELSKAELAAPQ

LIMLANVALTGEASGSCCDYLVGEERQMAELMPVGDNHFSESEGE

GLEESADLKGLENMELGSLELSAVEPQPVFEASAAPEIYSANKDP

-continued

APETPVAEDKCRSSKAKPFRCKPCQYEAESEEQFVHHIRIHSAKK

FFVEESAEKQAKAWESGSSPAEEGEFSKGPIRCDRCGYNTNRYDH

YMAHLKHHLRAGENERIYKCIICTYTTVSEYHWRKHLRNHFPRKV

-continued

```
YTCSKCNYFSDRKNNYVQHVRTHTGERPYKCELCPYSSSQKTHLT
RHMRTHSGEKPFKCDQCNYVASNQHEVTRHARQVHNGPKPLNCPH
CDYKTADRSNFKKHVELHVNPRQFNCPVCDYAASKKCNLQYHFKS
KHPTCPSKTMDVSKVKLKKTKKREADLLNNAVSNEKMENEQTKTK
GDVSGKKNEKPVKAVGKDASKEKKPGSSVSVVQVTTRTRKSAVAA
ETKAAEVKHTDGQTGNNPEKPCKAKKNKRKKDAEAHPSEEPVNEG
PVTKKKKKSECKSKIGTNVPKGGGRAEERPGVKKQSASLKKGTKK
TPPKTKTSKKGGKLAPKGMGQTEPSSGALAQVGVSPDPALIQAEV
TGSGSSQTELPSPMDIAKSEPAQMEVSLTGPPPVEPAQMEPSPAK
PPQVEAPTYPQPPQRGPAPPTGPAPPTGPAPPTEPAPPTGLAEME
PSPTEPSQKEPPPSMEPPCPEELPQAEPPPMEDCQKELPSPVEPA
QIEVAQTAPTQVQEEPPPVSEPPRVKPTKRSSLRKDRAEKELSLL
SEMARQEQVLMGVGLVPVRDSKLLKGNKSAQDPPAPPSPSPKGNS
REETPKDQEMVSDGEGTIVFPLKKGGPEEAGESPAELAALKESAR
VSSSEQNSAMPEGGASHSKCQTGSSGLCDVDTEQKTDTVPMKDSA
AEPVSPPTPTVDRDAGSPAVVASPPITLAENESQEIDEDEGIHSH
DGSDLSDNMSEGSDDSGLHGARPTPPEATSKNGKAGLAGKVTEGE
FVCIFCDRSFRKEKDYSKHLNRHLVNVYFLEEAAEEQEEQEEREE
QE*
```

Mouse REST Coding Sequence (SEQ ID NO: 192):

```
atggccacccaggtgatggggcagtcttctggaggaggcagtctc
ttcaacaacagtgccaacatgggcatggccttaaccaacgacatg
tacgacctgcacgagctctcgaaagctgaactggcagcccctcag
ctcatcatgttagccaacgtggccctgacgggggaggcaagcggc
agctgctgcgattacctggtcggtgaagagaggcagatggccgaa
ttgatgcccgtgggagacaaccacttctcagaaagtgaaggagaa
ggcctggaagagtcggctgacctcaaagggctggaaaacatggaa
ctgggaagtttggagctaagtgctgtagaaccccagcccgtattt
gaagcctcagctgccccagaaatatacagcgccaataaagatccc
gctccagaaacacccgtggcggaagacaaatgcaggagttctaag
gccaagcccttccggtgtaagccttgccagtacgaagccgaatct
gaagagcagtttgtgcatcacatccggattcacagcgctaagaag
ttctttgtggaggaaagtgcagagaaacaggccaaagcctgggag
tcggggtcgtctccggccgaagagggcgagttctccaaaggcccc
atccgctgtgaccgctgtggctacaataccaaccggtatgaccac
tacatggcacacctgaagcaccacctgcgagctggcgagaacgag
cgcatctacaagtgcatcatctgcacgtacacgacggtcagcgag
taccactggaggaaacacctgagaaaccatttccccaggaaagtc
tacacctgcagcaagtgcaactacttctcagacagaaaaaataac
tacgttcagcacgtgcgaactcacacaggagaacgcccgtataaa
```

-continued

```
tgtgaactttgtccttactcaagctctcagaagactcatctaacg
cgacacatgcggactcattcaggtgagaagccatttaaatgtgat
cagtgcaattatgtggcctctaatcagcatgaagtgacccgacat
gcaagacaggttcacaacgggcctaaacctcttaattgcccgcac
tgtgactacaaaacagcagatagaagcaacttcaaaaagcacgtg
gagctgcatgttaacccacggcagttcaactgccccgtgtgtgac
tacgcggcttctaagaagtgtaatctacaataccatttcaaatct
aagcatcccacctgtcccagcaaaacaatggatgtctccaaagtg
aagctaaagaaaaccaaaaagagagaggctgacctgcttaataac
gccgtcagcaacgagaagatggagaatgagcaaacaaaaaacaaag
gggatgtgtctgggaagaagaacgagaaacctgtaaaagctgtg
ggaaaagatgcttcaaaagagaagaagcctggtagcagtgtctca
gtggtccaggtaactaccaggactcggaagtcagcggtggcggcg
gagactaaagcagcagaggtgaaacacacagacggacaaacagga
aacaatccagaaaagccctgtaaagccaagaaaaacaaaagaaag
aaggatgctgaggcccatccctccgaagagcctgtgaacgaggga
ccagtgacaaaaaagaaaaagaagtctgagtgcaaatcaaaaatc
ggtaccaacgtgccaaagggcggcggccgagcggaggagaggccg
gggtcaagaagcaaagcgcttcccttaagaaaggcacaaagaag
acgccgcccaagacaaagacaagtaaaaaaggtggcaaacttgct
ccaaaggggatggggcagacagaaccttcttctggggcattggct
caagtgggggtgtctccagaccctgccctcattcaggcagaggtc
accgggtcaggatcttctcagacagagcttccttcacccatggat
attgctaagtcagagcccgcccagatggaggtttccctaacaggg
ccacctccggtggagcctgctcaaatggagccatcgcctgcgaaa
cctccccaggtagaagcacccacttacccccagcctccccaaagg
gggcctgcccctcccacggggcctgcccctcccacggggcctgcc
cctcccacggagcctgcccctcccacggggcttgccgagatggaa
ccttctcccacggagccttcccagaaggaaccacctcccagtatg
gagcctccctgccccgaggagctgcctcaggccgagccacctcct
atggaggattgtcagaaggagctgccttctcccgtggagcccgct
cagattgaggttgctcagacggcccctacgcaggttcaggaggag
ccccctcctgtctcggagccacctcgggtgaagccaaccaaaaga
tcatctctccggaaagacagagcagagaaggagctgagcctgctg
agtgagatggcgcggcaggagcaggtcctcatggggggttggcttg
gtgcctgttagagacagcaagcttctgaagggaaacaagagcgcc
caggacccccccagccccaccgtcaccatcgccaaagggaaactcg
agggaagagacacccaaggaccaagaaatggtctctgatggggaa
ggaactatagtattccctctcaagaaaggaggaccagaggaagct
ggagagagtccagctgagttggctgctctcaaggagtctgcccgt
```

-continued

```
gtttcatcctctgaacaaaactcagccatgccagagggtggagca

tcacacagcaagtgtcagactggctcctctgggctttgtgacgtg

gacactgagcagaagacagatactgtccccatgaaagactccgca

gcagagccagtgtcccctcctaccccaacagtggaccgtgacgca

gggtcaccagctgtagtggcctcccctcctatcacgttggctgaa

aacgagtctcaggaaattgatgaagatgaaggcatccatagccat

gatggaagtgacctgagtgacaacatgtctgaggggagtgacgac

tcaggactgcacggggctcggccgacaccaccagaagctacgtca

aaaaatgggaaggcagggttggctggtaaagtgactgagggagag

tttgtgtgtatttctgtgatcgttcttttagaaaggaaaaagat

tatagcaaacacctcaatcgccacttggtgaatgtgtacttccta

gaagaagcagctgaggagcaggaggagcaggaggagcgggaggag

caggagtag
```

EXAMPLE

Example 1: MiR124 Incapable of Transdifferentiating Glial Cells into Neurons or Dopamine Neurons Previous studies have showed that overexpression of miR124 could differentiate stem cells into neurons, and further studies showed that Ptbp1 could transdifferentiate glial cells into neurons via miR124-mediated transdifferentiation. However, these are in-vitro studies. In order to investigate whether miR124 can transdifferentiate glial cells into neurons in animals, an AAV vector that could specifically express miR124 in glial cells was constructed in this study, and it was investigated whether miR124 could transdifferentiate glial cells into neurons in vivo by injecting the AAV overexpressing miR124 in mouse brain (FIG. 1A). Approximately 1 month after injection, materials were obtained and analyzed. It could be found that, unlike the in-vitro studies, fluorescent protein-labeled cells in red were not co-labeled with the neuron-specific marker NeuN (FIG. 1B). This indicated that overexpression of miR124 could not transdifferentiate glial cells into neurons in mice. To further investigate whether cells overexpressing miR124 are in the neonatal neuronal stage, the cells were stained with a neonatal neuron-specific protein marker Tuj-1. It was found that the fluorescently labeled cells in red were co-labeled with Tuj-1 (FIG. 1C). This indicated that overexpression of miR124 could not directly transdifferentiate astrocytes into neurons. It was found in staining analysis with a dopamine-specific protein marker TH that red cells over-expressing miR124 also did not express TH. This indicated that over-expression of miR124 could not transdifferentiate glial cells into dopamine neurons (FIG. 1D). The above results show that overexpression of miR124 in vivo cannot transdifferentiate glial cells into neurons or dopamine neurons.

Example 2: Picking Out gRNAs Efficiently Targeting REST in N2A Cells

Figure 2:
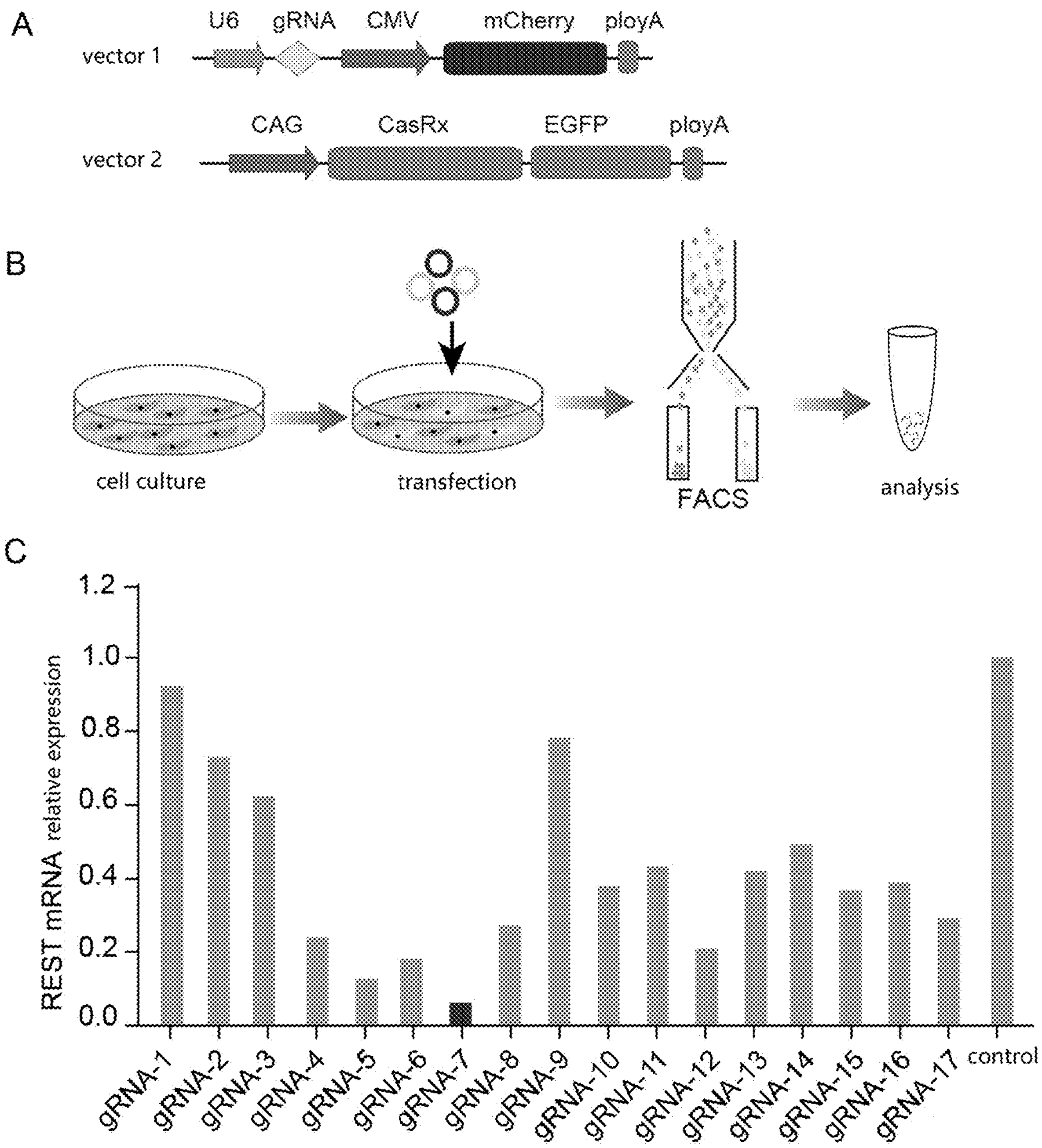
FIG. 2 shows screening of gRNA targeting mouse REST. (A) is a schematic diagram of plasmid construction. Vector-1 is a gRNA expression plasmid, gRNA was driven by U6, and meanwhile the red fluorescent protein was expressed to trace positively transfected cells; Vector-2 is a CasRx expression plasmid, CasRx was driven by CAG, and meanwhile the green fluorescent protein was expressed to trace positively transfected cells. (B) is a schematic diagram of cell transfection and fluorescence-activated cell sorting. After cell transfection, red positive cells and green positive cells were separated by using fluorescence-activated cell sorting, and the content of REST mRNA was measured by using QCPR. (C) After N2A cells were co-transferred with Cas13d and different gRNAs, positive cells were separated by using fluorescence-activated cell sorting, and the content of REST mRNA was measured by using QPCR after N2A cells were transfected with different gRNAs, a lower content of residual REST mRNA indicating higher knockdown efficiency of gRNAs. Red labeled gRNA-7 (indicated by the black label in the black and white drawings) is most effective among the screened gRNAs.

In order to pick out gRNAs for CasRx to efficiently target REST, firstly, 17 gRNAs targeting REST (see SEQ ID NOs: 4-54) were designed and constructed onto a U6-gRNA-CMV-mCherry vector, and different gRNAs were co-transformed into N2A cells with a CAG-CasRx-P2A-EGFP plasmid, respectively (FIGS. 2A and 2B). 48 hours after cell transfection, the transfected GFP and mCherry double-positive cells were separated by using fluorescence-activated cell sorting, and the expression level of REST mRNA was measured by Q-PCR, thereby picking out the gRNA with the highest efficiency for targeting REST. QPCR results indicated that most gRNAs could efficiently knock down the level of REST mRNA, with gRNA-7 being the most efficient and capable of knocking down approximately 94% expression level of REST mRNA (FIG. 2C).

Example 3: Transdifferentiation of Astrocytes into Neurons In Vivo

Figure 3:
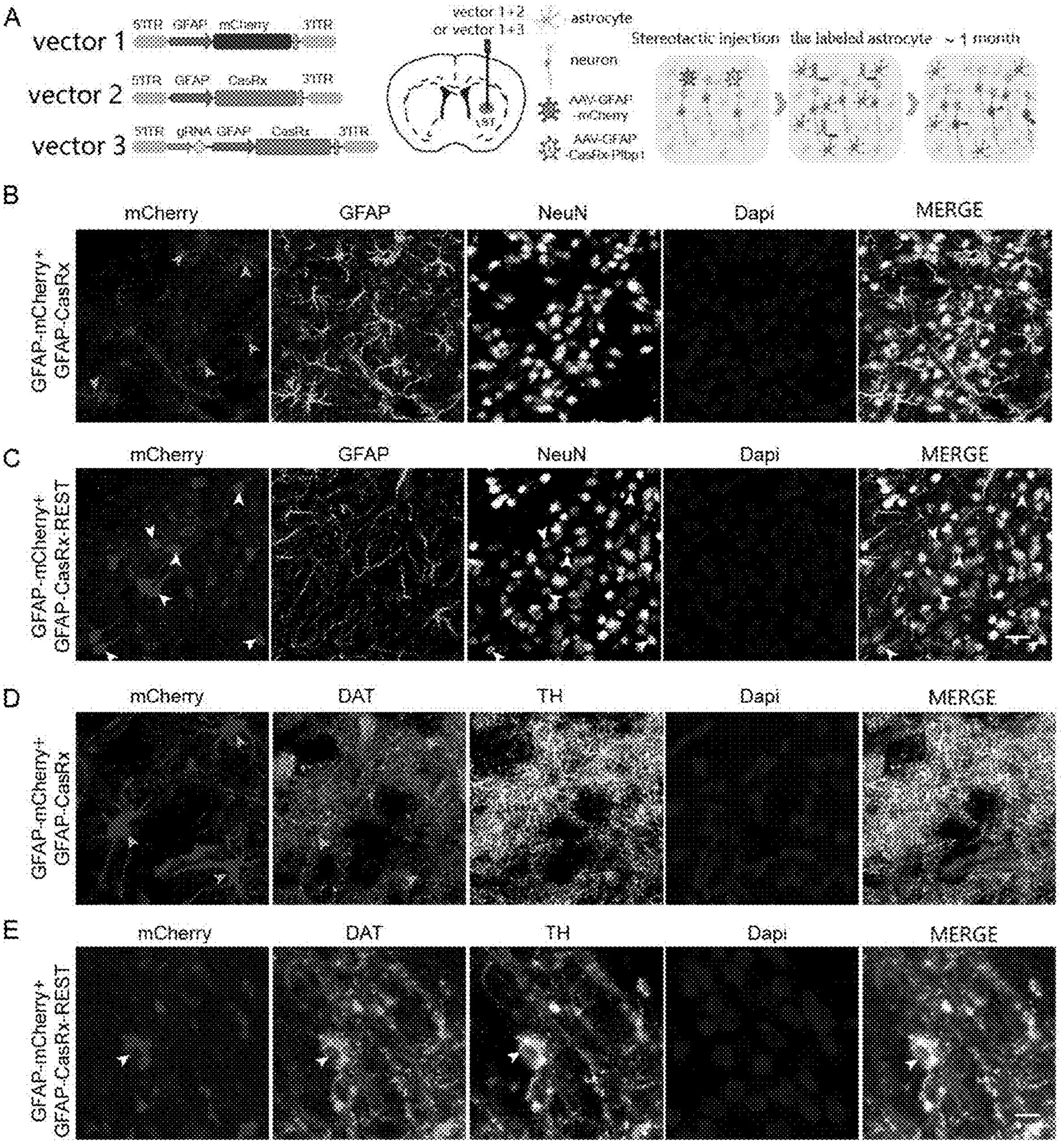
FIG. 3 shows that the REST is inhibited to transdifferentiate glial cells into neurons in the brain of mice. (A) is a schematic diagram of vector construction and transdifferentiation of glial cells in the brain, where the labeling system is GFAP-mCherry, and expression of the fluorescent protein mCherry is promoted by an astrocyte-specific promoter GFAP; Vector 2 is an AAV plasmid in the control group, and CasRx expression is promoted by the astrocyte-specific promoter GFAP; Vector 3 is an AAV plasmid targeting REST, gRNA expression (corresponding to gRNA-7 of FIG. 2) is promoted by U6, and meanwhile CasRx expression is promoted by the astrocyte-specific promoter GFAP; different AAV combinations were injected into the brains of the mice, and materials were taken approximately 1 month after injection. (B) The virus (GFAP-mCherry+GFAP-CasRx) of the control group was injected into the striatum of the mice, orange arrows (indicated by the grey arrows in the black and white drawings) pointed to the labeled astrocytes, green for an astrocyte-specific marker GFAP, white for a mature neuron-specific marker NeuN, the nucleus was stained with Dapi, and the Merge images showed that mCherry signals were co-labeled with GFAP signals and not co-labeled with NeuN. (C) After co-injection of Vector 1 and Vector 3, the REST was knocked down in the striatum of the mice, glial cells were transdifferentiated into neurons, white for a mature neuron-specific marker NeuN, and white arrows pointed to the neurons co-labeled with mCherry and NeuN signals, with a scale of 20 microns. (D-E) After injection of the REST-knockdown AAV group (GFAP-mCherry+GFAP-CasRx-REST), a small fraction of fluorescently labeled cells in red expressed the dopamine neuron-specific cell markers TH and DAT.

Previous studies have shown that in-vitro knockdown of REST expression could transdifferentiate fibroblasts into neurons, although the transdifferentiation efficiency was only about 5%. However, in a complex environment in vivo, whether knockdown of REST expression could achieve a transdifferentiation process or not is a question. To further investigate whether CasRx-mediated REST knockdown technique could achieve the transdifferentiation of glial cells into neurons in vivo, AAV expression vectors were constructed and packaged, and then the AAV vectors were injected into the striatum of mouse brain (FIG. 3A). To label glial cells, mCherry expression was driven by a glial cell-specific promoter GFAP. To specifically express CasRx in glial cells, CasRx expression was also driven by the glial cell-specific promoter GFAP. The virus injected in the control group was a mixed AAV of GFAP-mCherry and GFAP-CasRx, wherein mCherry could label infected glial cells; the AAV combination injected in the experimental group was GFAP-mCherry+GFAP-CasRx-REST (expressing gRNA-7), wherein GFAP-CasRx-REST could specifically target REST mRNA (FIG. 3A). Analysis was performed approximately 1 month after AAV injection. It was found that the fluorescently labeled cells in red of the control group remained co-labeled with the glial cell-specific protein marker GFAP, but not with those stained with the neuron-specific marker NeuN (FIG. 3B). However, in the group injected with GFAP-mCherry+GFAP-CasRx-REST, a large number of mCherry positive cells were found to be co-labeled with NeuN, but not with those stained with GFAP (FIG. 3C). These results indicated that targeted knockdown of REST expression could efficiently transdifferentiate astrocytes into neurons in mice. To further investigate whether knocking down REST could transdifferentiate glial cells into dopamine neurons, the dopamine neuron-specific cell markers TH and DAT were adopted in this study for staining. In the control group injected with GFAP-mCherry+GFAP-CasRx, fluorescently labeled cells in red expressed neither TH nor DAT, while in the group injected with AAVs capable of knocking down REST (GFAP-mCherry+GFAP-CasRx-REST), a small fraction of fluorescently labeled cells in red expressed the dopamine neuron-specific cell markers TH and DAT (FIGS. 3D and 3E). The above results indicated that knockdown of REST expression in the striatum could transdifferentiate astrocytes into dopamine neurons.

Example 4: Inhibition Against REST Gene Expression Using Epigenetic Method

Figure 4:
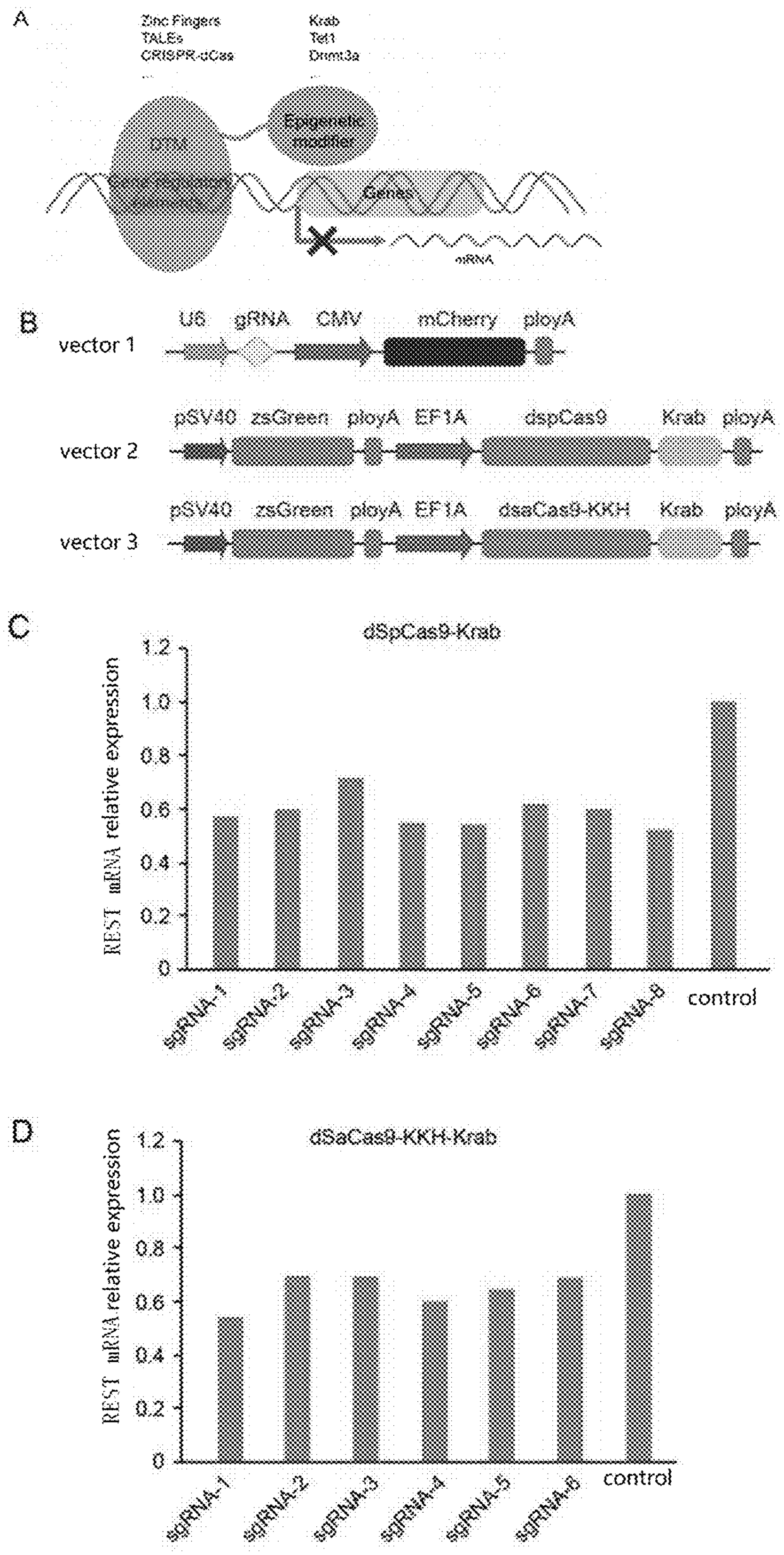
FIG. 4 shows reduction of REST gene expression by using epigenetic regulation techniques. (A) is a schematic diagram of the epigenetic regulation principle, where DTM represents DNA targeting protein or protein structural domain (such as zinc finger protein, TALEs, CRISPR-dCas, etc.), DTM is connected with the epigenetic regulation protein and comprises DNA epigenetic modification related enzymes and histone modification related enzymes, and the expression of downstream gene is regulated under the action of DTM-epigenetic modifier. (B) is a schematic diagram of the plasmid vectors used in this study, with the U6 promoter driving expression of sgRNA and CMV driving expression of the red fluorescent protein (mCherry); in another vector, expression of the green fluorescent protein was promoted by an SV40 promoter, dCas9 (dSpCas9 or dSaCas9-KKH) was driven by EF1A for expression, and N2A cells were co-transferred with Vector 1 (U6-sgRNA-CMV-mCherry) and Vector 2 (dSpCas9-KRAB) or with Vector 1 and Vector 3 (dSaCas9-KKH-KRAB) for research and analysis. (C) After N2A cells were co-transformed with Vector 1 and Vector 2, the inhibitory effect of epigenetic regulation on the REST gene was detected by using Q-PCR. (D) After N2A cells were co-transformed with Vector 1 and Vector 3, the inhibitory effect of epigenetic regulation on the REST gene was detected by using Q-PCR.

Epigenetic modification is also a common method for manipulating gene expression, and in order to investigate whether the epigenetic method can effectively inhibit the expression of REST mRNA, DNA binding proteins (e.g., Zinc fingers, TALEs, CRISPR-dCas, etc.) and epigenetic regulatory elements (e.g., KRAB, Dnmt3a, Tet1, etc.) were expressed by fusion via flexible linker amino acids (FIG. 4A). The DNA targeting proteins used in this study were two different CRISPR-dCas (dSpCas9, dSaCas9-KKH), were subjected to fusion expression together with an epigenetic modification protein Krab inhibitory domain, were used for fluorescence-activated cell sorting by driving expression of EGFP proteins by SV40, and were used for fluorescence-activated cell sorting by driving mCherry fluorescence expression by CMV in the same plasmid vector of U6-gRNA, the gRNA being independently driven by U6 (FIG. 4B). 48 hours after N2A cell transfection, it was found that both dSpCas9-KRAB and dSaCas9-KKH-Krab could effectively reduce the expression of REST mRNA by Q-PCR, and most REST-targeting sgRNAs (see SEQ ID NOs: 55-82) could reduce the level of REST mRNA to about half of the original level (FIGS. 4C and 4D).

Example 5: Efficient CasRx-Mediated REST Knockdown in Human Cells

Figure 5:
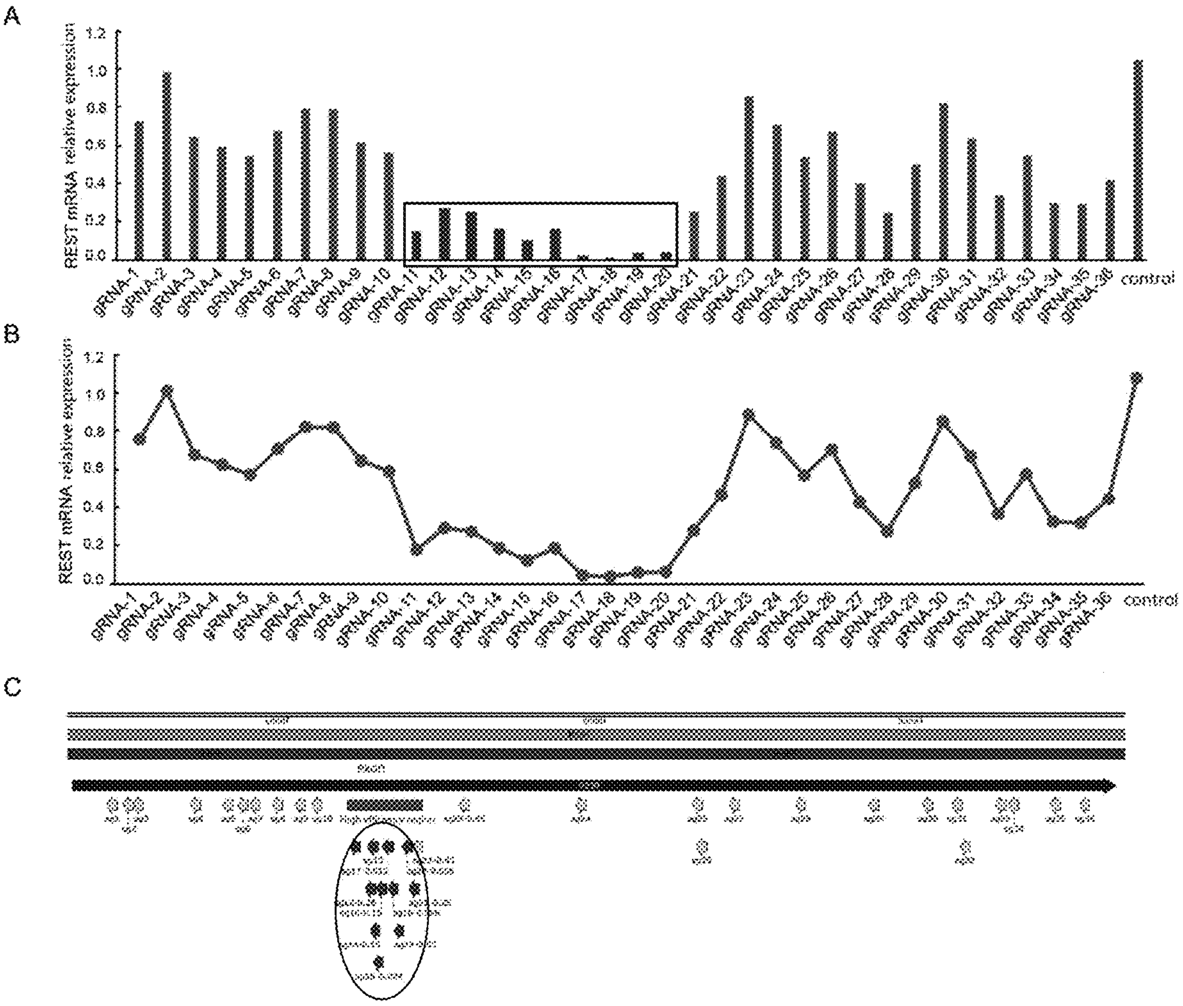
FIG. 5 shows the screening of gRNAs in human cells (293T cells). (A) shows the knockdown efficiency of each gRNA against REST expression in 293T cells, red regions (indicated by the frame in the black and white drawings)_ indicating gRNA regions with high knockdown efficiency. (B) is a REST expression line graph showing the REST knockdown condition of each gRNA, each gRNA corresponding to graph A. (C) shows the distribution position of each gRNA on the REST gene, red-labeled (indicated by the ellipse in the black and white drawings) gRNAs being gRNAs with high inhibition efficiency, and magenta-labeled regions (the "High efficiency region") being efficient gRNA aggregation regions.

To further investigate whether REST expression could be efficiently knocked down in human cells, a series of gRNAs targeting human REST mRNA were constructed (see SEQ ID NOs: 83-190). Different gRNA knockdown efficiencies were measured by Q-PCR, and it was found that most gRNAs could effectively knock down REST mRNA (FIG. 5A). Analysis of these gRNA positions found that the gRNAs with a very high knockdown efficiency were concentrated in a small region of REST mRNA (FIGS. 5B and 5C). The results showed that the region is a preferred position for designing gRNA targeting.

Figure 6:
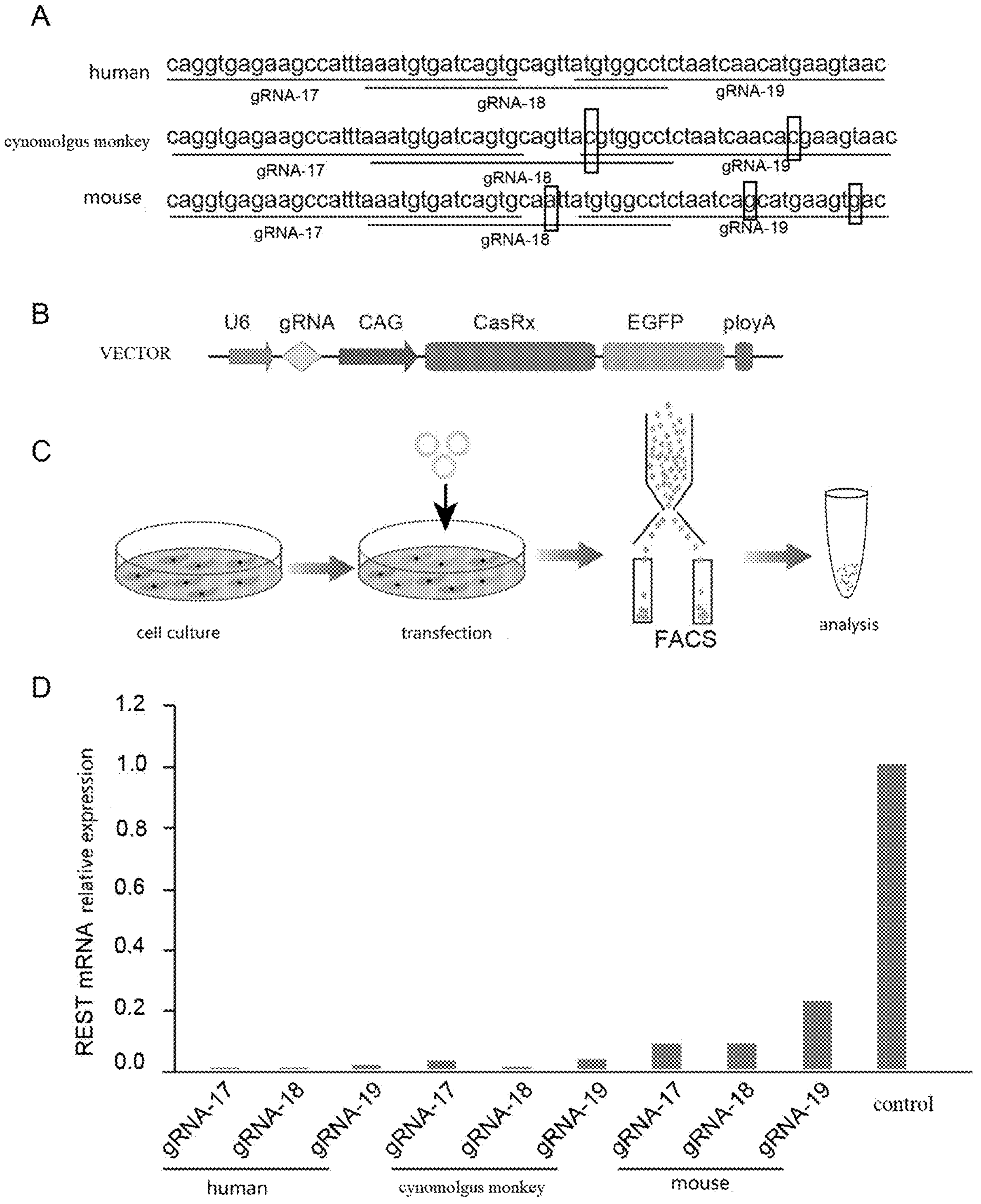
FIG. 6 shows efficient inhibition against the REST in different species. (A) 3 gRNA sequences targeting human REST and mismatched sites thereof in a cynomolgus monkey and a mouse are selected, bases labeled in red (indicated by the frame in the black and white drawings) are sites in the cynomolgus monkey or mouse sequence that are different from those in the human REST sequence, and gRNA-17, gRNA-18 and gRNA-19 are gRNAs of the same serial number targeting human REST in FIG. 5. (B) is a schematic diagram of vector construction, where the gRNA in the expression vectors was driven by U6, the CasRx was driven by CAG, and a green fluorescent protein gene was added in the vector to label positively transfected cells. (C) is a schematic diagram of cell transfection and fluorescence-activated cell sorting. After transfection of different cells, EGFP positive cells were separated by using fluorescence-activated cell sorting and analyzed by using QPCR. (D) The expression level of REST mRNA was analyzed by using QPCR, and the gRNAs (gRNA-17, gRNA-18 and gRNA-19) targeting human REST can also efficiently knock down the expression level of mRNA in the REST of non-human primates (cynomolgus monkeys) and mice.

Example 6: gRNAs Efficiently Targeting Human Capable of Achieving Efficient REST Knockdown in Non-Human Primates and Mice To investigate whether gRNAs efficiently targeting humans could also efficiently target non-human primates or mice, 3 gRNAs were selected in this study from the gRNAs efficiently targeting human REST genes that had been picked out for testing (gRNA 17, gRNA 18, and gRNA 19). The gRNA-17 sequences were homologous in humans, non-human primates and mice, and the sequences were completely consistent: gRNA-18 had 1 base mismatch in cynomolgus monkeys and mice, and gRNA-19 had 2 base mismatches in cynomolgus monkeys and mice (FIG. 6A). As shown in FIG. 6B, in this study, gRNAs and CasRx were constructed into the same expression plasmid, and after 293T, Cos-7 and N2A cells were transfected with the plasmid, the transfected positive cells were separated by using fluorescence-activated cell sorting, and the difference in the expression level of REST mRNA was detected by QPCR (FIG. 6C). The results showed that all of the 3 human-targeting gRNAs could efficiently target REST in non-human primates and mice, and could also effectively knock down the expression level of REST mRNA in non-human primates and mice (FIG. 6D). The above results show that the gRNAs of the present invention can be applied to different species while achieving the technical effects of the present invention as well.

Figure 7:
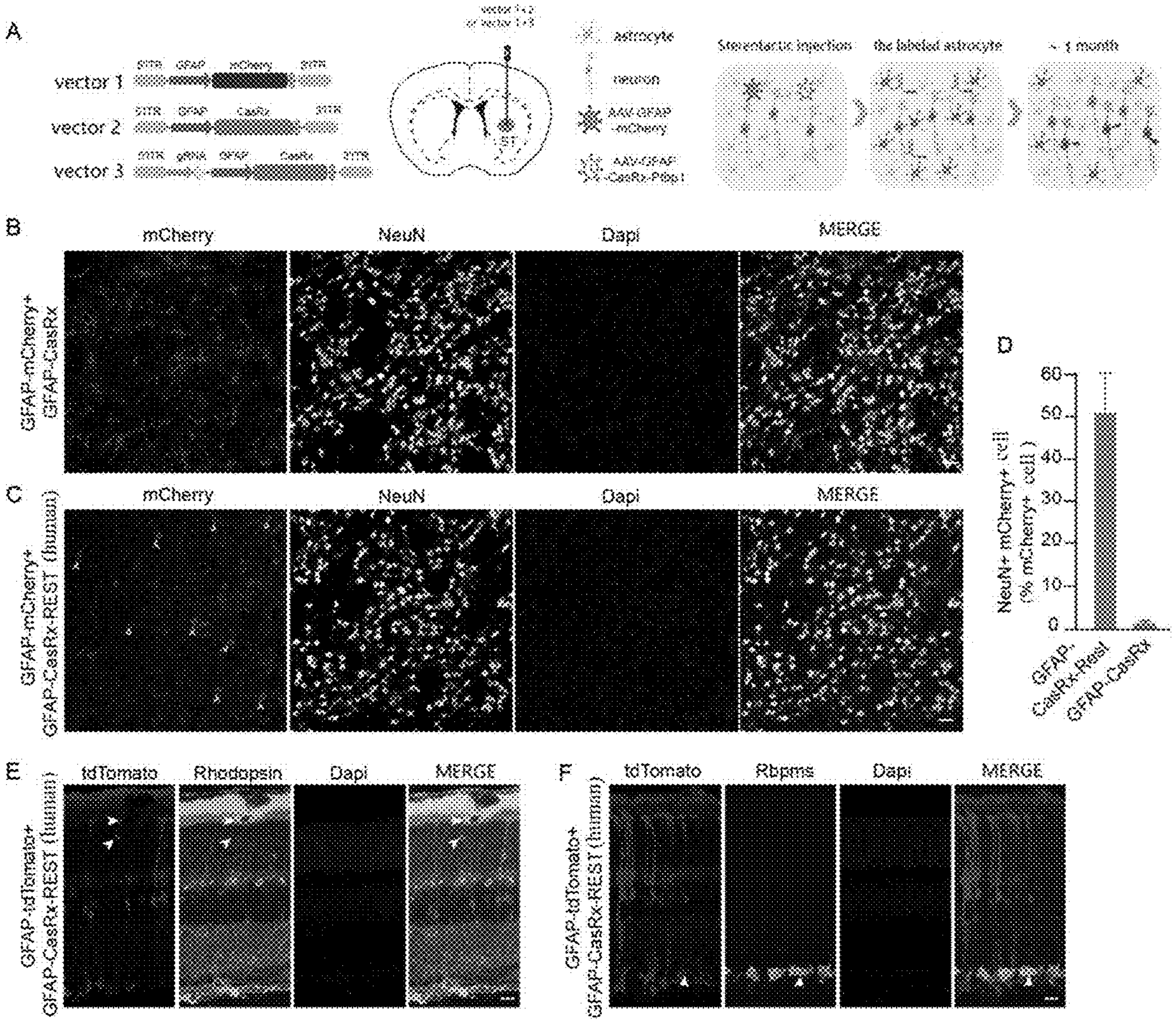
FIG. 7 shows that gRNAs targeting human REST can transdifferentiate glial cells into neurons. (A) is a schematic diagram of AAV vectors and the transdifferentiation process, where GFAP is an astrocyte-specific promoter, mCherry is a red fluorescent protein, CasRx is a gene-editing protein, U6-gRNA is a gRNA expression frame targeting REST promoted by U6, and the selected gRNA is gRNA-17 targeting human REST. Different combinations of AAV were injected into the striatum of mice, and the transdifferentiation effect was analyzed after 1 month. (B) The virus GFAP-mCherry+GFAP-CasRx in the control group was injected into the striatum of a mouse, the red fluorescence signal is GFAP-mCherry, the white fluorescence signal is a mature neuron-specific marker NeuN for staining, and mCherry and NeuN were not co-labeled with each other in the figure. (C) The virus combination of GFAP-mCherry+GFAP-CasRx-REST was injected into the striatum of a mouse, NeuN being a mature neuron-specific marker, and orange arrows (indicated by the grey arrows in the black and white drawings) pointed to neurons co-labeled with mCherry and NeuN, with a scale of 40 microns. (D) shows statistical analysis, showing the proportion of mCherry and NeuN double positive cells in mCherry positive cells (SEM, 3 mice per group). (E) The Müller glia were tried to be transdifferentiated into photoreceptor cells in the retinas, and GFAP is a promoter of the Müller glia in the retinas. After subretinal injection of virus GFAP-tdTomato+GFAP-CasRx-REST, wherein GFAP-tdTomato is used for labeling the retinal Müller glia, GFAP-CasRx-REST is used for knocking down REST in the Müller glia, and Rhodopsin is a specific protein marker of rod cells of photoreceptor cells in the retinas, cells indicated by white arrows simultaneously expressed tdTomato and Rhodopsin. (F) The Müller glia were tried to be transdifferentiated into retinal ganglion cells in the retina. After subretinal injection of virus GFAP-tdTomato+GFAP-CasRx-REST, red cells being GFAP-tdTomato-labeled cells, and green cells being cells stained with retinal ganglion cell-specific protein marker Rbpms, cells indicated by white arrows simultaneously expressed tdTomato and Rbpms, with a scale of 20 microns.

Example 7: CasRx-gRNA System Targeting Human REST Capable of Transdifferentiating Glial Cells into Neurons in Mice To investigate whether human-targeting gRNAs could efficiently transdifferentiate glial cells into neurons, in this study, human-targeting gRNA-17 (gRNA (human)) and CasRx were constructed into AAV vectors and the AAV vectors were packaged. GFAP-CasRx-REST and GFAP-mCherry were co-injected into the mouse brain, and GFAP-CasRx+GFAP-mCherry was injected into the mice in the control group, and then analysis was performed 1 month after injection (FIG. 7A). The results showed that gRNAs targeting human REST could transdifferentiate astrocytes into neurons, fluorescently labeled cells in red were co-labeled with the neuron-specific protein marker NeuN (50.71%±11.12%, SEM, 3 mice per group), while fluorescently labeled cells in red in the mouse brain injected with the AAV of the control group still exhibited typical glial cell morphology and were not co-labeled with NeuN (FIGS. 7B, 7C and 7D). The results show that the CasRx-gRNA system targeting human REST can efficiently transdifferentiate glial cells into neurons, and has the potential of treating diseases associated with the loss of neurons. To further investigate whether knocking down REST in the retina could transdifferentiate Müller glia into functional neurons in the retina, such as photoreceptor cells or retinal ganglion cells, C57 mice at about 5 weeks of age were injected subretinally with an AAV vector of GFAP-tdTomato and GFAP-CasRx-REST (previous documents showed that GFAP could be used as a Müller glia-specific promoter, and GFAP-tdTomato was used to label Müller glia), and after knockdown of REST expression in Müller glia in the retina, cells in the outer granular layer of the retina were found to express both Rhodopsin and tdTomato, while cells in the retinal ganglion cell layer were found to express both Rbpms and tdTomato. These data suggested that knocking down REST in the retina could transdifferentiate Müller glia into photoreceptor cells or retinal ganglion cells, respectively (FIGS. 7E and 7F).

REFERENCES

1. Mccarthy, K. D. & Devellis, J. Preparation Of Separate Astroglial And Oligodendroglial Cell-Cultures From Rat Cerebral Tissue. Journal Of Cell Biology 85, 890-902 (1980).
2. Zhou, H. et al. Cerebellar modules operate at different frequencies. Elife 3, e02536 (2014).
3. Xu, H. T. et al. Distinct lineage-dependent structural and functional organization of the hippocampus. Cell 157, 1552-1564 (2014).
4. Su, J. et al. Reduction of HIP2 expression causes motor function impairment and increased vulnerability to dopaminergic degeneration in Parkinson's disease models. Cell Death Dis 9, 1020 (2018).
5. Chavez, A. et al. Comparison of Cas9 activators in multiple species. Nat Methods 13, 563-567 (2016).
6. Qian, Hao et al. Reversing a model of Parkinson's disease with in situ converted nigral neurons. Nature 582, 550-556 (2020).
7. Zhou, Haibo et al. Glia-to-Neuron Conversion by CRISPR-CasRx Alleviates Symptoms of Neurological Disease in Mice. Cell 181, 590-603.e16 (2020).

All documents mentioned in the present disclosure are incorporated by reference in the present application as if each was individually incorporated by reference. Furthermore, it should be understood that various changes or modifications of the present disclosure can be made by those skilled in the art after reading the above teachings of the present disclosure, and these equivalents also fall within the scope of the appended claims of the present application.

The invention claimed is:

1. A method for preventing and/or treating a disease associated with neuronal functional loss or neuron death, comprising administering to a glial cell of a subject in need thereof a REST (REI-silencing transcription factor) inhibitor, wherein the REST inhibitor is a gene editor which can reduce the expression or activity of a REST gene, a RNA thereof, or an encoded protein thereof, wherein, the glial cells are astrocytes from striatum, and wherein the gene editor specifically binds to the nucleotides at 867-1103 positions (SEQ ID NO: 3) of REST coding sequence.

2. The method of claim 1, wherein the disease is a nervous system disease selected from the group consisting of stroke, Parkinson's disease, schizophrenia, and depression.

3. The method of claim 1, wherein the disease is a visual system disease associated with loss of function or death of RGCs or photoreceptor cells.

4. The method of claim 3, wherein the visual system disease associated with loss of function or death of RGCs is selected from the group consisting of visual impairment due to death of RGCs, glaucoma, age-related RGC pathology, optic nerve damage, retinal ischemia or hemorrhage, Leber hereditary optic neuropathy, and a combination thereof; and wherein the visual system disease associated with loss of function or death of photoreceptor cells is selected from: photoreceptor cell degeneration or death due to damage or degenerative diseases, macular degeneration, retinitis pigmentosa, diabetes-related blindness, night blindness, color blindness, inherited blindness, congenital amaurosis, and a combination thereof.

5. The method of claim 1, wherein the REST inhibitor is formulated for administration to visual system, the striatum, the substantia nigra, the ventral tegmental area of a midbrain, the spinal cord, the hypothalamus, the dorsal midbrain, or the cerebral cortex.

6. The method of claim 5, wherein the visual system is subretinal space or a vitreous cavity.

7. The method of claim 1, wherein gene editor comprises a DNA gene editor, an epigenetic regulatory editor, and an RNA gene editor.

8. The method of claim 1, wherein gene editor is selected from a CRISPR system, a ZFN system, a TALEN system, an RNA-editing system, and a combination thereof.

9. The method of claim 7, wherein gene editor comprises gene-editing protein or an expression vector thereof.

10. The method of claim 9, wherein gene editor comprises one or more gRNAs, or an expression vector thereof.

11. The method of claim 10, wherein the gRNA guides the gene-editing protein specifically binding to the RNA or DNA of the REST gene.

12. The method of claim 10, wherein the gRNA comprises a sequence fully complementary to a target sequence, or comprises a complementary sequence having no more than 3 base mismatches to the target sequence.

13. The method of claim 10, wherein the gRNA comprises a sequence having no more than 3 base mismatches to the sequence selected from SEQ ID NO.: 10 and 93-103, or comprises a sequence having no more than 3 base mismatches to the sequence encoded by the sequences selected from SEQ ID NO.: 10 and 93-103.

* * * * *